United States Patent
Pons et al.

(10) Patent No.: US 12,161,692 B2
(45) Date of Patent: Dec. 10, 2024

(54) SAP FC FUSION PROTEINS AND METHODS OF USE

(71) Applicants: Attralus, Inc., San Francisco, CA (US); UNIVERSITY OF TENNESSEE RESEARCH FOUNDATION, Knoxville, TN (US)

(72) Inventors: Jaume Pons, San Francisco, CA (US); Jonathan S. Wall, Knoxville, TN (US)

(73) Assignees: Attralus, Inc., Burlingame, CA (US); UNIVERSITY OF TENNESSEE RESSEARCH FOUNDATION, Knoxville, TN (US)

( * ) Notice: Subject to any disclaimer, the term of this patent is extended or adjusted under 35 U.S.C. 154(b) by 219 days.

(21) Appl. No.: 17/516,601

(22) Filed: Nov. 1, 2021

(65) Prior Publication Data
US 2022/0160831 A1    May 26, 2022

Related U.S. Application Data

(60) Provisional application No. 63/153,777, filed on Feb. 25, 2021, provisional application No. 63/108,799, filed on Nov. 2, 2020.

(51) Int. Cl.
*A61K 38/17* (2006.01)
*A61P 25/28* (2006.01)
*C12N 15/62* (2006.01)

(52) U.S. Cl.
CPC .......... *A61K 38/1716* (2013.01); *A61P 25/28* (2018.01); *C12N 15/62* (2013.01)

(58) Field of Classification Search
CPC ..... A61K 38/1716; A61K 38/00; A61P 25/28; C12N 15/62; C12N 15/85; C07K 2319/30; C07K 14/4711
See application file for complete search history.

(56) References Cited

U.S. PATENT DOCUMENTS

| | | |
|---|---|---|
| 8,808,666 B2 | 8/2014 | Wall et al. |
| 9,683,017 B2 | 6/2017 | Wall et al. |
| 10,046,050 B2 | 8/2018 | Wall et al. |
| 10,213,506 B2 | 2/2019 | Wall et al. |
| 10,308,685 B2 | 6/2019 | Wall et al. |
| RE47,838 E | 2/2020 | Wall et al. |
| 10,646,568 B2 | 5/2020 | Wall et al. |
| 11,345,730 B2 | 5/2022 | Romeuf et al. |
| 2008/0260738 A1 | 10/2008 | Moore et al. |
| 2009/0191196 A1 | 7/2009 | Pepys |
| 2009/0252729 A1 | 10/2009 | Farrington et al. |
| 2010/0317596 A1 | 12/2010 | Willett et al. |
| 2016/0264637 A1 | 9/2016 | Romeuf et al. |
| 2018/0298071 A1 | 10/2018 | De Romeuf et al. |
| 2022/0356219 A1 | 11/2022 | De Romeuf et al. |

FOREIGN PATENT DOCUMENTS

| | | | |
|---|---|---|---|
| FR | 3012453 A1 * | 5/2015 | ......... A61K 38/1716 |
| WO | 199505394 A1 | 2/1995 | |
| WO | 2002042462 A2 | 5/2002 | |
| WO | WO-2006053301 A2 * | 5/2006 | .............. A61P 11/06 |
| WO | 2008143954 A2 | 11/2008 | |
| WO | 2009000926 A1 | 12/2008 | |
| WO | 2010106180 A2 | 9/2010 | |
| WO | 2010106180 A3 | 12/2010 | |
| WO | 2010141918 A1 | 12/2010 | |
| WO | WO-2010148234 A1 * | 12/2010 | ................ A61P 1/00 |
| WO | 2011119608 A1 | 9/2011 | |
| WO | 2013096847 A1 | 6/2013 | |
| WO | 2015017548 A2 | 2/2015 | |
| WO | 2015063728 A1 | 5/2015 | |
| WO | 2016032949 A1 | 3/2016 | |
| WO | WO-2019197651 A1 * | 10/2019 | ......... A61K 31/5365 |
| WO | 2022094630 A1 | 5/2022 | |

OTHER PUBLICATIONS

Liu, H et. al. "Fc Engineering for Developing Therapeutic Bispecific Antibodies and Novel Scaffolds", 2017, Frontiers in Immunology, 8(38), 1-15. (Year: 2017).*
Elliott, JM et. al. "Antiparallel Conformation of Knob and Hole Aglycosylated Half-Antibody Homodimers Is Mediated by a CH2—CH3 Hydrophobic Interaction", 2014, J. Mol. Biol., 426, 1947-1957. (Year: 2014).*
Almagro, J.C. et al. (Jan. 4, 2018). "Progress and Challenges in the Design and Clinical Development of Antibodies for Cancer Therapy." Front. Immunol. 8(1751):1-19.
Axelrad, M. A. et al. (Aug. 1, 1982). "Further Characterization of Amyloid-Enhancing Factor," Laboratory Investigation, a Journal of Technical Methods and Pathology 47(2):139-146.
Bharadwaj, D. et al. (Jun. 2001). "Serum Amyloid P Component Binds to Fcγ Receptors and Opsonizes Particles for Phagocytosis," The Journal of Immunology 166(11):6735-6741.
Bodin, K. et al. (Nov. 4, 2010, e-pub. May 1, 2011). "Antibodies to Human Serum Amyloid P Component Eliminate Visceral Amyloid Deposits," Nature 468(7320):93-97, 10 pages.

(Continued)

*Primary Examiner* — Nelson B Moseley, II
*Assistant Examiner* — Alyssa Rae Stonebraker
(74) *Attorney, Agent, or Firm* — MORRISON & FOERSTER LLP

(57) ABSTRACT

The present invention relates to SAP-Fc fusion proteins comprising one or more amino acid substitution, for example, C226S and/or C229S. In some aspects, the fusion protein comprises a structure represented by the following formula, from N-terminus to C-terminus, SAP-Fc1-L1-Fc2, wherein Fc1 is a first Fc domain sequence comprising hinge-CH2-CH3, L1 is a linker, and Fc2 is a second Fc domain sequence comprising hinge-CH2-CH3. The present invention also relates to methods of treating amyloid related diseases by administering said SAP-Fc fusion proteins to a subject in need thereof.

19 Claims, 31 Drawing Sheets
Specification includes a Sequence Listing.

(56) References Cited

OTHER PUBLICATIONS

Cox, N. et al. (Aug. 15, 2014, e-pub. Aug. 15, 2015). "Distinct Fcγ Receptors Mediate The Effect of Serum Amyloid P on Neutrophil Adhesion and Fibrocyte Differentiation," J. Immunol. 193(4):1701-1708, 24 pages.
Czajkowsky, D.M. et al. (Oct. 2012). "Fc-Fusion Proteins: New Developments and Future Perspectives," EMBO Mol. Med. 4(10):1015-1028.
Foster, J.S. et al. (Mar. 2017, e-pub. Mar. 1, 2018). "Preliminary Characterization of a Novel Peptide-Fc-Fusion Construct for Targeting Amyloid Deposits," Amyloid 24(SUP1):26-27, 3 pages.
Janeway, C.A. et al. (2001). "The Structure of a Typical Antibody Molecule," In Immunobiology: The Immune System in Health and Disease, 5th edition, Garland Science. Available from: https://www.ncbi.nlm.nih.gov/books/NBK27144/, 7 pages.
Kovalchuk, A.L. et al. (Feb. 5, 2002). "IL-6 Transgenic Mouse Model for Extraosseous Plasmacytoma," Proceedings of The National Academy of Sciences 99(3):1509-1514.
Lagassé, H.D. et al. (Jul. 2019, e-pub. May 6, 2019). "Fc-Fusion Drugs Have Fcγr/C1q Binding and Signaling Properties That May Affect Their Immunogenicity," The AAPS Journal 21(4):62, 10 pages.
Picken, M. M. (May 2007). "New Insights Into Systemic Amyloidosis: The Importance of Diagnosis of Specific Type," Current Opinion In Nephrology and Hypertension 16(3):196-203.
Pilling, D. et al. (Oct. 16, 2018). "The Development of Serum Amyloid P as a Possible Therapeutic," Frontiers in Immunology 9:2328, 1-10.
Pras, M. et al. (Oct. 1, 1969). "Physical, Chemical, and Ultrastructural Studies of Water-Soluble Human Amyloid Fibrils: Comparative Analyses of Nine Amyloid Preparations," The Journal of Experimental Medicine 130(4):777-795.
Rosenzweig, M. et al. (Nov. 18, 2011). "Light Chain (AL) Amyloidosis: Update on Diagnosis and Management," Journal of Hematology & Oncology 4(47):1-8.
Shoji-Hosaka, E. et al. (2006). "Enhanced Fc-Dependent Cellular Cytotoxicity of Fc Fusion Proteins Derived from TNF Receptor II and LFA-3 by Fucose Removal from Asn-Linked Oligosaccharides," J. Biochem. 140(6):777-783.
Solomon, A. et al. (Apr. 1, 1999). "Transgenic Mouse Model of AA Amyloidosis," The American Journal of Pathology 154(4):1267-1272.
Suematsu, S. et al. (Jan. 1992). "Generation of Plasmacytomas With The Chromosomal Translocation t(12; 15) In Interleukin 6 Transgenic Mice," Proceedings of The National Academy of Sciences 89(1):232-235.
Tennent, G.A. et al. (May 1995). "Serum Amyloid P Component Prevents Proteolysis of The Amyloid Fibrils of Alzheimer Disease and Systemic Amyloidosis," Proceedings of the National Academy of Sciences 92(10):4299-4303.
Beierle, S.P. et al. (2016). "A Novel Murine Model of Light Chain Associated (AL) Amyloidosis for Validating Peptide Amyloid Imaging Agents—A SPECT/CT and Microautoradiography Study," 2016 World Molecular Imaging Congress, New York, NY, Sep. 7-10, 2016, Control ID 2500594:1 page.
Lee, S. et al. (2013). "Dual Isotope SPECT Imaging of I-123 and I-125," IEEE Medical Imaging Conference, Seoul, South Korea, Oct. 27-Nov. 2, 2013, 4 pages.

Martin, E.B. et al. (2014). "Detection of Cardiac Amyloidosis by SPECT/CT Imaging Using Both 125I-Serum Amyloid P-Component and The Novel 125I-p5R+14 Peptide," XIVth International Symposium on Amyloidosis, Indianapolis, IN, Apr. 28-May 1, 2014, OP-22:40-41.
Martin, E.B. et al. (Mar. 3, 2016). "Comparative Evaluation of p5+14 With SAP and Peptide p5 By Dual-Energy SPECT Imaging of Mice With AA Amyloidosis," Scientific Reports 6(22695):1-10.
Morgan, G.J. et al. (2020). "The Process of Amyloid Formation Due to Monoclonal Immunoglobulins," Hematology/Oncology Clinics of North America 34(6):1041-1054.
Sirac, C. et al. (2022). "AT-03 Demonstrated Pan-Amyloid Binding and Stimulated The Removal of Amyloid Deposits Through Macrophage-Mediated Phagocytosis," Poster, presented at the XVIII Meeting of the International Society of Amyloidosis, Heidelberg, Germany, Sep. 4-8, 2022, P284:1 page.
Sirac, C. et al. (Nov. 5, 2021). "Pre-Clinical Characterization of a Novel Fusion Protein (AT-03), With Pan-Amyloid Binding and Removal," Blood 138 (Suppl 1):1207, 2 pages.
Wall, J. et al. (May 2011). "The 99mTc-p31 Peptide Offers Enhanced Amyloid Imaging as Compared to SAP-A Quantitative Biodistribution and Dual Energy SPECT Imaging Study," The Journal of Nuclear Medicine 52 (Suppl 1) 228:2 pages.
Wall, J. S. et al. (2006). "Micro-Imaging of Amyloid In Mice," Methods in Enzymology 412:161-182, 20 pages.
Wall, J.S. et al. (2010). "99mTc-Labeled Serum Amyloid P Component as a Tool for Evaluating Novel Amyloid Imaging Agents," XII International Symposium on Amyloidosis, Rome, Italy, Apr. 18-21, 2010, P-103:140-141.
Wall, J.S. et al. (2010). "Rapid Dehalogenation of 124I-SAP in Mice Enhances the Specific Detection of Amyloid: A Dynamic microPET Imaging Study," XII International Symposium on Amyloidosis, Rome, Italy, Apr. 18-21, 2010, P-035:107, 1 page.
Wall, J.S. et al. (2017, e-pub. Aug. 21, 2017). "Pretargeting Immunotherapy: A Novel Treatment Approach for Systemic Amyloidosis," Pharmaceutical Patent Analyst 6(5):215-223.
Wall, J.S. et al. (2018, e-pub. Oct. 30, 2018). "Bifunctional Amyloid-Reactive Peptide Promotes Binding of Antibody 11-1F4 to Diverse Amyloid Types and Enhances Therapeutic Efficacy," PNAS 115(46):E10839-E10848.
Wall, J.S. et al. (Aug. 2012). "Comparative Analysis of Peptide p5 and Serum Amyloid P Component for Imaging AA Amyloid In Mice Using Dual-Isotope SPECT," Molecular Imaging and Biology 14(4):402-407, 1-13.
Wall, J.S. et al. (Dec. 2008). "Quantitative Tomography of Early-Onset Spontaneous AA Amyloidosis In Interleukin 6 Transgenic Mice," Comparative Medicine 58(6):542-550.
Wall, J.S. et al. (Dec. 26, 2012). "AL Amyloid Imaging and Therapy With a Monoclonal Antibody to a Cryptic Epitope on Amyloid Fibrils," PloS One 7(12):e52686, 10 pages.
Wall, J.S. et al. (Sep. 18, 2013). "Evaluation of SPECT Detection of Cardiac Amyloidosis In Mice by Using 125I-p5R+14 Peptide or 125I-SAP," World Molecular Imaging Congress, Savannah, GA, Sep. 18-21, 2013, Poster Session 1, Presentation No. P071:S418-S419.
Wall, J.S. et al. (Sep. 2005). "Quantitative High-Resolution Microradiographic Imaging of Amyloid Deposits In a Novel Murine Model of AA Amyloidosis," Amyloid 12(3):149-156.

* cited by examiner

SAP FC FUSION PROTEINS AND METHODS OF USE

CROSS-REFERENCE TO RELATED APPLICATIONS

This application claims priority to U.S. Provisional Application No. 63/108,799, filed on Nov. 2, 2020, and U.S. Provisional Application No. 63/153,777, filed Feb. 25, 2021, the contents of each of which are incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165992000200SEQLIST.TXT, date recorded: Oct. 28, 2021, size: 91,399 bytes)

FIELD

The present invention relates to SAP-Fc fusion proteins and methods of treating amyloid-related disorders by administering SAP-Fc fusion proteins.

BACKGROUND

Amyloidosis, is a broad group of diseases that belong to the group of conformational protein diseases that include other diseases such as Alzheimer's disease, transmissible spongiform encephalopathies, Huntington's disease, or diabetes mellitus type II.

Amyloidosis is a rare disease characterized by the presence of insoluble protein deposits with abnormal fibrillar conformation in tissues. Most often, it is fragments of serum precursor proteins that are the cause. Many organs can be affected by these extracellular deposits, called "amyloid substance". The main organs affected by amyloid deposits are the kidney, the heart, the digestive tract, the liver, the skin, the peripheral nerve and the eye. The organs affected by this disease usually have a considerable volume. Ultimately, amyloidosis can affect all organs as well as the central nervous system so that there are many very varied symptoms.

Various approaches for treating amyloidosis have been tried. For example, chemotherapy treatment by administration of glucocorticoids (dexamethasone) and antimitotics. The efficacy of new anti-inflammatory drugs (anti-TNF, anti-IL1) is currently being evaluated clinically. But for the moment, this amyloidosis remains incurable and fatal, since there is no specific treatment that can eliminate deposits more quickly. DMSO and colchicine, as well as I-Dox anthracycline have also been tried.

Anti-SAP antibodies are another therapeutic being developed for amyloidsis. EOD001 is a monoclonal antibody, which specifically targets amyloid amyloid AL or AA. WO2015063728 discloses SAP-Fc antibody fusions for treating amyloidosis.

Accordingly, there is a need for effective treatments for amyloidosis and amyloid-related diseases.

BRIEF SUMMARY

In one aspect, provided herein is a fusion protein comprising a first polypeptide and a second polypeptide, wherein the first polypeptide comprises a human serum amyloid P (SAP) component protein linked to the N-terminus of a first human Fc domain, wherein the second polypeptide comprises a second human Fc domain but does not comprise a human SAP component protein, wherein the first and the second Fc domains form a dimer, and wherein the one of the two Fc domains comprises a knob mutation and the other Fc domain comprises a hole mutation. In some embodiments, the first polypeptide comprises a knob mutation and the second polypeptide comprises a hole mutation. In some embodiments, the first polypeptide comprises the amino acid sequence set forth in SEQ ID NO:5, SEQ ID NO:7, SEQ ID NO: 8, or SEQ ID NO: 10 and the second polypeptide comprises the amino acid sequence set forth in SEQ ID NO:6 or SEQ ID NO:9. In some embodiments, the first polypeptide comprises a hole mutation and the second polypeptide comprises a knob mutation. In some embodiments, the first polypeptide comprises the amino acid sequence set forth in SEQ ID NO: 11, SEQ ID NO: 13, SEQ ID NO: 14, or SEQ ID NO: 16 and the second polypeptide comprises the amino acid sequence set forth in SEQ ID NO: 12 or SEQ ID NO: 15. In some embodiments, the human serum amyloid P component protein comprises an amino acid substitution at position N32 or N110 according to SEQ ID NO:17. In some embodiments, the human serum amyloid P component protein comprises the amino acid sequence set forth in SEQ ID NO. 20. In some embodiments, the first and second Fc domain comprises an amino acid substitution at position C226 or C229 according to EU numbering. In some embodiments, the first and second Fc domain comprises amino acid substitutions C226S or C229S, according to EU numbering. In some embodiments, the first and second Fc domain comprises an amino acid substitution at amino acid position 11 or 14, numbering according to the amino acid sequence of SEQ ID NO: 18. In some embodiments, the first and second Fc domain comprises a serine residue at amino acid position 11 or 14, numbering according to the amino acid sequence of SEQ ID NO: 18. In some embodiments, the first and second Fc domain comprises the amino acid sequence set forth in SEQ ID NO: 18. In some embodiments, the first or second Fc domain comprises a mutation that reduces FcRn binding. In some embodiments, the fusion protein forms a pentamer.

In another aspect, provided herein is a fusion protein comprising a structure represented by the following formula, from N-terminus to C-terminus, SAP-hinge1-Fc1-L1-hinge2-Fc2, wherein SAP is a human serum amyloid P (SAP) component protein, hinge1 is a first hinge sequence, Fc1 is a first Fc domain sequence, L1 is a linker, hinge 2 is a second hinge sequence, and Fc2 is a second Fc domain sequence. In some embodiments, the fusion protein comprises the amino acid sequence set forth in SEQ ID NO: 1, SEQ ID NO: 2, SEQ ID NO: 3, or SEQ ID NO: 4. In some embodiments, the human serum amyloid P component protein comprises an amino acid substitution at position N32 or N110 according to SEQ ID NO:17. In some embodiments, the human serum amyloid P component protein comprises the amino acid sequence set forth in SEQ ID NO. 20. In some embodiments, the first and second Fc domain comprises an amino acid substitution at position C226 or C229 according to EU numbering. In some embodiments, the first and second Fc domain comprises amino acid substitutions C226S or C229S, according to EU numbering. In some embodiments, the first and second Fc domain comprises an amino acid substitution at amino acid position 11 or 14, numbering according to the amino acid sequence of SEQ ID NO: 18. In some embodiments, the first and second Fc domain comprises a serine residue at amino acid position 11 or 14, numbering according to the amino acid sequence of SEQ ID NO: 18. In some embodiments, the first and second Fc domain comprises the amino acid sequence set forth in SEQ ID NO: 18. In some embodiments, the first or second Fc domain comprises a mutation that reduces FcRn binding. In some embodiments, the fusion protein forms a pentamer.

In another aspect, provided herein is a pharmaceutical composition comprising a fusion protein described herein.

In another aspect, provided herein is nucleic acid encoding a fusion protein described herein.

In another aspect, provided herein is a host cell comprising a nucleic acid described herein.

In another aspect, provided herein is a method of producing a fusion protein described herein, comprising culturing a host cell comprising nucleic acid encoding the fusion protein under conditions to express the fusion protein. In some embodiments, the host cell is a CHO cell or a 293 cell. In some embodiments, the host cell does not glycosylate the SAP component protein.

In another aspect, provided herein is a method of treating an amyloid disease comprising administering a fusion protein described herein to an individual in need thereof. In some embodiments, the amyloid disease comprises systemic amyloidosis.

In another aspect, provided herein is a fusion protein comprising a structure represented by the following formula, from N-terminus to C-terminus, hinge1-Fc1-L1-hinge2-Fc2, wherein hinge1 is a first hinge sequence, Fc1 is a first Fc domain sequence, L1 is a linker, hinge 2 is a second hinge sequence, and Fc2 is a second Fc domain sequence, wherein the first and second Fc domain comprises amino acid substitutions C226S or C229S according to EU numbering, and/or wherein the first and second Fc domain comprises a serine residue at amino acid position 11 or 14, numbering according to the amino acid sequence of SEQ ID NO: 18.

BRIEF DESCRIPTION OF THE FIGURES

FIG. 6A shows SDS-PAGE analysis of reduced and non-reduced SAP-Fc after Protein A affinity purification step. FIG. 6B shows SDS-PAGE analysis of reduced and non-reduced SAP-Fc after a 1700 ml size-exclusion chromatography (SEC) purification step.

FIG. 12A shows a comparison of SAP-Fc 146 biodistribution in AA mice versus wild type (WT) mice. FIG. 12B shows a comparison of SAP-Fc 147 biodistribution in AA mice versus wild type (WT) mice.

FIG. 16A lane 1 is TNT 146 under non-reducing conditions, lane 2 is TNT 151 under non-reducing conditions, lane 3 is TNT 155 under non-reducing conditions, lane 4 is TNT 146 under reducing conditions, lane 5 is TNT 151 under reducing conditions, lane 6 is TNT 155 under reducing conditions. FIG. 16B lane a is TNT 147 under non-reducing conditions, lane 2bis TNT 148 under non-reducing conditions, lane c is TNT 160 under non-reducing conditions, lane d is TNT 147 under reducing conditions, lane e is TNT 148 under reducing conditions, and lane f is TNT 160 in reducing conditions.

FIG. 17A shows change in pHrodo red fluorescence (mean±SD) in mice with TNT 146 amyloid and control mice. FIG. 17B is a plot showing the increase in pHrodo red emission at day 1 in TNT 146 treated amyloid.

FIG. 18A show the results for control mice. FIG. 18B shows the results for mice treated with an SAP-Fc fusion protein.

DETAILED DESCRIPTION

Figure 1:
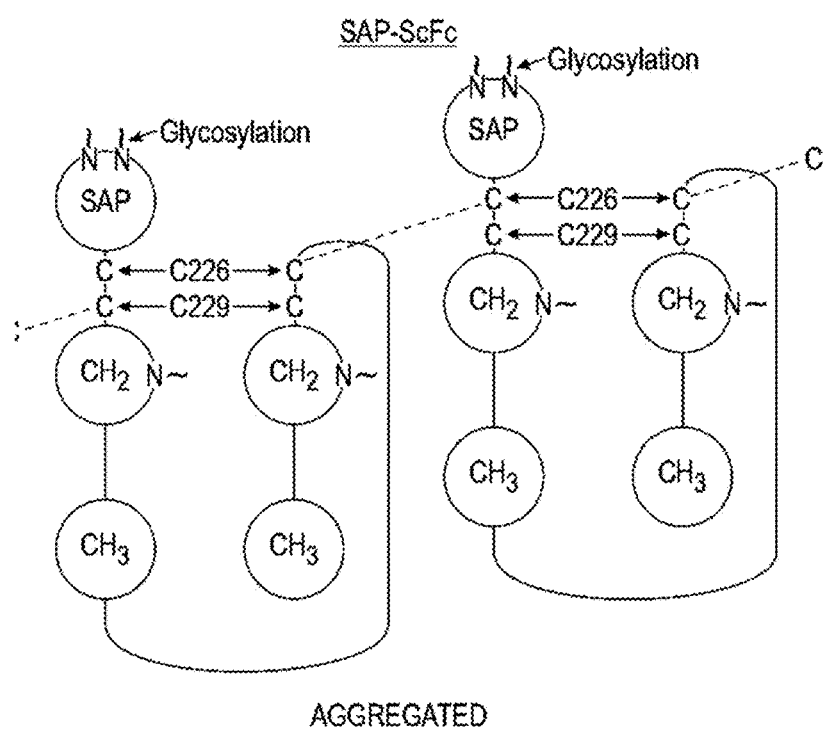
FIG. 1 shows an SAP-scFc construct.
Figure 2A:
FIG. 2A shows a deglycosylated SAP mutant.
Figure 2B:
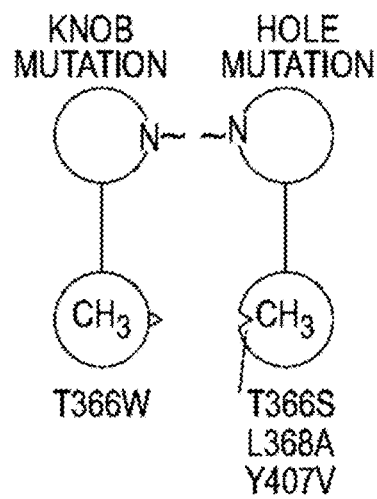
FIG. 2B shows a knob and hole Fc region.
Figure 2C:
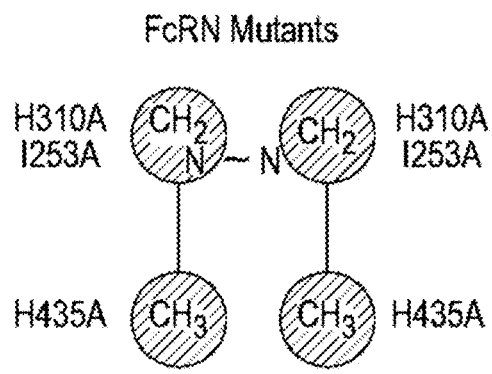
FIG. 2C shows an Fc with FcRN mutations.

Provided herein are SAP-Fc fusion proteins which are able to bind to amyloids with high affinity and induce phagocytosis. In some embodiments, the SAP-Fc fusion proteins have one or modifications which promote dimerization in the Fc region. In some embodiments, the SAP-Fc fusion proteins have increased stability as compared to SAP-Fc fusions. In some embodiments, the SAP-Fc fusion proteins form stable non-covalent pentamers. In some embodiments, the SAP-Fc fusion proteins form stable non-covalent decamers. In some embodiments, the SAP-Fc fusion proteins provided here have reduced aggregation.

SAP-Fc Fusion Proteins

TABLE 1

Sequences of components of SAP-Fc fusions.

| Description | Sequence | SEQ ID NO |
|---|---|---|
| IgG1 Fc (hole) | EPKSSDKTHTCPPCPAPELLGGPSVFLFPPKPKDTL MISRTPEVTCVVVDVSHEDPEVKFNWYVDGVEVH NAKTKPREEQYNSTYRVVSVLTVLHQDWLNGKE YKCKVSNKALPAPIEKTISKAKGQPREPQVYTLPPS REEMTKNQVSLSCAVKGFYPSDIAVEWESNGQPE NNYKTTPPVLDSDGSFFLVSKLTVDKSRWQQGNV FSCSVMHEALHNHYTQKSLSLSPGK | 6 |
| IgG1 Fc (hole; FcRn KO) | EPKSSDKTHTCPPCPAPELLGGPSVFLFPPKPKDTL MASRTPEVTCVVVDVSHEDPEVKFNWYVDGVEV HNAKTKPREEQYNSTYRVVSVLTVLAQDWLNGK EYKCKVSNKALPAPIEKTISKAKGQPREPQVYTLPP SREEMTKNQVSLSCAVKGFYPSDIAVEWESNGQPE NNYKTTPPVLDSDGSFFLVSKLTVDKSRWQQGNV FSCSVMHEALHNAYTQKSLSLSPGK | 9 |
| IgG1 Fc (knob) | EPKSSDKTHTCPPCPAPELLGGPSVFLFPPKPKDTL MISRTPEVTCVVVDVSHEDPEVKFNWYVDGVEVH NAKTKPREEQYNSTYRVVSVLTVLHQDWLNGKE YKCKVSNKALPAPIEKTISKAKGQPREPQVYTLPPS REEMTKNQVSLWCLVKGFYPSDIAVEWESNGQPE NNYKTTPPVLDSDGSFFLYSKLTVDKSRWQQGNV FSCSVMHEALHNHYTQKSLSLSPGK | 12 |
| IgG1 Fc (knob; FcRn KO) | EPKSSDKTHTCPPCPAPELLGGPSVFLFPPKPKDTL MASRTPEVTCVVVDVSHEDPEVKFNWYVDGVEV HNAKTKPREEQYNSTYRVVSVLTVLAQDWLNGK EYKCKVSNKALPAPIEKTISKAKGQPREPQVYTLPP SREEMTKNQVSLWCLVKGFYPSDIAVEWESNGQP ENNYKTTPPVLDSDGSFFLYSKLTVDKSRWQQGN VFSCSVMHEALHNAYTQKSLSLSPGK | 15 |
| SAP | HTDLSGKVFVFPRESVTDHVNLITPLEKPLQNFTLC FRAYSDLSRAYSLFSYNTQGRDNELLVYKERVGE YSLYIGRHKVTSKVIEKFPAPVHICVSWESSSGIAEF WINGTPLVKKGLRQGYFVEAQPKIVLGQEQDSYG GKFDRSQSFVGEIGDLYMWDSVLPPENILSAYQGT PLPANILDWQALNYEIRGYVIIKPLVWV | 17 |
| HingeM IgG1 Fc | EPKSSDKTHTSPPSPAPELLGGPSVFLFPPKPKDTL MISRTPEVTCVVVDVSHEDPEVKFNWYVDGVEVH NAKTKPREEQYNSTYRVVSVLTVLHQDWLNGKE | 18 |

TABLE 1-continued

Sequences of components of SAP-Fc fusions.

| Description | Sequence | SEQ ID NO |
|---|---|---|
| | YKCKVSNKALPAPIEKTISKAKGQPREPQVYTLPPS<br>REEMTKNQVSLTCLVKGFYPSDIAVEWESNGQPE<br>NNYKTTPPVLDSDGSFFLYSKLTVDKSRWQQGNV<br>FSCSVMHEALHNHYTQKSLSLSPGK | |
| GS linker | GGGGSGGGGSGGGGS | 19 |
| SAP (degly N32S, N110S) | HTDLSGKVFVFPRESVTDHVNLITPLEKPLQSFTLC<br>FRAYSDLSRAYSLFSYNTQGRDNELLVYKERVGE<br>YSLYIGRHKVTSKVIEKFPAPVHICVSWESSSGIAEF<br>WISGTPLVKKGLRQGYFVEAQPKIVLGQEQDSYG<br>GKFDRSQSFVGEIGDLYMWDSVLPPENILSAYQGT<br>PLPANILDWQALNYEIRGYVIIKPLVWV | 20 |
| HingeM IgG1 Fc (FcRn KO) | EPKSSDKTHTSPPSPAPELLGGPSVFLFPPKPKDTL<br>MASRTPEVTCVVVDVSHEDPEVKFNWYVDGVEV<br>HNAKTKPREEQYNSTYRVVSVLTVLAQDWLNGK<br>EYKCKVSNKALPAPIEKTISKAKGQPREPQVYTLPP<br>SREEMTKNQVSLTCLVKGFYPSDIAVEWESNGQPE<br>NNYKTTPPVLDSDGSFFLYSKLTVDKSRWQQGNV<br>FSCSVMHEALHNAYTQKSLSLSPGK | 21 |

TABLE 2

SAP-Fc fusion sequences.

| Description | Sequence | SEQ ID NO |
|---|---|---|
| TNT146<br>SAP-HingeM<br>IgG1 Fc-GS<br>linker-HingeM<br>IgG1 Fc | HTDLSGKVFVFPRESVTDHVNLITPLEKPLQNFTLC<br>FRAYSDLSRAYSLFSYNTQGRDNELLVYKERVGE<br>YSLYIGRHKVTSKVIEKFPAPVHICVSWESSSGIAEF<br>WINGTPLVKKGLRQGYFVEAQPKIVLGQEQDSYG<br>GKFDRSQSFVGEIGDLYMWDSVLPPENILSAYQGT<br>PLPANILDWQALNYEIRGYVIIKPLVWVEPKSSDKT<br>HTSPPSPAPELLGGPSVFLFPPKPKDTLMISRTPEVT<br>CVVVDVSHEDPEVKFNWYVDGVEVHNAKTKPRE<br>EQYNSTYRVVSVLTVLHQDWLNGKEYKCKVSNK<br>ALPAPIEKTISKAKGQPREPQVYTLPPSREEMTKNQ<br>VSLTCLVKGFYPSDIAVEWESNGQPENNYKTTPPV<br>LDSDGSFFLYSKLTVDKSRWQQGNVFSCSVMHEA<br>LHNHYTQKSLSLSPGKGGGGSGGGGSGGGGSEPK<br>SSDKTHTSPPSPAPELLGGPSVFLFPPKPKDTLMISR<br>TPEVTCVVVDVSHEDPEVKFNWYVDGVEVHNAK<br>TKPREEQYNSTYRVVSVLTVLHQDWLNGKEYKC<br>KVSNKALPAPIEKTISKAKGQPREPQVYTLPPSREE<br>MTKNQVSLTCLVKGFYPSDIAVEWESNGQPENNY<br>KTTPPVLDSDGSFFLYSKLTVDKSRWQQGNVFSCS<br>VMHEALHNHYTQKSLSLSPGK | 1 |
| TNT151<br>SAP (degly<br>N32S, N110S)-<br>HingeM IgG1 Fc-<br>GS linker-<br>HingeM IgG1 Fc | HTDLSGKVFVFPRESVTDHVNLITPLEKPLQSFTLC<br>FRAYSDLSRAYSLFSYNTQGRDNELLVYKERVGE<br>YSLYIGRHKVTSKVIEKFPAPVHICVSWESSSGIAEF<br>WISGTPLVKKGLRQGYFVEAQPKIVLGQEQDSYG<br>GKFDRSQSFVGEIGDLYMWDSVLPPENILSAYQGT<br>PLPANILDWQALNYEIRGYVIIKPLVWVEPKSSDKT<br>HTSPPSPAPELLGGPSVFLFPPKPKDTLMISRTPEVT<br>CVVVDVSHEDPEVKFNWYVDGVEVHNAKTKPRE<br>EQYNSTYRVVSVLTVLHQDWLNGKEYKCKVSNK<br>ALPAPIEKTISKAKGQPREPQVYTLPPSREEMTKNQ<br>VSLTCLVKGFYPSDIAVEWESNGQPENNYKTTPPV<br>LDSDGSFFLYSKLTVDKSRWQQGNVFSCSVMHEA<br>LHNHYTQKSLSLSPGKGGGGSGGGGSGGGGSEPK<br>SSDKTHTSPPSPAPELLGGPSVFLFPPKPKDTLMISR<br>TPEVTCVVVDVSHEDPEVKFNWYVDGVEVHNAK<br>TKPREEQYNSTYRVVSVLTVLHQDWLNGKEYKC<br>KVSNKALPAPIEKTISKAKGQPREPQVYTLPPSREE<br>MTKNQVSLTCLVKGFYPSDIAVEWESNGQPENNY<br>KTTPPVLDSDGSFFLYSKLTVDKSRWQQGNVFSCS<br>VMHEALHNHYTQKSLSLSPGK | 2 |
| TNT155<br>(TNT146- FcRn<br>KO) | HTDLSGKVFVFPRESVTDHVNLITPLEKPLQNFTLC<br>FRAYSDLSRAYSLFSYNTQGRDNELLVYKERVGE<br>YSLYIGRHKVTSKVIEKFPAPVHICVSWESSSGIAEF | 3 |

TABLE 2-continued

SAP-Fc fusion sequences.

| Description | Sequence | SEQ ID NO |
|---|---|---|
| SAP-HingeM IgG1 Fc (FcRn KO)-GS linker-HingeM IgG1 Fc (FcRn KO) | WINGTPLVKKGLRQGYFVEAQPKIVLGQEQDSYG GKFDRSQSFVGEIGDLYMWDSVLPPENILSAYQGT PLPANILDWQALNYEIRGYVIIKPLVWVEPKSSDKT HTSPPSPAPELLGGPSVFLFPPKPKDTLMASRTPEV TCVVVDVSHEDPEVKFNWYVDGVEVHNAKTKPR EEQYNSTYRVVSVLTVLAQDWLNGKEYKCKVSN KALPAPIEKTISKAKGQPREPQVYTLPPSREEMTKN QVSLTCLVKGFYPSDIAVEWESNGQPENNYKTTPP VLDSDGSFFLYSKLTVDKSRWQQGNVFSCSVMHE ALHNAYTQKSLSLSPGKGGGGSGGGGSGGGGSEP KSSDKTHTSPPSPAPELLGGPSVFLFPPKPKDTLMA SRTPEVTCVVVDVSHEDPEVKFNWYVDGVEVHN AKTKPREEQYNSTYRVVSVLTVLAQDWLNGKEY KCKVSNKALPAPIEKTISKAKGQPREPQVYTLPPSR EEMTKNQVSLTCLVKGFYPSDIAVEWESNGQPEN NYKTTPPVLDSDGSFFLYSKLTVDKSRWQQGNVF SCSVMHEALHNAYTQKSLSLSPGK | |
| TNT156 (TNT151- FcRn KO) SAP (degly N32S, N110S)-HingeM IgG1 Fc (FcRn KO)-GS linker-HingeM IgG1 Fc (FcRn KO) | HTDLSGKVFVFPRESVTDHVNLITPLEKPLQSFTLC FRAYSDLSRAYSLFSYNTQGRDNELLVYKERVGE YSLYIGRHKVTSKVIEKFPAPVHICVSWESSSGIAEF WISGTPLVKKGLRQGYFVEAQPKIVLGQEQDSYG GKFDRSQSFVGEIGDLYMWDSVLPPENILSAYQGT PLPANILDWQALNYEIRGYVIIKPLVWVEPKSSDKT HTSPPSPAPELLGGPSVFLFPPKPKDTLMASRTPEV TCVVVDVSHEDPEVKFNWYVDGVEVHNAKTKPR EEQYNSTYRVVSVLTVLAQDWLNGKEYKCKVSN KALPAPIEKTISKAKGQPREPQVYTLPPSREEMTKN QVSLTCLVKGFYPSDIAVEWESNGQPENNYKTTPP VLDSDGSFFLYSKLTVDKSRWQQGNVFSCSVMHE ALHNAYTQKSLSLSPGKGGGGSGGGGSGGGGSEP KSSDKTHTSPPSPAPELLGGPSVFLFPPKPKDTLMA SRTPEVTCVVVDVSHEDPEVKFNWYVDGVEVHN AKTKPREEQYNSTYRVVSVLTVLAQDWLNGKEY KCKVSNKALPAPIEKTISKAKGQPREPQVYTLPPSR EEMTKNQVSLTCLVKGFYPSDIAVEWESNGQPEN NYKTTPPVLDSDGSFFLYSKLTVDKSRWQQGNVF SCSVMHEALHNAYTQKSLSLSPGK | 4 |
| TNT148 Polypeptide 1: SAP-IgG1 Fc (knob) | HTDLSGKVFVFPRESVTDHVNLITPLEKPLQNFTLC FRAYSDLSRAYSLFSYNTQGRDNELLVYKERVGE YSLYIGRHKVTSKVIEKFPAPVHICVSWESSSGIAEF WINGTPLVKKGLRQGYFVEAQPKIVLGQEQDSYG GKFDRSQSFVGEIGDLYMWDSVLPPENILSAYQGT PLPANILDWQALNYEIRGYVIIKPLVWVEPKSSDKT HTCPPCPAPELLGGPSVFLFPPKPKDTLMISRTPEVT CVVVDVSHEDPEVKFNWYVDGVEVHNAKTKPRE EQYNSTYRVVSVLTVLHQDWLNGKEYKCKVSNK ALPAPIEKTISKAKGQPREPQVYTLPPSREEMTKNQ VSLWCLVKGFYPSDIAVEWESNGQPENNYKTTPP VLDSDGSFFLYSKLTVDKSRWQQGNVFSCSVMHE ALHNHYTQKSLSLSPGK | 5 |
| TNT148 Polypeptide 2: Stumpy IgG1 Fc (hole) | EPKSSDKTHTCPPCPAPELLGGPSVFLFPPKPKDTL MISRTPEVTCVVVDVSHEDPEVKFNWYVDGVEVH NAKTKPREEQYNSTYRVVSVLTVLHQDWLNGKE YKCKVSNKALPAPIEKTISKAKGQPREPQVYTLPPS REEMTKNQVSLSCAVKGFYPSDIAVEWESNGQPE NNYKTTPPVLDSDGSFFLVSKLTVDKSRWQQGNV FSCSVMHEALHNHYTQKSLSLSPGK | 6 |
| TNT152 Polypeptide 1: SAP (degly N32S, N110S)-IgG1 Fc (knob) | HTDLSGKVFVFPRESVTDHVNLITPLEKPLQSFTLC FRAYSDLSRAYSLFSYNTQGRDNELLVYKERVGE YSLYIGRHKVTSKVIEKFPAPVHICVSWESSSGIAEF WISGTPLVKKGLRQGYFVEAQPKIVLGQEQDSYG GKFDRSQSFVGEIGDLYMVVDSVLPPENILSAYQGT PLPANILDWQALNYEIRGYVIIKPLVWVEPKSSDKT HTCPPCPAPELLGGPSVFLFPPKPKDTLMISRTPEVT CVVVDVSHEDPEVKFNWYVDGVEVHNAKTKPRE EQYNSTYRVVSVLTVLHQDWLNGKEYKCKVSNK ALPAPIEKTISKAKGQPREPQVYTLPPSREEMTKNQ VSLWCLVKGFYPSDIAVEWESNGQPENNYKTTPP VLDSDGSFFLYSKLTVDKSRWQQGNVFSCSVMHE ALHNHYTQKSLSLSPGK | 7 |

TABLE 2-continued

SAP-Fc fusion sequences.

| Description | Sequence | SEQ ID NO |
|---|---|---|
| TNT152 Polypeptide 2: Stumpy IgG1 Fc (hole) | EPKSSDKTHTCPPCPAPELLGGPSVFLFPPKPKDTL MISRTPEVTCVVVDVSHEDPEVKFNWYVDGVEVH NAKTKPREEQYNSTYRVVSVLTVLHQDWLNGKE YKCKVSNKALPAPIEKTISKAKGQPREPQVYTLPPS REEMTKNQVSLSCAVKGFYPSDIAVEWESNGQPE NNYKTTPPVLDSDGSFFLVSKLTVDKSRWQQGNV FSCSVMHEALHNHYTQKSLSLSPGK | 6 |
| TNT157 (TNT148- FcRn KO) Polypeptide 1: SAP-IgG1 Fc (knob; FcRn KO) | HTDLSGKVFVFPRESVTDHVNLITPLEKPLQNFTLC FRAYSDLSRAYSLFSYNTQGRDNELLVYKERVGE YSLYIGRHKVTSKVIEKFPAPVHICVSWESSSGIAEF WINGTPLVKKGLRQGYFVEAQPKIVLGQEQDSYG GKFDRSQSFVGEIGDLYMVVDSVLPPENILSAYQGT PLPANILDWQALNYEIRGYVIIKPLVWVEPKSSDKT HTCPPCPAPELLGGPSVFLFPPKPKDTLMASRTPEV TCVVVDVSHEDPEVKFNWYVDGVEVHNAKTKPR EEQYNSTYRVVSVLTVLAQDWLNGKEYKCKVSN KALPAPIEKTISKAKGQPREPQVYTLPPSREEMTKN QVSLWCLVKGFYPSDIAVEWESNGQPENNYKTTP PVLDSDGSFFLYSKLTVDKSRWQQGNVFSCSVMH EALHNAYTQKSLSLSPGK | 8 |
| TNT157 (TNT148- FcRn KO) Polypeptide 2: Stumpy IgG1 Fc (hole; FcRn KO) | EPKSSDKTHTCPPCPAPELLGGPSVFLFPPKPKDTL MASRTPEVTCVVVDVSHEDPEVKFNWYVDGVEV HNAKTKPREEQYNSTYRVVSVLTVLAQDWLNGK EYKCKVSNKALPAPIEKTISKAKGQPREPQVYTLPP SREEMTKNQVSLSCAVKGFYPSDIAVEWESNGQPE NNYKTTPPVLDSDGSFFLVSKLTVDKSRWQQGNV FSCSVMHEALHNAYTQKSLSLSPGK | 9 |
| TNT158 (TNT152 - FcRn KO) Polypeptide 1: SAP (degly N32S, N110S)- IgG1 Fc (knob; FcRn KO) | HTDLSGKVFVFPRESVTDHVNLITPLEKPLQSFTLC FRAYSDLSRAYSLFSYNTQGRDNELLVYKERVGE YSLYIGRHKVTSKVIEKFPAPVHICVSWESSSGIAEF WISGTPLVKKGLRQGYFVEAQPKIVLGQEQDSYG GKFDRSQSFVGEIGDLYMWDSVLPPENILSAYQGT PLPANILDWQALNYEIRGYVIIKPLVWVEPKSSDKT HTCPPCPAPELLGGPSVFLFPPKPKDTLMASRTPEV TCVVVDVSHEDPEVKFNWYVDGVEVHNAKTKPR EEQYNSTYRVVSVLTVLAQDWLNGKEYKCKVSN KALPAPIEKTISKAKGQPREPQVYTLPPSREEMTKN QVSLWCLVKGFYPSDIAVEWESNGQPENNYKTTP PVLDSDGSFFLYSKLTVDKSRWQQGNVFSCSVMH EALHNAYTQKSLSLSPGK | 10 |
| TNT158 (TNT152 - FcRn KO) Polypeptide 2: Stumpy-IgG1 Fc (hole; FcRn KO) | EPKSSDKTHTCPPCPAPELLGGPSVFLFPPKPKDTL MASRTPEVTCVVVDVSHEDPEVKFNWYVDGVEV HNAKTKPREEQYNSTYRVVSVLTVLAQDWLNGK EYKCKVSNKALPAPIEKTISKAKGQPREPQVYTLPP SREEMTKNQVSLSCAVKGFYPSDIAVEWESNGQPE NNYKTTPPVLDSDGSFFLVSKLTVDKSRWQQGNV FSCSVMHEALHNAYTQKSLSLSPGK | 9 |
| TNT147 Polypeptide 1: SAP-IgG1 Fc (hole) | HTDLSGKVFVFPRESVTDHVNLITPLEKPLQNFTLC FRAYSDLSRAYSLFSYNTQGRDNELLVYKERVGE YSLYIGRHKVTSKVIEKFPAPVHICVSWESSSGIAEF WINGTPLVKKGLRQGYFVEAQPKIVLGQEQDSYG GKFDRSQSFVGEIGDLYMWDSVLPPENILSAYQGT PLPANILDWQALNYEIRGYVIIKPLVWVEPKSSDKT HTCPPCPAPELLGGPSVFLFPPKPKDTLMISRTPEVT CVVVDVSHEDPEVKFNWYVDGVEVHNAKTKPRE EQYNSTYRVVSVLTVLHQDWLNGKEYKCKVSNK ALPAPIEKTISKAKGQPREPQVYTLPPSREEMTKNQ VSLSCAVKGFYPSDIAVEWESNGQPENNYKTTPPV LDSDGSFFLVSKLTVDKSRWQQGNVFSCSVMHEA LHNHYTQKSLSLSPGK | 11 |
| TNT147 Polypeptide 2: Stumpy IgG1 Fc (knob) | EPKSSDKTHTCPPCPAPELLGGPSVFLFPPKPKDTL MISRTPEVTCVVVDVSHEDPEVKFNWYVDGVEVH NAKTKPREEQYNSTYRVVSVLTVLHQDWLNGKE FcYKCKVSNKALPAPIEKTISKAKGQPREPQVYTLPPS REEMTKNQVSLWCLVKGFYPSDIAVEWESNGQPE NNYKTTPPVLDSDGSFFLVSKLTVDKSRWQQGNV FSCSVMHEALHNHYTQKSLSLSPGK | 12 |

TABLE 2-continued

SAP-Fc fusion sequences.

| Description | Sequence | SEQ ID NO |
|---|---|---|
| TNT159<br>(TNT147 degly)<br>Polypeptide 1:<br>SAP (degly N32S<br>and N110S)-IgG1<br>Fc (hole) | HTDLSGKVFVFPRESVTDHVNLITPLEKPLQSFTLC<br>FRAYSDLSRAYSLFSYNTQGRDNELLVYKERVGE<br>YSLYIGRHKVTSKVIEKFPAPVHICVSWESSSGIAEF<br>WISGTPLVKKGLRQGYFVEAQPKIVLGQEQDSYG<br>GKFDRSQSFVGEIGDLYMWDSVLPPENILSAYQGT<br>PLPANILDWQALNYEIRGYVIIKPLVWVEPKSSDKT<br>HTCPPCPAPELLGGPSVFLFPPKPKDTLMISRTPEVT<br>CVVVDVSHEDPEVKFNWYVDGVEVHNAKTKPRE<br>EQYNSTYRVVSVLTVLHQDWLNGKEYKCKVSNK<br>ALPAPIEKTISKAKGQPREPQVYTLPPSREEMTKNQ<br>VSLSCAVKGFYPSDIAVEWESNGQPENNYKTTPPV<br>LDSDGSFFLVSKLTVDKSRWQQGNVFSCSVMHEA<br>LHNHYTQKSLSLSPGK | 13 |
| TNT159<br>(TNT147 degly)<br>Polypeptide 2:<br>Stumpy IgG1 Fc<br>(knob) | EPKSSDKTHTCPPCPAPELLGGPSVFLFPPKPKDTL<br>MISRTPEVTCVVVDVSHEDPEVKFNWYVDGVEVH<br>NAKTKPREEQYNSTYRVVSVLTVLHQDWLNGKE<br>YKCKVSNKALPAPIEKTISKAKGQPREPQVYTLPPS<br>REEMTKNQVSLWCLVKGFYPSDIAVEWESNGQPE<br>NNYKTTPPVLDSDGSFFLYSKLTVDKSRWQQGNV<br>FSCSVMHEALHNHYTQKSLSLSPGK | 12 |
| TNT160<br>(TNT147- FcRn<br>KO)<br>Polypeptide 1:<br>SAP-IgG1 Fc<br>(hole; FcRn KO) | HTDLSGKVFVFPRESVTDHVNLITPLEKPLQNFTLC<br>FRAYSDLSRAYSLFSYNTQGRDNELLVYKERVGE<br>YSLYIGRHKVTSKVIEKFPAPVHICVSWESSSGIAEF<br>WINGTPLVKKGLRQGYFVEAQPKIVLGQEQDSYG<br>GKFDRSQSFVGEIGDLYMWDSVLPPENILSAYQGT<br>PLPANILDWQALNYEIRGYVIIKPLVWVEPKSSDKT<br>HTCPPCPAPELLGGPSVFLFPPKPKDTLMASRTPEV<br>TCVVVDVSHEDPEVKFNWYVDGVEVHNAKTKPR<br>EEQYNSTYRVVSVLTVLAQDWLNGKEYKCKVSN<br>KALPAPIEKTISKAKGQPREPQVYTLPPSREEMTKN<br>QVSLSCAVKGFYPSDIAVEWESNGQPENNYKTTPP<br>VLDSDGSFFLVSKLTVDKSRWQQGNVFSCSVMHE<br>ALHNAYTQKSLSLSPGK | 14 |
| TNT160<br>(TNT147- FcRn<br>KO)<br>Polypeptide 2:<br>Stumpy IgG1 Fc<br>(knob; FcRn KO) | EPKSSDKTHTCPPCPAPELLGGPSVFLFPPKPKDTL<br>MASRTPEVTCVVVDVSHEDPEVKFNWYVDGVEV<br>HNAKTKPREEQYNSTYRVVSVLTVLAQDWLNGK<br>EYKCKVSNKALPAPIEKTISKAKGQPREPQVYTLPP<br>SREEMTKNQVSLWCLVKGFYPSDIAVEWESNGQP<br>ENNYKTTPPVLDSDGSFFLYSKLTVDKSRWQQGN<br>VFSCSVMHEALHNAYTQKSLSLSPGK | 15 |
| TNT161<br>(TNT147 degly-<br>FcRn KO)<br>Polypeptide 1:<br>SAP (degly N32S<br>and N110S)-IgG1<br>Fc (hole; FcRn<br>KO) | HTDLSGKVFVFPRESVTDHVNLITPLEKPLQSFTLC<br>FRAYSDLSRAYSLFSYNTQGRDNELLVYKERVGE<br>YSLYIGRHKVTSKVIEKFPAPVHICVSWESSSGIAEF<br>WISGTPLVKKGLRQGYFVEAQPKIVLGQEQDSYG<br>GKFDRSQSFVGEIGDLYMWDSVLPPENILSAYQGT<br>PLPANILDWQALNYEIRGYVIIKPLVWVEPKSSDKT<br>HTCPPCPAPELLGGPSVFLFPPKPKDTLMASRTPEV<br>TCVVVDVSHEDPEVKFNWYVDGVEVHNAKTKPR<br>EEQYNSTYRVVSVLTVLAQDWLNGKEYKCKVSN<br>KALPAPIEKTISKAKGQPREPQVYTLPPSREEMTKN<br>QVSLSCAVKGFYPSDIAVEWESNGQPENNYKTTPP<br>VLDSDGSFFLVSKLTVDKSRWQQGNVFSCSVMHE<br>ALHNAYTQKSLSLSPGK | 16 |
| TNT161<br>(TNT147 degly-<br>FcRn KO)<br>Polypeptide 2:<br>Stumpy IgG1 Fc<br>(knob; FcRn KO) | EPKSSDKTHTCPPCPAPELLGGPSVFLFPPKPKDTL<br>MASRTPEVTCVVVDVSHEDPEVKFNWYVDGVEV<br>HNAKTKPREEQYNSTYRVVSVLTVLAQDWLNGK<br>EYKCKVSNKALPAPIEKTISKAKGQPREPQVYTLPP<br>SREEMTKNQVSLWCLVKGFYPSDIAVEWESNGQP<br>ENNYKTTPPVLDSDGSFFLYSKLTVDKSRWQQGN<br>VFSCSVMHEALHNAYTQKSLSLSPGK | 15 |
| SAP-scFc | HTDLSGKVFVFPRESVTDHVNLITPLEKPLQ<br>NFTLCFRAYSDLSRAYSLFSYNTQGRDNEL<br>LVYKERVGEYSLYIGRHKVTSKVIEKFPAP<br>VHICVSWESSSGIAEFWINGTPLVKKGLRQ<br>GYFVEAQPKIVLGQEQDSYGGKFDRSQSFV<br>GEIGDLYMWDSVLPPENILSAYQGTPLPAN<br>ILDWQALNYEIRGYVIIKPLVWVEPKSSDK<br>THTCPPCPAPELLGGPSVFLFPPKPKDTLM<br>ISRTPEVTCVVVDVSHEDPEVKFNWYVDGV | 22 |

TABLE 2-continued

SAP-Fc fusion sequences.

| Description | Sequence | SEQ ID NO |
|---|---|---|
| | EVHNAKTKPREEQYNSTYRVVSVLTVLHQD<br>WLNGKEYKCKVSNKALPAPIEKTISKAKGQ<br>PREPQVYTLPPSREEMTKNQVSLTCLVKGF<br>YPSDIAVEWESNGQPENNYKTTPPVLDSDG<br>SFFLYSKLTVDKSRWQQGNVFSCSVMHEAL<br>HNHYTQKSLSLSPGKGGGGSGGGGSGGGGS<br>EPKSSDKTHTCPPCPAPELLGGPSVFLFPP<br>KPKDTLMISRTPEVTCVVVDVSHEDPEVKF<br>NWYVDGVEVH<br>NAKTKPREEQYNSTYRVVSVLTVLHQDWLN<br>GKEYKCKVSNKALPAPIEKTISKAKGQPRE<br>PQVYTLPPSREEMTKNQVSLTCLVKGFYPS<br>DIAVEWESNGQPENNYKTTPPVLDSDGSFF<br>LYSKLTVDKSRWQQGNVFSCSVMHEALHNH<br>YTQKSLSLSPGK | |
| TNT170<br>(TNT146 Fc1<br>FCRN KO)<br>SAP-(IgG1-Fc-<br>HingeM) FcRn<br>mutant-GS<br>linker-(IgG1-Fc-<br>HingeM) | HTDLSGKVFVFPRESVTDHVNLITPLEKPLQNFTLC<br>FRAYSDLSRAYSLFSYNTQGRDNELLVYKERVGE<br>YSLYIGRHKVTSKVIEKFPAPVHICVSWESSSGIAEF<br>WINGTPLVKKGLRQGYFVEAQPKIVLGQEQDSYG<br>GKFDRSQSFVGEIGDLYMWDSVLPPENILSAYQGT<br>PLPANILDWQALNYEIRGYVIIKPLVWVEPKSSDKT<br>HTSPPSPAPELLGGPSVFLFPPKPKDTLMASRTPEV<br>TCVVVDVSHEDPEVKFNWYVDGVEVHNAKTKPR<br>EEQYNSTYRVVSVLTVLAQDWLNGKEYKCKVSN<br>KALPAPIEKTISKAKGQPREPQVYTLPPSREEMTKN<br>QVSLTCLVKGFYPSDIAVEWESNGQPENNYKTTPP<br>VLDSDGSFFLYSKLTVDKSRWQQGNVFSCSVMHE<br>ALHNAYTQKSLSLSPGKGGGGSGGGGSGGGGSEP<br>KSSDKTHTSPPSPAPELLGGPSVFLFPPKPKDTLMIS<br>RTPEVTCVVVDVSHEDPEVKFNWYVDGVEVHNA<br>KTKPREEQYNSTYRVVSVLTVLHQDWLNGKEYK<br>CKVSNKALPAPIEKTISKAKGQPREPQVYTLPPSRE<br>EMTKNQVSLTCLVKGFYPSDIAVEWESNGQPENN<br>YKTTPPVLDSDGSFFLYSKLTVDKSRWQQGNVFSC<br>SVMHEALHNHYTQKSLSLSPGK | 23 |
| TNT171<br>(TNT146 Fc2<br>FCRN KO)<br>SAP-(IgG1-Fc-<br>HingeM)-GS<br>linker-(IgG1-Fc-<br>HingeM) FcRn<br>mutant | HTDLSGKVFVFPRESVTDHVNLITPLEKPLQNFTLC<br>FRAYSDLSRAYSLFSYNTQGRDNELLVYKERVGE<br>YSLYIGRHKVTSKVIEKFPAPVHICVSWESSSGIAEF<br>WINGTPLVKKGLRQGYFVEAQPKIVLGQEQDSYG<br>GKFDRSQSFVGEIGDLYMWDSVLPPENILSAYQGT<br>PLPANILDWQALNYEIRGYVIIKPLVWVEPKSSDKT<br>HTSPPSPAPELLGGPSVFLFPPKPKDTLMISRTPEVT<br>CVVVDVSHEDPEVKFNWYVDGVEVHNAKTKPRE<br>EQYNSTYRVVSVLTVLHQDWLNGKEYKCKVSNK<br>ALPAPIEKTISKAKGQPREPQVYTLPPSREEMTKNQ<br>VSLTCLVKGFYPSDIAVEWESNGQPENNYKTTPPV<br>LDSDGSFFLYSKLTVDKSRWQQGNVFSCSVMHEA<br>LHNHYTQKSLSLSPGKGGGGSGGGGSGGGGSEPK<br>SSDKTHTSPPSPAPELLGGPSVFLFPPKPKDTLMAS<br>RTPEVTCVVVDVSHEDPEVKFNWYVDGVEVHNA<br>KTKPREEQYNSTYRVVSVLTVLAQDWLNGKEYK<br>CKVSNKALPAPIEKTISKAKGQPREPQVYTLPPSRE<br>EMTKNQVSLTCLVKGFYPSDIAVEWESNGQPENN<br>YKTTPPVLDSDGSFFLYSKLTVDKSRWQQGNVFSC<br>SVMHEALHNAYTQKSLSLSPGK | 24 |
| TNT146A<br>TNT146 with<br>leader sequences | MPLLLLLPLLWAGALAHTDLSGKVFVFPRESVTD<br>HVNLITPLEKPLQNFTLCFRAYSDLSRAYSLFSYNT<br>QGRDNELLVYKERVGEYSLYIGRHKVTSKVIEKFP<br>APVHICVSWESSSGIAEFWINGTPLVKKGLRQGYF<br>VEAQPKIVLGQEQDSYGGKFDRSQSFVGEIGDLYM<br>WDSVLPPENILSAYQGTPLPANILDWQALNYEIRG<br>YVIIKPLVWVEPKSSDKTHTSPPSPAPELLGGPSVF<br>LFPPKPKDTLMISRTPEVTCVVVDVSHEDPEVKFN<br>WYVDGVEVHNAKTKPREEQYNSTYRVVSVLTVL<br>HQDWLNGKEYKCKVSNKALPAPIEKTISKAKGQP<br>REPQVYTLPPSREEMTKNQVSLTCLVKGFYPSDIA<br>VEWESNGQPENNYKTTPPVLDSDGSFFLYSKLTVD<br>KSRWQQGNVFSCSVMHEALHNYTQKSLSLSPGK<br>GGGGSGGGGSGGGGSEPKSSDKTHTSPPSPAPELL<br>GGPSVFLFPPKPKDTLMISRTPEVTCVVVDVSHEDP<br>EVKFNVVYVDGVEVHNAKTKPREEQYNSTYRVVS<br>VLTVLHQDWLNGKEYKCKVSNKALPAPIEKTISK<br>AKGQPREPQVYTLPPSREEMTKNQVSLTCLVKGF | 25 |

TABLE 2-continued

SAP-Fc fusion sequences.

| Description | Sequence | SEQ ID NO |
|---|---|---|
| | YPSDIAVEWESNGQPENNYKTTPPVLDSDGSFFLY SKLTVDKSRWQQGNVFSCSVMHEALHNHYTQKS LSLSPGK** | |

TABLE 3

SAP-Fc fusion construct descriptions.

Figure 3A:
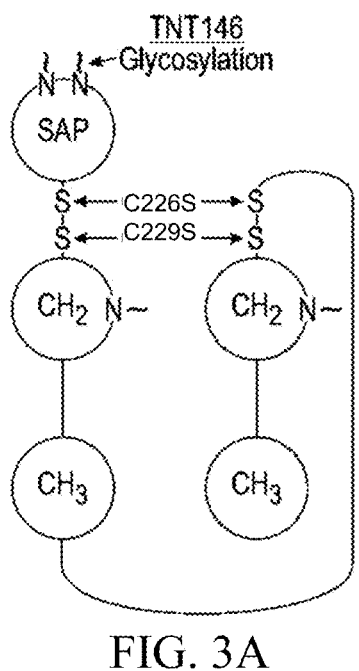
FIG. 3A shows SAP-scFc construct TNT 146.
Figure 3B:
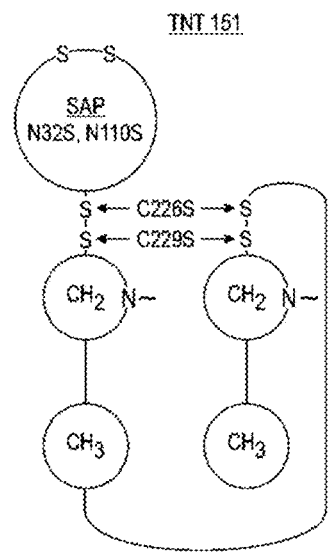
FIG. 3B shows SAP-scFc construct TNT 151.
Figure 3C:
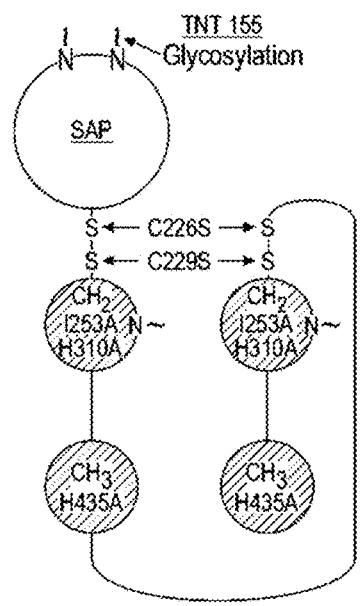
FIG. 3C shows SAP-scFc construct TNT 155.
Figure 3D:
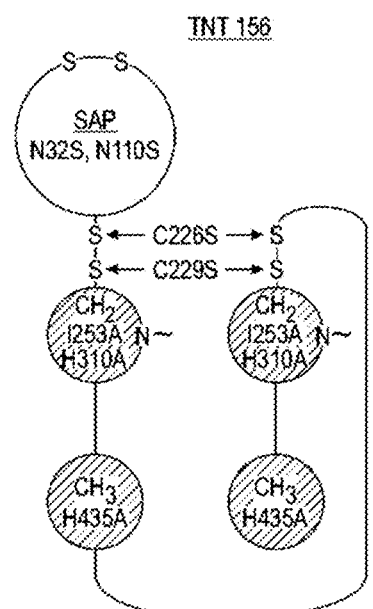
FIG. 3D shows SAP-scFc construct TNT 156.
Figure 4A:
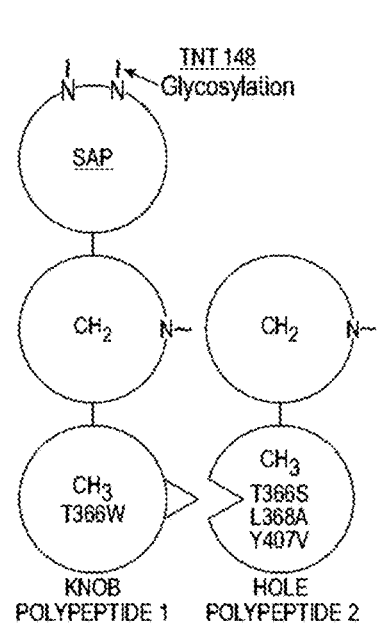
FIG. 4A shows SAP-Fc construct TNT 148.
Figure 4B:
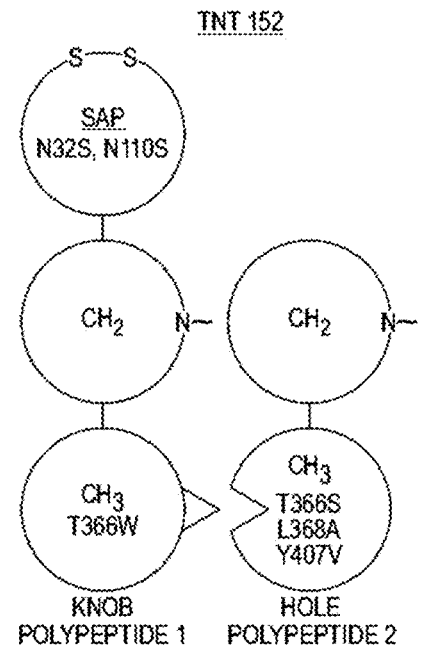
FIG. 4B shows SAP-Fc construct TNT 152.
Figure 4C:
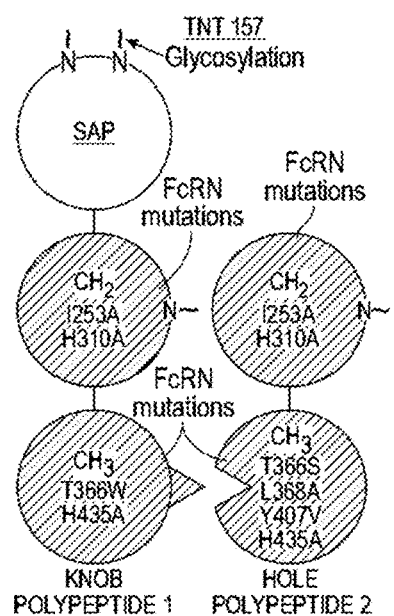
FIG. 4C shows SAP-Fc construct TNT 157.
Figure 4D:
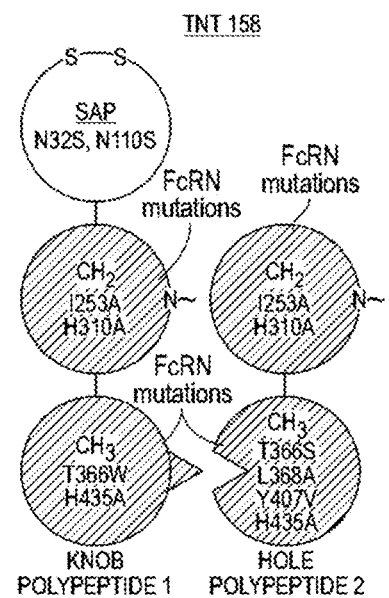
FIG. 4D shows SAP-Fc construct TNT 158.
Figure 5A:
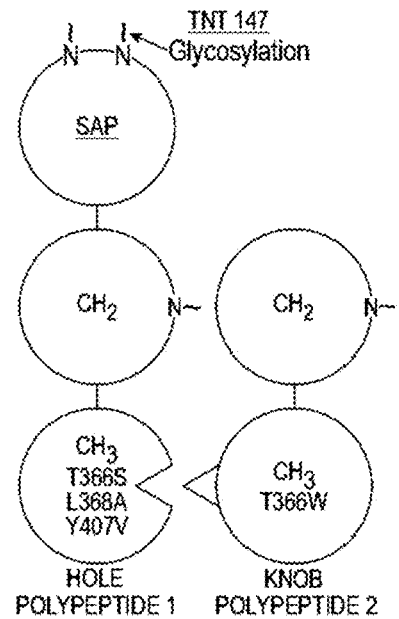
FIG. 5A shows SAP-Fc construct TNT 147.
Figure 5B:
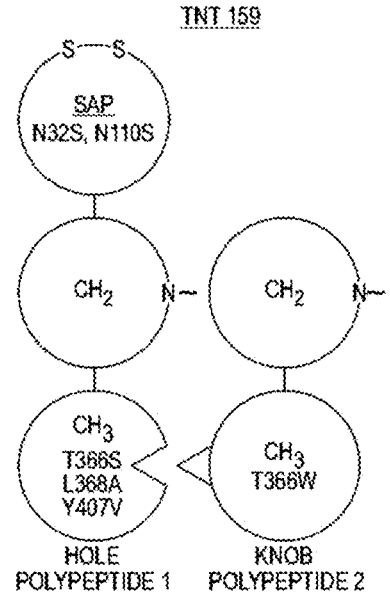
FIG. 5B shows SAP-Fc construct TNT 159.
Figure 5C:
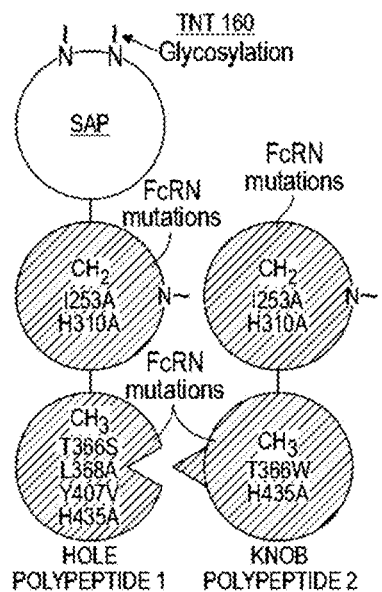
FIG. 5C shows SAP-Fc construct TNT 160.
Figure 5D:
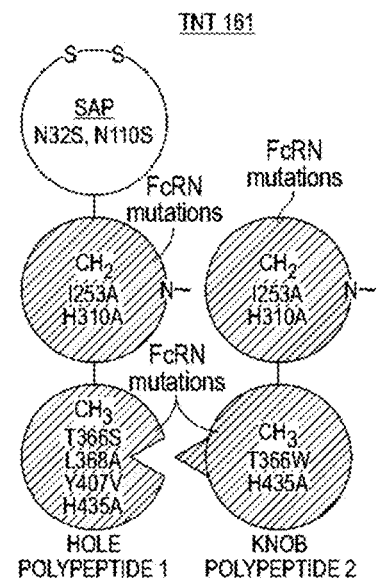
FIG. 5D shows SAP-Fc construct TNT 161.

| Construct | Description | SEQ ID | FIG. |
|---|---|---|---|
| TNT146 | Single chain SAP-Fc fusion protein with hinge cysteine mutations. SAP-hinge (C226S/C229S) - IgG1 Fc - linker - hinge (C226S/C229S) - IgG1 Fc | 1 | FIG. 3A |
| TNT151 | Single chain SAP-Fc fusion protein with hinge cysteine mutations and degylcosylated SAP. SAP (N32S/N110S) - hinge (C226S/C229S) - IgG1 Fc - linker - hinge (C226S/C229S) - IgG1 Fc | 2 | FIG. 3B |
| TNT155 | Single chain SAP-Fc fusion protein with hinge cysteine mutations and reduced FcRn binding. SAP-hinge (C226S/C229S) - IgG1 Fc (I253A/H310A/H435A) - linker - hinge (C226S/C229S) - IgG1 Fc (I253A/H310A/H435A) | 3 | FIG. 3C |
| TNT156 | Single chain SAP-Fc fusion protein with hinge cysteine mutations, reduced FcRn binding and degylcosylated SAP. SAP (N32S/N110S) - hinge (C22S6S/C229S) - IgG1 Fc (I253A/H310A/H435A) - linker - hinge (C226S/C229S) - IgG1 Fc (I253A/H310A/H435A) | 4 | FIG. 3D |
| TNT148 | Polypeptide 1: SAP-IgG1 Fc (Knob) Polypeptide 2: IgG1Fc (Hole) Polypeptide 1: SAP-IgG1 Fc (T366W) Polypeptide 2: IgG1 Fc (T366S/L368A/Y407V) | 5, 6 | FIG. 4A |
| TNT152 | Polypeptide 1: Deglycosylated SAP-IgG1Fc (Knob) Polypeptide 2: IgG1Fc (Hole) Polypeptide 1: SAP (N32S/N110S)-IgG1 Fc (T366W) Polypeptide 2: IgG1 Fc (T366S/L368A/Y407V) | 7, 6 | FIG. 4B |
| TNT157 | Polypeptide 1: SAP-IgG1 Fc (Knob, Reduced FcRn binding) Polypeptide 2: IgG1Fc (Hole, Reduced FcRN binding) Polypeptide 1: SAP - IgG1 Fc (I253A/H310A/T366W/H435A) Polypeptide 2: IgG1 Fc (I253A/H310A/T366S/L368A/Y407V/H435A) | 8, 9 | FIG. 4C |
| TNT158 | Polypeptide 1: Deglycosylated SAP-IgG1Fc (Knob, Reduced FcRn binding) Polypeptide 2: IgG1Fc (Hole, Reduced FcRn binding) Polypeptide 1: SAP (N325/N110S)-IgG1 Fc (I253A/H310A/T366W/H435A) Polypeptide 2: IgG1 Fc (I253A/H310A/T366S/L368A/Y407V/H435A) | 10, 9 | FIG. 4D |
| TNT147 | Polypeptide 1: SAP- IgG1Fc (Hole) Polypeptide 2: IgG1 Fc (Knob) Polypeptide 1: SAP - IgG1 Fc (T366S/L368A/Y407V) Polypeptide 2: IgG1 Fc (T366W) | 11, 12 | FIG. 5A |
| TNT159 | Polypeptide 1: SAP (Deglycosylated) - IgG1Fc (Hole) Polypeptide 2: IgG1 Fc (Knob) Polypeptide 1: SAP (N32S/N110S) - IgG1 Fc (T55S/L368A/Y407V) Polypeptide 2: IgG1 Fc (T366W) | 13, 12 | FIG. 5B |
| TNT160 | Polypeptide 1: SAP- IgG1Fc (Hole, Reduced FcRn binding) Polypeptide 2: IgG1 Fc (Knob, Reduced FcRn binding) Polypeptide 1: SAP - IgG1 Fc (I253A/H310A/T366S/L368A/Y407V/H435A) Polypeptide 2: IgG1 Fc (I253A/H310A/T366W/H435A) | 14, 15 | FIG. 5C |
| TNT161 | Polypeptide 1: SAP (Deglycosylated) - IgG1Fc (Hole, Reduced FcRn binding) Polypeptide 2: IgG1 Fc (Knob, Reduced FcRn binding) Polypeptide 1: SAP (N32S/N110S) - IgG1 Fc (I253A/H310A/T366S/L368A/Y407V/H435A) Polypeptide 2: IgG1 Fc (I253A/H310A/T366W/H435A) | 16, 15 | FIG. 5D |

TABLE 3-continued

SAP-Fc fusion construct descriptions.

| Construct | Description | SEQ ID | FIG. |
|---|---|---|---|
| TNT170 | Single chain SAP-Fc fusion protein with hinge cysteine mutations and Reduced FcRn binding in first Fc. SAP-hinge (C2265/C2295) - IgG1 Fc (I253A/H310A/H435A) - linker - hinge (C226S/C229S) - IgG1 Fc | 23 | |
| TNT171 | Single chain SAP-Fc fusion protein with hinge cysteine mutations and Reduced FcRn binding in second Fc. SAP-hinge (C226S/C229S) - IgG1 Fc - linker - hinge (C226S/C229S) - IgG1 Fc (I253A/H310A/H435A) | 24 | |

Provided herein are SAP-Fc fusion proteins comprising, from N-terminus to C-terminus, an SAP component protein, a first Fc domain comprising a first hinge sequence, a linker peptide, and a second Fc domain comprising a second hinge sequence.

In some embodiments, the hinge sequence is an antibody hinge sequence. In some embodiments, the hinge sequences is a human antibody hinge sequence. In some embodiments, the hinge sequence is an IgG1, IgG2, or an IgG4 antibody hinge sequence. In some embodiments the hinge sequence is a human IgG1 antibody hinge sequence. In some embodiments, the hinge sequence is a human IgG1 antibody hinge sequence with one or more amino acid substitutions. In some embodiments, the hinge sequence is a human IgG1 antibody hinge sequence, wherein one or more cysteine residues are substituted. In some embodiments, the hinge sequence is a human IgG1 antibody hinge sequence, wherein one or more cysteine residues are substituted to serine.

In some embodiments, the SAP component protein is a human SAP protein. In some embodiments, the human SAP protein comprises the amino acid sequence of SEQ ID NO: 17. In some embodiments, the human SAP protein comprises one or more modifications that decrease glycosylation of the SAP protein. In some embodiments, the one or more modifications that decrease glycosylation of the SAP protein are selected from an N32S and an N110S amino acid substitution, numbering starting from the N-terminus of the SAP protein. In some embodiments, the human SAP protein comprises amino acid substitutions N32S and N110S, numbering starting from the N-terminus of the SAP protein. In some embodiments, the human SAP protein comprises the amino acid sequence of SEQ ID NO: 20.

In some embodiments, the first Fc domain comprising a first hinge sequence comprises a human IgG1 Fc domain. In some embodiments, the first Fc domain comprising a first hinge sequence comprises one or more modifications that remove cysteine residues in the hinge region. In some embodiments, the modification that removes a cysteine residue in the hinge region increases stability of heterodimeric SAP-Fc fusion protein. In some embodiments, the modification prevents higher order covalent multimerization.

Cysteine residues, e.g., within the hinge region of an Fc domain, can cause protein aggregation due to the formation of intermolecular disulfide bonds between cysteine residues on different Fc regions. Accordingly, in some embodiments, the SAP-Fc fusion proteins provided herein comprise an Fc domain comprising one or more modifications that remove cysteine residues in the hinge region, thus preventing or reducing aggregation of the SAP-Fc fusion proteins caused by intermolecular pairing of cysteine residues. In some embodiments, the one or more modifications that remove cysteine residues in the hinge region are at position C226 or C229 according to EU numbering. In some embodiments, the substitution is selected from a C226S and a C229S amino acid substitution, numbering based on the EU numbering system. In some embodiments, the Fc domain comprising a first hinge sequence comprises a C226S and a C229S amino acid substitution, numbering based on the EU numbering system. In some embodiments, the first and second Fc domains both comprises a substitution in the hinge region at position C226 or position C229. In some embodiments, the substitution is selected from a serine residue at amino acid position 11 according to the numbering of SEQ ID NO: 18 and a serine residue at amino acid position 14 according to the numbering of SEQ ID NO: 18. In some embodiments, the Fc domain comprising a first hinge sequence comprises a serine residue at amino acid position 11 and a serine residue at amino acid position 14 according to the numbering of SEQ ID NO: 18. In some embodiments, the first and second Fc domains both comprise a serine residue at amino acid position 11 and a serine residue at amino acid position 14 according to the numbering of SEQ ID NO: 18. In some embodiments, the Fc domain comprising a hinge sequence comprises the amino acid sequence of SEQ ID NO: 18.

In some embodiments, the Fc domain comprising a hinge sequence comprises one or more modifications that reduce FcRn binding. In some embodiments, the one or more modifications that reduce FcRn binding are at position I253, H310, or H435, numbering according to the EU system. In some embodiments, the modification comprises one or more of I253A, H310A, and H435A amino acid substitutions, numbering based on the EU numbering system. In some embodiments, the Fc domain comprising a hinge sequence comprises amino acid substitutions I253A, H310A, and H435A, numbering based on the EU numbering system. In some embodiments, the one or more modifications that reduce FcRn binding are at amino acid position 38, 95, or 220 according to numbering of SEQ ID NO: 9. In some embodiments, the modification comprises an alanine residue at one or more of amino acid position 38, 95, and 220 according to numbering of SEQ ID NO: 9. In some embodiments, the Fc domain comprising a hinge sequence comprises an alanine residue at amino acid position 38, 95, and 220 according to numbering of SEQ ID NO: 9. In some embodiments, the first and second Fc domains each comprise substitutions at amino acid position 38, 95, or 220 according to numbering of SEQ ID NO: 9. In some embodiments, Fc domain comprising a first hinge sequence comprises the amino acid sequence of SEQ ID NO: 9, 15, or 21. In some embodiments, the first and second Fc domains each comprise substitutions at position I253, H310, or H435, numbering based on the EU numbering system.

In some embodiments, the SAP-Fc fusion protein further comprises a linker. In some embodiments, the linker connects the C-terminus of the first Fc region to the N-terminus of the second Fc region. In some embodiments, the linker connects the C-terminus of the first Fc region to the hinge region of the second Fc. In some embodiments, the linker peptide comprises a glycine-serine linker sequence. In some embodiments, the liker peptide comprises a (G4S)$_n$ sequence. In some embodiments n=1-10. In some embodiments, the linker peptide comprises the amino acid sequence of SEQ ID NO: 19.

In some embodiments, the Fc domain comprising a hinge sequence comprises one or more modifications to remove a cysteine in the hinge region and one or more modifications that reduce FcRn binding. In some embodiments, the one or more modifications that remove cysteine residues in the hinge region are selected from a C226S and a C229S amino acid substitution, numbering based on the EU numbering system. In some embodiments, the one or more modifications that remove cysteine residues in the hinge region are selected from a serine residue at amino acid position 11 according to the numbering of SEQ ID NO: 18 and a serine residue at amino acid position 14 according to the numbering of SEQ ID NO: 18. In some embodiments, the second Fc domain comprising a second hinge sequence comprises one or more modifications that reduce FcRn binding. In some embodiments, the one or more modifications that reduce FcRn binding are selected from an I253A, H310A, and H435A amino acid substitution, numbering based on the EU numbering system. In some embodiments, the Fc domain comprises a hinge sequence comprises amino acid substitutions I253A, H310A, and H435A, numbering based on the EU numbering system. In some embodiments, the one or more modifications that reduce FcRn binding are an alanine residue at amino acid position selected from 38, 95, and 220 according to numbering of SEQ ID NO: 9. In some embodiments, the Fc domain comprising a hinge sequence comprises an alanine residue at amino acid position 38, 95, and 220 according to numbering of SEQ ID NO: 9. In some embodiments, the Fc domain comprising a hinge sequence comprises the amino acid sequence of SEQ ID NO: 21.

In some embodiments, the SAP-Fc fusion protein is a single chain polypeptide. In some embodiments, the SAP-Fc fusion comprises a single chain Fc. In some embodiments, the SAP-Fc fusion protein comprises, from N-terminus to C-terminus, an SAP component protein, a first Fc domain comprising a first hinge sequence, a linker peptide, and a second Fc domain comprising a second hinge sequence. In some embodiments, the SAP component protein comprises the amino acid sequence of SEQ ID NO: 17. In some embodiments, the first Fc domain comprising a first hinge sequence comprises the amino acid sequence of SEQ ID NO: 18. In some embodiments, the linker peptide comprises the amino acid sequence of SEQ ID NO: 19. In some embodiments, the second Fc domain comprising a second hinge sequence comprises the amino acid sequence of SEQ ID NO: 18. In some embodiments, the SAP-Fc fusion protein comprises the amino acid sequence of SEQ ID NO: 1.

In some embodiments, the SAP-Fc fusion protein comprises, from N-terminus to C-terminus, an SAP component protein comprising one or more modifications that decrease glycosylation of the SAP component protein, a first Fc domain comprising a first hinge sequence, a linker peptide, and a second Fc domain comprising a second hinge sequence. In some embodiments, the SAP component protein comprises the amino acid sequence of SEQ ID NO: 20, the first Fc domain comprising a first hinge sequence comprises the amino acid sequence of SEQ ID NO: 18, the linker peptide comprises the amino acid sequence of SEQ ID NO: 19, and the second Fc domain comprising a second hinge sequence comprises the amino acid sequence of SEQ ID NO: 18. In some embodiments, the SAP-Fc fusion protein comprises the amino acid sequence of SEQ ID NO: 2.

In some embodiments, the SAP-Fc fusion protein comprises, from N-terminus to C-terminus, an SAP component protein, a first Fc domain comprising a first hinge sequence and one or more modifications that reduce FcRn binding, a linker peptide, and a second Fc domain comprising a second hinge sequence. In some embodiments, the SAP component protein comprises the amino acid sequence of SEQ ID NO: 17, the first Fc domain comprising a first hinge sequence and one or more modifications that reduce FcRn binding comprises the amino acid sequence of SEQ ID NO: 21, the linker peptide comprises the amino acid sequence of SEQ ID NO: 19, and the second Fc domain comprising a second hinge sequence comprises the amino acid sequence of SEQ ID NO: 18. In some embodiments, the SAP-Fc fusion protein comprises the amino acid sequence of SEQ ID NO: 23.

In some embodiments, the SAP-Fc fusion protein comprises, from N-terminus to C-terminus, an SAP component protein, a first Fc domain comprising a first hinge sequence, a linker peptide, and a second Fc domain comprising a second hinge sequence and one or more modifications that reduce FcRn binding. In some embodiments, the SAP component protein comprises the amino acid sequence of SEQ ID NO: 17, the first Fc domain comprising a first hinge sequence comprises the amino acid sequence of SEQ ID NO: 18, the linker peptide comprises the amino acid sequence of SEQ ID NO: 19, and the second Fc domain comprising a second hinge sequence and one or more modifications that reduce FcRn binding comprises the amino acid sequence of SEQ ID NO: 21. In some embodiments, the SAP-Fc fusion protein comprises the amino acid sequence of SEQ ID NO: 24.

In some embodiments, the SAP-Fc fusion protein comprises, from N-terminus to C-terminus, an SAP component protein, a first Fc domain comprising a first hinge sequence and one or more modifications that reduce FcRn binding, a linker peptide, and a second Fc domain comprising a second hinge sequence and one or more modifications that reduce FcRn binding. In some embodiments, the SAP component protein comprises the amino acid sequence of SEQ ID NO: 17, the first Fc domain comprising a first hinge sequence and one or more modifications that reduce FcRn binding comprises the amino acid sequence of SEQ ID NO: 21, the linker peptide comprises the amino acid sequence of SEQ ID NO: 19, and the second Fc domain comprising a second hinge sequence and one or more modifications that reduce FcRn binding comprises the amino acid sequence of SEQ ID NO: 21. In some embodiments, the SAP-Fc fusion protein comprises the amino acid sequence of SEQ ID NO: 3.

In some embodiments, the SAP-Fc fusion protein comprises, from N-terminus to C-terminus, an SAP component protein comprising one or more modifications that decrease glycosylation of the SAP component protein, a first Fc domain comprising a first hinge sequence and one or more modifications that reduce FcRn binding, a linker peptide, and a second Fc domain comprising a second hinge sequence and one or more modifications that reduce FcRn binding. In some embodiments, the SAP component protein comprising one or more modifications that decrease glycosylation of the SAP component protein comprises the amino acid sequence of SEQ ID NO: 20, the first Fc domain comprising a first hinge sequence and one or more modifications that reduce FcRn binding comprises the amino acid sequence of SEQ ID NO: 21, the linker peptide comprises the amino acid sequence of SEQ ID NO: 19, and the second Fc domain comprising a second hinge sequence and one or more modifications that reduce FcRn binding comprises the amino acid sequence of SEQ ID NO: 21. In some embodiments, the SAP-Fc fusion protein comprises the amino acid sequence of SEQ ID NO: 4.

Also provided herein are SAP-Fc fusion proteins comprising a first polypeptide and a second polypeptide, wherein the first polypeptide comprises a human SAP component protein linked to the N-terminus of a first human Fc domain, wherein the second polypeptide comprises a second human Fc domain but does not comprise a human SAP component protein, wherein the first and the second Fc domain form a dimer, and wherein one of the two Fc domains comprises one or more knob mutations and the other Fc domain comprises one or more hole mutations.

In some embodiments, the human SAP component protein comprises the amino acid sequence of SEQ ID NO: 17. In some embodiments, the human SAP component protein comprises one or more modifications that decrease glycosylation of the SAP component protein. In some embodiments, the one or more modifications that decrease glycosylation of the SAP component protein are selected from an N32S and an N110S amino acid substitution, numbering starting from the N-terminus of the SAP component protein. In some embodiments, the human SAP component protein comprises amino acid substitutions N32S and N110S, numbering starting from the N-terminus of the SAP component protein. In some embodiments, the human SAP component protein comprises the amino acid sequence of SEQ ID NO: 20.

In some embodiments, the SAP-Fc fusion protein comprises one or more modifications to promote heterodimerization of the Fc domain. In some embodiments, one of the two Fc domains comprises one or more knob mutations and the other Fc domain comprises one or more hole mutations, wherein the knob and hole mutations promote association of the first and the second Fc domain, e.g., in a dimer. In some embodiments, the Fc domain comprising the one or more knob mutations comprises a T366W amino acid substitution, and the Fc domain comprising one or more hole mutations comprises amino acid substitutions T366S, L368A, and Y407V, numbering based on the EU numbering system. In some embodiments, the Fc domain comprising one or more knob mutations comprises a T366W and a Y349C amino acid substitution, and the Fc domain comprising the one or more hole mutations comprises amino acid substitutions S354C, T366S, L368A, and Y407V, numbering based on the EU numbering system. In some embodiments, the Fc domain comprising one or more knob mutations comprises a T366W and a Y349C amino acid substitution, and the Fc domain comprising one or more hole mutations comprises amino acid substitutions E356C, T366S, L368A, and Y407V, numbering based on the EU numbering system. In some embodiments, the Fc domain comprising one or more knob mutations comprises a R409D and a K370E amino acid substitution, and the Fc domain comprising one or more hole mutations comprises amino acid substitutions D399K and E357K, numbering based on the EU numbering system. In some embodiments, the Fc domain comprising one or more knob mutations comprises amino acid substitutions T366W, R409D, and K370E, and the Fc domain comprising one or more hole mutations comprises amino acid substitutions T366S, L368A, Y407V, D399K and E357K, numbering based on the EU numbering system. In some embodiments, one of the two Fc domains comprises amino acid substitutions Y349C and T366W, and the other Fc domain comprises amino acid substitutions S354C, T366S, L368A, Y407V, numbering based on the EU numbering system. In some embodiments, one of the two Fc domains comprises a T366W amino acid substitution, and the other Fc domain comprises amino acid substitutions T366S, L368A, and Y407V, numbering based on the EU numbering system. In some embodiments, one of the two Fc domains comprises amino acid substitutions Y349C, T366W, R409D, and K370E, and the other Fc domain comprises amino acid substitutions S354C, T366S, L368A, Y407V, D399K, and E357K, numbering based on the EU numbering system. Additional or alternative "knobs-in-holes" technologies that are known in the art may be used in the SAP-Fc fusion proteins of the disclosure, e.g., as described in EP1870459A1. In some embodiments, the Fc domain comprising the one or more knob mutations comprises a tryptophan residue at amino acid position 151 according to numbering of SEQ ID NO: 12, and the Fc domain comprising one or more hole mutations comprises a serine residue at amino acid position 151, an alanine residue at amino acid position 153, and a valine residue at amino acid position 192, wherein the numbering is according to SEQ ID NO: 6.

In some embodiments, the SAP-fc fusion protein comprises a comprising a first polypeptide and a second polypeptide, wherein the first polypeptide comprises a human serum amyloid P (SAP) protein linked to the N-terminus of a first human Fc domain, wherein the second polypeptide comprises a second human Fc domain but does not comprise a human SAP component protein, wherein the first and the second Fc domain forms a dimer, and wherein the one of the two Fc domains comprises a knob mutation and the other Fc domain comprises a hole mutation. In some embodiments, the first human Fc domain comprises a knob mutation. In some embodiments, the knob mutation is a T366W amino acid substitution, numbering based on the EU numbering system. In some embodiments, the knob mutation is a tryptophan residue at amino acid position 151 according to numbering of SEQ ID NO: 12. In some embodiments, the first human Fc domain comprises the amino acid sequence of SEQ ID NO: 12. In some embodiments, the first human Fc domain further comprises one or more modifications that reduce FcRn binding. In some embodiments, the one or more modifications that reduce FcRn binding are selected from an I253A, H310A, and H435A amino acid substitution, numbering based on the EU numbering system. In some embodiments, the first human Fc domain comprises amino acid substitutions I253A, H310A, and H435A, numbering based on the EU numbering system. In some embodiments, the one or more modifications that reduce FcRn binding are an alanine residue at amino acid position selected from 38, 95, and 220 according to numbering of SEQ ID NO: 15. In some embodiments, the first human Fc domain comprises an alanine residue at amino acid position 38, 95, and 220 according to numbering of SEQ ID NO: 15. In some embodiments, the first human Fc domain comprises the amino acid sequence of SEQ ID NO: 15.

In some embodiments, when the first Fc domain comprises a knob mutation, the second human Fc domain comprises one or more hole mutations. In some embodiments, the one or more hole mutations comprise T366S, L368A, and Y407V amino acid substitutions, numbering based on the EU numbering system. In some embodiments, the one or more hole mutations comprise a serine residue at amino acid position 151, an alanine residue at amino acid position 153, and a valine residue at amino acid position 192, wherein the numbering is according to SEQ ID NO: 6. In some embodiments, the second human Fc domain comprises the amino acid sequence of SEQ ID NO: 6. In some embodiments, the second human Fc domain further comprises one or more modifications that reduce FcRn binding. In some embodiments, the one or more modifications that reduce FcRn binding are selected from an I253A, H310A, and H435A amino acid substitution, numbering based on the EU numbering system. In some embodiments, the second human Fc domain comprises amino acid substitutions I253A, H310A, and H435A, numbering based on the EU numbering system. In some embodiments, the one or more modifications that reduce FcRn binding are an alanine residue at amino acid position selected from 38, 95, and 220 according to numbering of SEQ ID NO: 9. In some embodiments, the second human Fc domain comprises an alanine residue at amino acid position 38, 95, and 220 according to numbering of SEQ ID NO: 9. In some embodiments, the second human Fc domain comprises the amino acid sequence of SEQ ID NO: 9.

In some embodiments, the first human Fc domain comprises one or more hole mutations. In some embodiments, the one or more hole mutations comprise T366S, L368A, and Y407V amino acid substitutions, numbering based on the EU numbering system. In some embodiments, the one or more hole mutations comprise a serine residue at amino acid position 151, an alanine residue at amino acid position 153, and a valine residue at amino acid position 192, wherein the numbering is according to SEQ ID NO: 6. In some embodiments, the first human Fc domain comprises the amino acid sequence of SEQ ID NO: 6. In some embodiments, the first human Fc domain further comprises one or more modifications that reduce FcRn binding. In some embodiments, the one or more modifications that reduce FcRn binding are selected from an I253A, H310A, and H435A amino acid substitution, numbering based on the EU numbering system. In some embodiments, the first human Fc domain comprises amino acid substitutions I253A, H310A, and H435A, numbering based on the EU numbering system. In some embodiments, the one or more modifications that reduce FcRn binding are an alanine residue at amino acid position selected from 38, 95, and 220 according to numbering of SEQ ID NO: 9. In some embodiments, the first human Fc domain comprises an alanine residue at amino acid position 38, 95, and 220 according to numbering of SEQ ID NO: 9. In some embodiments, the first human Fc domain comprises the amino acid sequence of SEQ ID NO: 9.

In some embodiments, when the first Fc domain comprises a hole mutation, the second human Fc domain comprises a knob mutation. In some embodiments, the knob mutation is a T366W amino acid substitution, numbering based on the EU numbering system. In some embodiments, the knob mutation is a tryptophan residue at amino acid position 151 according to numbering of SEQ ID NO: 12. In some embodiments, the second human Fc domain comprises the amino acid sequence of SEQ ID NO: 12. In some embodiments, the second human Fc domain further comprises one or more modifications that reduce FcRn binding. In some embodiments, the one or more modifications that reduce FcRn binding are selected from an I253A, H310A, and H435A amino acid substitution, numbering based on the EU numbering system. In some embodiments, the second human Fc domain comprises amino acid substitutions I253A, H310A, and H435A, numbering based on the EU numbering system. In some embodiments, the one or more modifications that reduce FcRn binding are an alanine residue at amino acid position selected from 38, 95, and 220 according to numbering of SEQ ID NO: 15. In some embodiments, the second human Fc domain comprises an alanine residue at amino acid position 38, 95, and 220 according to numbering of SEQ ID NO: 15. In some embodiments, the second human Fc domain comprises the amino acid sequence of SEQ ID NO: 15.

In some embodiments, the SAP-Fc fusion protein comprises a first polypeptide and a second polypeptide, wherein the first polypeptide comprises an SAP component protein linked to the N-terminus of a first human Fc domain, wherein the second polypeptide comprises a second human Fc domain but does not comprise a human SAP component protein, wherein the first and the second Fc domain form a dimer, wherein the first Fc domain comprises one or more knob mutations, and wherein the second Fc domain comprises one or more hole mutations. In some embodiments, the SAP component protein comprises the amino acid sequence of SEQ ID NO: 17, the first Fc domain comprises the amino acid sequence of SEQ ID NO: 12, and the second Fc domain comprises the amino acid sequence of SEQ ID NO: 6. In some embodiments, the first polypeptide comprises the amino acid sequence of SEQ ID NO: 5, and the second polypeptide comprises the amino acid sequence of SEQ ID NO: 6.

In some embodiments, the SAP-Fc fusion protein comprises a first polypeptide and a second polypeptide, wherein the first polypeptide comprises an SAP component protein comprising one or more modifications that decrease glycosylation of the SAP component protein, wherein the SAP component protein is linked to the N-terminus of a first human Fc domain, wherein the second polypeptide comprises a second human Fc domain but does not comprise a human SAP component protein, wherein the first and the second Fc domain form a dimer, wherein the first Fc domain comprises one or more knob mutations, and wherein the second Fc domain comprises one or more hole mutations. In some embodiments, the SAP component protein comprises the amino acid sequence of SEQ ID NO: 20, the first Fc domain comprises the amino acid sequence of SEQ ID NO: 12, and the second Fc domain comprises the amino acid sequence of SEQ ID NO: 6. In some embodiments, the first polypeptide comprises the amino acid sequence of SEQ ID NO: 7, and the second polypeptide comprises the amino acid sequence of SEQ ID NO: 6.

In some embodiments, the SAP-Fc fusion protein comprises a first polypeptide and a second polypeptide, wherein the first polypeptide comprises an SAP component protein linked to the N-terminus of a first human Fc domain comprising one or more modifications that reduce FcRn binding, wherein the second polypeptide comprises a second human Fc domain comprising one or more modifications that reduce FcRn binding but does not comprise a human SAP component protein, wherein the first and the second Fc domain form a dimer, wherein the first Fc domain comprises one or more knob mutations, and wherein the second Fc domain comprises one or more hole mutations. In some embodiments, the SAP component protein comprises the amino acid sequence of SEQ ID NO: 17, the first Fc domain comprises the amino acid sequence of SEQ ID NO: 15, and the second Fc domain comprises the amino acid sequence of SEQ ID NO: 9. In some embodiments, the first polypeptide comprises the amino acid sequence of SEQ ID NO: 8, and the second polypeptide comprises the amino acid sequence of SEQ ID NO: 9.

In some embodiments, the SAP-Fc fusion protein comprises a first polypeptide and a second polypeptide, wherein the first polypeptide comprises an SAP component protein comprising one or more modifications that decrease glycosylation of the SAP component protein, wherein the SAP component protein is linked to the N-terminus of a first human Fc domain comprising one or more modifications that reduce FcRn binding, wherein the second polypeptide comprises a second human Fc domain comprising one or more modifications that reduce FcRn binding but does not comprise a human SAP component protein, wherein the first and the second Fc domain form a dimer, wherein the first Fc domain comprises one or more knob mutations, and wherein the second Fc domain comprises one or more hole mutations. In some embodiments, the SAP component protein comprises one or more modifications that remove a glycosylation site. In some embodiments, the SAP component protein comprises the amino acid sequence of SEQ ID NO: 20, the first human Fc domain comprises the amino acid sequence of SEQ ID NO: 15, and the second human Fc domain comprises the amino acid sequence of SEQ ID NO: 9. In some embodiments, the first polypeptide comprises the amino acid sequence of SEQ ID NO: 10, and the second polypeptide comprises the amino acid sequence of SEQ ID NO: 9.

In some embodiments, the SAP-Fc fusion protein comprises a first polypeptide and a second polypeptide, wherein the first polypeptide comprises an SAP component protein linked to the N-terminus of a first human Fc domain, wherein the second polypeptide comprises a second human Fc domain but does not comprise a human SAP component protein, wherein the first and the second Fc domain form a dimer, wherein the first Fc domain comprises one or more hole mutations, and wherein the second Fc domain comprises one or more knob mutations. In some embodiments, the SAP component protein comprises the amino acid sequence of SEQ ID NO: 17, the first Fc domain comprises the amino acid sequence of SEQ ID NO: 6, and the second Fc domain comprises the amino acid sequence of SEQ ID NO: 12. In some embodiments, the first polypeptide comprises the amino acid sequence of SEQ ID NO: 11, and the second polypeptide comprises the amino acid sequence of SEQ ID NO: 12.

In some embodiments, the SAP-Fc fusion protein comprises a first polypeptide and a second polypeptide, wherein the first polypeptide comprises an SAP component protein comprising one or more modifications that decrease glycosylation of the SAP component protein, wherein the SAP component protein is linked to the N-terminus of a first human Fc domain, wherein the second polypeptide comprises a second human Fc domain but does not comprise a human SAP component protein, wherein the first and the second Fc domain form a dimer, wherein the first Fc domain comprises one or more hole mutations, and wherein the second Fc domain comprises one or more knob mutations. In some embodiments, the SAP component protein comprises the amino acid sequence of SEQ ID NO: 20, the first Fc domain comprises the amino acid sequence of SEQ ID NO: 6, and the second Fc domain comprises the amino acid sequence of SEQ ID NO: 12. In some embodiments, the first polypeptide comprises the amino acid sequence of SEQ ID NO: 13, and the second polypeptide comprises the amino acid sequence of SEQ ID NO: 12.

In some embodiments, the SAP-Fc fusion protein comprises a first polypeptide and a second polypeptide, wherein the first polypeptide comprises an SAP component protein linked to the N-terminus of a first human Fc domain comprising one or more modifications that reduce FcRn binding, wherein the second polypeptide comprises a second human Fc domain comprising one or more modifications that reduce FcRn binding but does not comprise a human SAP component protein, wherein the first and the second Fc domain form a dimer, wherein the first Fc domain comprises one or more hole mutations, and wherein the second Fc domain comprises one or more knob mutations. In some embodiments, the SAP component protein comprises the amino acid sequence of SEQ ID NO: 17, the first Fc domain comprises the amino acid sequence of SEQ ID NO: 9, and the second Fc domain comprises the amino acid sequence of SEQ ID NO: 15. In some embodiments, the first polypeptide comprises the amino acid sequence of SEQ ID NO: 14, and the second polypeptide comprises the amino acid sequence of SEQ ID NO: 15.

In some embodiments, the SAP-Fc fusion protein comprises a first polypeptide and a second polypeptide, wherein the first polypeptide comprises an SAP component protein comprising one or more modifications that decrease glycosylation of the SAP component protein, wherein the SAP component protein is linked to the N-terminus of a first human Fc domain comprising one or more modifications that reduce FcRn binding, wherein the second polypeptide comprises a second human Fc domain comprising one or more modifications that reduce FcRn binding but does not comprise a human SAP component protein, wherein the first and the second Fc domain form a dimer, wherein the first Fc domain comprises one or more hole mutations, and wherein the second Fc domain comprises one or more knob mutations. In some embodiments, the SAP component protein comprises the amino acid sequence of SEQ ID NO: 20, the first Fc domain comprises the amino acid sequence of SEQ ID NO: 9, and the second Fc domain comprises the amino acid sequence of SEQ ID NO: 15. In some embodiments, the first polypeptide comprises the amino acid sequence of SEQ ID NO: 16, and the second polypeptide comprises the amino acid sequence of SEQ ID NO: 15.

In some embodiments, the SAP-Fc fusion proteins described herein bind to amyloid deposits or fibrils. In some embodiments, the SAP-Fc fusion protein binds to one or more amyloidogenic peptides in amyloids. In some embodiments, amyloids bound by the SAP-Fc fusion protein comprise an amyloidogenic λ6 variable domain protein (Vλ6Wil) or an amyloid genic immunoglobulin light chain (AL), Aβ(1-40) amyloid-like fibril or an amyloidogenic AP precursor protein, or serum amyloid protein A (AA). In other embodiments, the amyloids bound by the SAP-Fc fusion protein comprise amyloidogenic forms of immunoglobulin heavy chain (AH), β2-microglobulin (Aβ2M), transthyretin variants (ATTR), apolipoprotein AI (AApoAI), apolipoprotein AII (AApoAII), gelsolin (AGel), lysozyme (ALys), leukocyte chemotactic factor (ALect2), fibrinogen a variants (AFib), cystatin variants (ACys), calcitonin (ACal), lactadherin (AMed), islet amyloid polypeptide (AIAPP), prolactin (APro), insulin (AIns), prior protein (APrP), α-synuclein (AaSyn), tau (ATau), atrial natriuretic factor (AANF), IAAP, ALκ4, Alλ1, or other amyloidogenic peptides. The amyloidogenic peptides bound by the SAP-Fc fusion protein can be a protein, a protein fragment, or a protein domain. In some embodiments, the amyloid deposits or amyloid fibrils comprise recombinant amyloidogenic proteins. In some embodiments, the amyloids are part of the pathology of a disease.

In some embodiments, the SAP-Fc fusion protein promotes phagocytosis of amyloid deposits. In some embodiments, the SAP-Fc fusion protein promotes macrophage mediated phagocytosis.

In some embodiments, the SAP-Fc fusion proteins described herein are aglycosylated and bind to amyloid deposits or fibrils. In some embodiments, the aglycosylated SAP-Fc fusion protein binds to one or more amyloidogenic peptides in amyloids. In some embodiments, amyloids bound by the aglycosylated SAP-Fc fusion protein comprise an amyloidogenic λ6 variable domain protein (Vλ6Wil) or an amyloidogenic immunoglobulin light chain (AL), Aβ(1-40) amyloid-like fibril or an amyloidogenic AP precursor protein, or serum amyloid protein A (AA). In other embodiments, the amyloids bound by the aglycosylated SAP-Fc fusion protein comprise amyloidogenic forms of immunoglobulin heavy chain (AH), $β_2$-microglobulin (Aβ$_2$M), transthyretin variants (ATTR), apolipoprotein AI (AApoAI), apolipoprotein AII (AApoAII), gelsolin (AGel), lysozyme (ALys), leukocyte chemotactic factor (ALect2), fibrinogen a variants (AFib), cystatin variants (ACys), calcitonin (ACal), lactadherin (AMed), islet amyloid polypeptide (AIAPP), prolactin (APro), insulin (AIns), prior protein (APrP), α-synuclein (AaSyn), tau (ATau), atrial natriuretic factor (AANF), IAAP, ALκ4, Alλ1, or other amyloidogenic peptides. The amyloidogenic peptides bound by the aglycosylated SAP-Fc fusion protein can be a protein, a protein fragment, or a protein domain. In some embodiments, the amyloid deposits or amyloid fibrils comprise recombinant amyloidogenic proteins. In some embodiments, the amyloids are part of the pathology of a disease. In some embodiments, the aglycosylated SAP-Fc fusion protein promotes phagocytosis of amyloid deposits. In some embodiments, the aglycosylated SAP-Fc fusion protein promotes macrophage mediated phagocytosis.

In some embodiments, the SAP-Fc fusion proteins described herein are glycosylated and bind to amyloid deposits or fibrils. In some embodiments, the glycosylated SAP-Fc fusion protein binds to one or more amyloidogenic peptides in amyloids. In some embodiments, amyloids bound by the glycosylated SAP-Fc fusion protein comprise an amyloidogenic λ6 variable domain protein (Vλ6Wil) or an amyloidogenic immunoglobulin light chain (AL), Aβ(1-40) amyloid-like fibril or an amyloidogenic Aβ precursor protein, or serum amyloid protein A (AA). In other embodiments, the amyloids bound by the glycosylated SAP-Fc fusion protein comprise amyloidogenic forms of immunoglobulin heavy chain (AH), $β_2$-microglobulin (Aβ$_2$M), transthyretin variants (ATTR), apolipoprotein AI (AApoAI), apolipoprotein AII (AApoAII), gelsolin (AGel), lysozyme (ALys), leukocyte chemotactic factor (ALect2), fibrinogen a variants (AFib), cystatin variants (ACys), calcitonin (ACal), lactadherin (AMed), islet amyloid polypeptide (AIAPP), prolactin (APro), insulin (AIns), prior protein (APrP), α-synuclein (AaSyn), tau (ATau), atrial natriuretic factor (AANF), IAAP, ALκ4, Alλ1, or other amyloidogenic peptides. The amyloidogenic peptides bound by the glycosylated SAP-Fc fusion protein can be a protein, a protein fragment, or a protein domain. In some embodiments, the amyloid deposits or amyloid fibrils comprise recombinant amyloidogenic proteins. In some embodiments, the amyloids are part of the pathology of a disease. In some embodiments, the glycosylated SAP-Fc fusion protein promotes phagocytosis of amyloid deposits. In some embodiments, the glycosylated SAP-Fc fusion protein promotes macrophage mediated phagocytosis.

It is known that glycosylation patterns differ between proteins produced in nonhuman cells (such as CHO cells) and in human cells (such as HEK293 cells). In some embodiments, the SAP-Fc fusion proteins described herein are produced in human cells, such as HEK293 cells, and bind to amyloid deposits or fibrils. In some embodiments, the SAP-Fc fusion protein produced in human cells, such as HEK293 cells, binds to one or more amyloidogenic peptides in amyloids. In some embodiments, amyloids bound by the SAP-Fc fusion protein produced in human cells, such as HEK293 cells, comprise an amyloidogenic λ6 variable domain protein (Vλ6Wil) or an amyloidogenic immunoglobulin light chain (AL), Aβ(1-40) amyloid-like fibril or an amyloidogenic Aβ precursor protein, or serum amyloid protein A (AA). In other embodiments, the amyloids bound by the SAP-Fc fusion protein produced in human cells, such as HEK293 cells, comprise amyloidogenic forms of immunoglobulin heavy chain (AH), $β_2$-microglobulin (Aβ$_2$M), transthyretin variants (ATTR), apolipoprotein AI (AApoAI), apolipoprotein AII (AApoAII), gelsolin (AGel), lysozyme (ALys), leukocyte chemotactic factor (ALect2), fibrinogen a variants (AFib), cystatin variants (ACys), calcitonin (ACal), lactadherin (AMed), islet amyloid polypeptide (AIAPP), prolactin (APro), insulin (AIns), prior protein (APrP), α-synuclein (AaSyn), tau (ATau), atrial natriuretic factor (AANF), IAAP, ALκ4, Alλ1, or other amyloidogenic peptides. The amyloidogenic peptides bound by the SAP-Fc fusion protein produced in human cells, such as HEK293 cells, can be a protein, a protein fragment, or a protein domain. In some embodiments, the amyloid deposits or amyloid fibrils comprise recombinant amyloidogenic proteins. In some embodiments, the amyloids are part of the pathology of a disease. In some embodiments, the SAP-Fc fusion protein produced in human cells, such as HEK293 cells, promotes phagocytosis of amyloid deposits. In some embodiments, the SAP-Fc fusion protein produced in human cells, such as HEK293 cells, promotes macrophage mediated phagocytosis. In some embodiments, the SAP-Fc fusion proteins described herein are produced in non-human cells, such as CHO cells, and bind to amyloid deposits or fibrils. In some embodiments, the SAP-Fc fusion protein produced in non-human cells, such as CHO cells, binds to one or more amyloidogenic peptides in amyloids. In some embodiments, amyloids bound by the SAP-Fc fusion protein produced in non-human cells, such as CHO cells, comprise an amyloidogenic λ6 variable domain protein (Vλ6Wil) or an amyloidogenic immunoglobulin light chain (AL), Aβ(1-40) amyloid-like fibril or an amyloidogenic Aβ precursor protein, or serum amyloid protein A (AA). In other embodiments, the amyloids bound by the SAP-Fc fusion protein produced in non-human cells, such as CHO cells, comprise amyloidogenic forms of immunoglobulin heavy chain (AH), $β_2$-microglobulin (Aβ$_2$M), transthyretin variants (ATTR), apolipoprotein AI (AApoAI), apolipoprotein AII (AApoAII), gelsolin (AGel), lysozyme (ALys), leukocyte chemotactic factor (ALect2), fibrinogen a variants (AFib), cystatin variants (ACys), calcitonin (ACal), lactadherin (AMed), islet amyloid polypeptide (AIAPP), prolactin (APro), insulin (AIns), prior protein (APrP), α-synuclein (AaSyn), tau (ATau), atrial natriuretic factor (AANF), IAAP, ALκ4, Alλ1, or other amyloidogenic peptides. The amyloidogenic peptides bound by the SAP-Fc fusion protein produced in non-human cells, such as CHO cells, can be a protein, a protein fragment, or a protein domain. In some embodiments, the amyloid deposits or amyloid fibrils comprise recombinant amyloidogenic proteins. In some embodiments, the amyloids are part of the pathology of a disease.

In some embodiments, the SAP-Fc fusion protein produced in non-human cells, such as CHO cells, promotes phagocytosis of amyloid deposits. In some embodiments, the SAP-Fc fusion protein produced in non-human cells, such as CHO cells, promotes macrophage mediated phagocytosis.

In some embodiments, binding of the SAP-Fc fusion proteins described herein to amyloid deposits or fibrils is not affected by the glycosylation state of the SAP-Fc fusion proteins. In some embodiments, binding of an SAP-Fc fusion protein to one or more amyloidogenic peptides in amyloids is not affected by the glycosylation state of the SAP-Fc fusion protein. In some embodiments, amyloids bound by the SAP-Fc fusion protein comprise an amyloidogenic λ6 variable domain protein (Vλ6Wil) or an amyloidogenic immunoglobulin light chain (AL), Aβ(1-40) amyloid-like fibril or an amyloidogenic precursor protein, Of serum amyloid protein A (AA). In other embodiments, the amyloids bound by the SAP-Fc fusion protein comprise amyloidogenic forms of immunoglobulin heavy chain (AH), $\beta_2$-microglobulin (A$\beta_2$M), transthyretin variants (ATTR), apolipoprotein AI (AApoAI), apolipoprotein AII (AApoAII), gelsolin (AGel), lysozyme (ALys), leukocyte chemotactic factor (ALect2), fibrinogen a variants (AFib), cystatin variants (ACys), calcitonin (ACal), lactadherin (AMed), islet amyloid polypeptide (AIAPP), prolactin (APro), insulin (AIns), prior protein (APrP), α-synuclein (AaSyn), tau (ATau), atrial natriuretic factor (AANF), IAAP, ALκ4, Alλ1, or other amyloidogenic peptides. The amyloidogenic peptides bound by the SAP-Fc fusion protein can be a protein, a protein fragment, or a protein domain. In some embodiments, the amyloid deposits or amyloid fibrils comprise recombinant amyloidogenic proteins. In some embodiments, the amyloids are part of the pathology of a disease. In some embodiments, the activity of an SAP-Fc fusion protein described herein in promoting phagocytosis of amyloid deposits is not affected by the glycosylation state of the SAP-Fc fusion protein. In some embodiments, the activity of an SAP-Fc fusion protein described herein in promoting macrophage mediated phagocytosis is not affected by the glycosylation state of the SAP-Fc fusion protein.

In some embodiments, the SAP-Fc fusion proteins provided herein comprise two Fc polypeptides and one SAP polypeptide. In some embodiments, the SAP-Fc fusion proteins form stable non-covalent heterodimers. In some embodiments, the SAP-Fc fusion proteins do not comprise one more cysteine located at the Fc hinge region. In some embodiments, the SAP-Fc fusion proteins have reduced aggregation.

In some embodiments, the dimeric SAP-Fc fusion proteins provided herein form stable non-covalent pentamers. In some embodiments the pentamers are stable for 1, 2, 3, 4, 5, 24 hours or more. In some embodiments, the pentamers are stable on a size exclusion chromatography column. In some embodiments the pentamer has a molecular weight of about 375 kDa.

In some embodiments, the dimeric SAP-Fc fusion proteins provided herein form stable non-covalent decamers. In some embodiments the decamers are stable for 1, 2, 3, 4, 5, 24 hours or more. In some embodiments, the decamers are stable on a size exclusion chromatography column. In some embodiments, the decamer has a molecular weight of about for SAP-Fc decamer is about 750 kDa.

Also provided herein are pharmaceutical compositions comprising a SAP-Fc fusion protein and a pharmaceutically acceptable carrier. In some embodiments, pharmaceutical composition can be essentially free of any preservatives and other carriers, excipients, or stabilizers. Alternatively, the pharmaceutical composition can optionally include one or more preservatives, for example, antibacterial agents, pharmaceutically acceptable carriers, excipients, or stabilizers described elsewhere herein provided they do not adversely affect the physicochemical stability of the SAP-Fc fusion. Examples of acceptable carriers, excipients, and stabilizers include, but are not limited to, additional buffering agents, co-solvents, surfactants, antioxidants including ascorbic acid and methionine, chelating agents such as EDTA, metal complexes (for example, Zn-protein complexes), and biodegradable polymers such as polyesters. A thorough discussion of formulation and selection of pharmaceutically acceptable carriers, stabilizers, and isomolytes can be found in Remington's Pharmaceutical Sciences (18th ed.; Mack Publishing Company, Eaton, Pa., 1990), herein incorporated by reference.

The formulations to be used for in vivo administration must be sterile. This is readily accomplished by filtration through sterile filtration membranes.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Methods of Treatment

Also provided herein are methods of treating an amyloid related disorder comprising administering an SAP-Fc fusion protein disclosed herein to an individual.

In some embodiments, the SAP-Fc fusion protein binds to amyloid deposits. In some embodiments, the amyloid deposits may contribute to the pathology of a disease. In other embodiments, the amyloid deposits may be indicative of amyloidosis or an amyloid-related disease in an individual. In some embodiments, the SAP-Fc fusion protein binds to amyloids in an individual with an amyloidosis. In some embodiments, the amyloidosis is localized to a specific tissue or organ system, such as the liver, the heart, or the central nervous system.

In other embodiments, the amyloidosis is a systemic amyloidosis. In some embodiments, the amyloidosis is a familial amyloidosis. In other embodiments, the amyloidosis is a sporadic amyloidosis. In some embodiments, the amyloidosis or amyloid-related disease is AA amyloidosis, AL amyloidosis, AH amyloidosis, A$\beta$ amyloidosis, ATTR amyloidosis, ALect2 amyloidosis, and IAPP amyloidosis of type II diabetes, Alzheimer's disease, Down's syndrome, hereditary cerebral hemorrhage with amyloidosis of the Dutch type, cerebral beta-amyloid angiopathy, spongiform encelohalopathy, thyroid tumors, Parkinson's disease, dementia with Lewis bodies, a tauopathy, Huntington's disease, senile systemic amyloidosis, familial hemodialysis, senile systemic aging, aging pituitary disorder, iatrogenic syndrome, spongiform encephalopathies, reactive chronic inflammation, thyroid tumors, myeloma or other forms of cancer. In some embodiments, the SAP-Fc fusion protein binds to amyloids associated with normal aging. In other embodiments, the SAP-Fc fusion protein is used in the diagnosis, treatment, or prognosis of an amyloidosis or amyloid-related disease in an subject.

In some embodiments, the individual or subject to be treated is an animal, such as a mammal. In some embodiments, the mammal is dogs, cats, horses, cattle, dairy cows, swine, sheep, lamb, goats, primate, mouse, rat, or human. In some embodiments, the individual or subject is human.

Host Cells, Vectors, Methods of Production

In some embodiments, provided herein is nucleic acid encoding an SAP-Fc fusion protein. In some embodiments, the nucleic acid is in a vector. In some embodiments, the vector is an expression vector. In some embodiments, the vector is for prokaryotic expression. In some embodiments, the vector is for eukaryotic expression. In some embodiments, the vector is a mammalian expression vector. In some embodiments, the vector is a viral vector. In some embodiments, the vector comprises a promoter that drives transcription of the SAP-Fc fusion protein. In some embodiments, the promoter is a constitutive or inducible promoter.

In some embodiments, a SAP-Fc fusion protein is produced by culturing a host cell transformed with a nucleic acid, preferably an expression vector, containing a nucleic acid encoding the polypeptide construct (e.g., Fc variant, linker, and fusion partner) under the appropriate conditions to induce or cause expression of the polypeptide construct. In some embodiments, the conditions appropriate for expression varies with the expression vector and the host cell chosen. In some embodiments, a wide variety of appropriate host cells are used, including, but not limited to, mammalian cells, bacteria, insect cells, and yeast. For example, a variety of cell lines that find use in the present disclosure are described in the ATCC® cell line catalog, available from the American Type Culture Collection. In some embodiments, SAP-Fc fusion proteins of this disclosure are expressed in a cell that is optimized not to glycosylate proteins that are expressed by such cell, either by genetic engineering of the cell line or modifications of cell culture conditions such as addition of kifunensine or by using a naturally non-glycosylating host such as a prokaryote (E. coli, etc.), and in some cases, modification of the glycosylation sequence in the Fc is not be needed.

In some embodiments, mammalian cells are used as host cells to produce polypeptides of the disclosure. Examples of mammalian cell types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7O3O, and HsS78Bst cells. In some embodiments, E. coli cells are used as host cells to produce polypeptides of the disclosure. Examples of E. coli strains include, but are not limited to, E. coli 294 (ATCC® 31,446), E. coli λ 1776 (ATCC® 31,537, E. coli BL21 (DE3) (ATCC® BAA-1025), and E. coli RV308 (ATCC® 31,608).

Different host cells have characteristic and specific mechanisms for the posttranslational processing and modification of protein products (e.g., glycosylation). In some embodiments, appropriate cell lines or host systems are chosen to ensure the correct modification and processing of the polypeptide expressed. In some embodiments, a host cell is selected that does not produce $\alpha$2,3-linked sialic acid SAP moieties. In some embodiments, a host cell is selected that produces $\alpha$2,6-linked sialic acid SAP moieties at a similar level to wild-type human SAP.

Once the vectors are introduced into host cells for protein production, host cells are cultured in conventional nutrient media modified as appropriate for inducing promoters, selecting transformants, or amplifying the genes encoding the desired sequences.

In some embodiments, a polypeptide construct, for example a polypeptide construct comprising an SAP-Fc fusion protein, are expressed in mammalian expression systems, including systems in which the expression constructs are introduced into the mammalian cells using virus such as retrovirus or adenovirus. In some embodiments, human, mouse, rat, hamster, or primate cells are utilized. Suitable cells also include known research cells, including but not limited to Jurkat T cells, NIH3T3, CHO, COS, and 293 cells. Alternately, in some embodiments, proteins are expressed in bacterial cells. Bacterial expression systems are well known in the art, and include *Escherichia coli* (*E. coli*), *Bacillus subtilis, Streptococcus cremoris*, and *Streptococcus lividans*. In some cases, polypeptide constructs comprising Fc variants are produced in insect cells such as but not limited to Sf9 and Sf21 cells or yeast cells such as but not limited to organisms from the genera *Saccharomyces, Pichia, Kluyveromyces, Hansenula* and *Yarrowia*. In some cases, polypeptide constructs comprising Fc variants are expressed in vitro using cell free translation systems. In vitro translation systems derived from both prokaryotic (e.g., *E. coli*) and eukaryotic (e.g., wheat germ, rabbit reticulocytes) cells are available and, in some embodiments, chosen based on the expression levels and functional properties of the protein of interest. For example, as appreciated by those skilled in the art, in vitro translation is required for some display technologies, for example ribosome display. In addition, in some embodiments, the SAP-Fc fusion proteins variants are produced by chemical synthesis methods such as, but not limited to, liquid-phase peptide synthesis and solid-phase peptide synthesis. In the case of in vitro transcription using a non-glycosylating system such as bacterial extracts, the Fc will not be glycosylated even in presence of the natural glycosylation site and therefore inactivation of the Fc will be equivalently obtained.

In some embodiments, a polypeptide construct includes non-natural amino acids, amino acid analogues, amino acid mimetics, or any combinations thereof that function in a manner similar to the naturally occurring amino acids. Naturally encoded amino acids generally refer to the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, e.g., an a carbon that is bound to a hydrogen, a carboxyl group, an amino group, and an R group, such as, homoserine, norleucine, methionine sulfoxide, methionine methyl sulfonium. In some embodiments, such analogs have modified R groups (such as, norleucine) or modified peptide backbones, but generally retain the same basic chemical structure as a naturally occurring amino acid.

Protein Production, Recovery, and Purification

In some embodiments, host cells used to produce polypeptides of the disclosure are grown in media suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. In some embodiments, host cells are cultured at suitable temperatures, such as from about 20° C. to about 39° C., e.g., from about 25° C. to about 37° C., preferably 37° C., and CO2 levels, such as about 5% to 10%. In some embodiments, the pH of the medium is from about pH 6.8 to pH 7.4, e.g., pH 7.0, depending mainly on the host organism. If an inducible promoter is used in the expression vector, protein expression can be induced under conditions suitable for the activation of the promoter.

In some embodiments, protein recovery involves disrupting the host cell, for example by osmotic shock, sonication, or lysis. Once the cells are disrupted, cell debris is removed by centrifugation or filtration. The proteins can then be further purified. In some embodiments, a polypeptide of the disclosure is purified by various methods of protein purification, for example, by chromatography (e.g., ion exchange chromatography, affinity chromatography, and size-exclusion column chromatography), centrifugation, differential solubility, or by any other standard technique for the purification of proteins. For example, in some embodiments, the protein is isolated and purified by appropriately selecting and combining affinity columns such as Protein A column (e.g., POROS Protein A chromatography) with chromatography columns (e.g., POROS HS-50 cation exchange chromatography), filtration, ultra-filtration, de-salting and dialysis procedures. In some embodiments, a polypeptide is conjugated to marker sequences, such as a peptide to facilitate purification. An example of a marker amino acid sequence is a hexa-histidine peptide (His6-tag), which can bind to a nickel-functionalized agarose affinity column with micromolar affinity. As an alternative, a hemagglutinin "HA" tag, which corresponds to an epitope derived from the influenza hemagglutinin protein can be used.

In some embodiments, polypeptides of the disclosure, for example a polypeptide construct comprising an SAP-Fc fusion protein, are produced by the cells of a subject (e.g., a human), e.g., in the context of gene therapy, by administrating a vector such as a viral vector (e.g., a retroviral vector, adenoviral vector, poxviral vector (e.g., vaccinia viral vector, such as Modified Vaccinia Ankara (MVA)), adeno-associated viral vector, and alphaviral vector) containing a nucleic acid molecule encoding a polypeptide of the disclosure. The vector, once inside a cell of the subject (e.g., by transformation, transfection, electroporation, calcium phosphate precipitation, direct microinjection, infection, etc) can be used for the expression of a polypeptide disclosed herein. In some cases, the polypeptide is secreted from the cell. In some embodiments, if treatment of a disease or disorder is the desired outcome, no further action is required. In some embodiments, if collection of the protein is desired, blood is collected from the subject and the protein purified from the blood by various methods.

Kits

Also provided herein are kits comprising an SAP-Fc fusion protein and instructions for use. In some embodiments, the kit comprises instructions according to any of the methods described herein. In some embodiments, the kit comprises instructions for treating an amyloid disorder. In some embodiments, the kit comprises instructions for treating a systemic amyloid disorder. In some embodiments, the kit comprises instructions for treating AA amyloidosis, AL amyloidosis, AH amyloidosis, amyloidosis, ATTR amyloidosis, ALect2 amyloidosis, and IAPP amyloidosis of type II diabetes, Alzheimer's disease, Down's syndrome, hereditary cerebral hemorrhage with amyloidosis of the Dutch type, cerebral beta-amyloid angiopathy, spongiform encelohalopathy, thyroid tumors, Parkinson's disease, dementia with Lewis bodies, a tauopathy, Huntington's disease, senile systemic amyloidosis, familial hemodialysis, senile systemic aging, aging pituitary disorder, iatrogenic syndrome, spongiform encephalopathies, reactive chronic inflammation, thyroid tumors, myeloma or other forms of cancer.

The kit may also comprise the SAP-Fc fusion protein in a container such as a vial, bag, pump, or a syringe. In some embodiments, the SAP-Fc fusion protein is in a pharmaceutical composition.

EMBODIMENTS

1. A fusion protein comprising a first polypeptide and a second polypeptide, wherein the first polypeptide comprises a human serum amyloid P (SAP) component protein linked to the N-terminus of a first human Fc domain, wherein the second polypeptide comprises a second human Fc domain but does not comprise a human SAP component protein, wherein the first and the second Fc domains form a dimer, and wherein the one of the two Fc domains comprises a knob mutation and the other Fc domain comprises a hole mutation.

2. The fusion protein of embodiment 1, wherein the first polypeptide comprises a knob mutation and the second polypeptide comprises a hole mutation.

3. The fusion protein of embodiment 2, wherein the first polypeptide comprises the amino acid sequence set forth in SEQ ID NO:5, SEQ ID NO:7, SEQ ID NO: 8, or SEQ ID NO: 10 and the second polypeptide comprises the amino acid sequence set forth in SEQ ID NO:6 or SEQ ID NO:9.

4. The fusion protein of embodiment 1, wherein the fusion protein comprises the first polypeptide and the second polypeptide sequences of TNT 148, TNT 152, TNT 157, TNT 158, TNT 147, TNT 159, TNT 160, or TNT 161 according to Table 2.

5. The fusion protein of embodiment 1, wherein the Fc domain of the first polypeptide comprises a hole mutation and the Fc domain of the second polypeptide comprises a knob mutation.

6. The fusion protein of embodiment 5, wherein the first polypeptide comprises the amino acid sequence set forth in SEQ ID NO: 11, SEQ ID NO: 13, SEQ ID NO: 14, or SEQ ID NO: 16 and the second polypeptide comprises the amino acid sequence set forth in SEQ ID NO: 12 or SEQ ID NO: 15.

7. A fusion protein comprising a structure represented by the following formula, from N-terminus to C-terminus, SAP-hinge1-Fc1-L1-hinge2-Fc2, wherein SAP is a human serum amyloid P (SAP) component protein, hinge1 is a first hinge sequence, Fc1 is a first Fc domain sequence, L1 is a linker, hinge 2 is a second hinge sequence, and Fc2 is a second Fc domain sequence.

8. The fusion protein of embodiment 7, wherein the fusion protein comprises the amino acid sequence set forth in SEQ ID NO: 1, SEQ ID NO: 2, SEQ ID NO: 3, SEQ ID NO: 4, SEQ ID NO: 23, or SEQ ID NO: 24.

9. The fusion protein of embodiment 7, wherein the fusion protein comprises the polypeptide sequence of TNT 146, TNT 151, TNT 155, TNT 156, TNT 170, or TNT 171.

10. The fusion protein of embodiment 1 or embodiment 7, wherein the human serum amyloid P component protein comprises an amino acid substitution at position N32 or N110 according to SEQ ID NO:17.

11. The fusion protein of embodiment 10, wherein the human serum amyloid P component protein comprises the amino acid sequence set forth in SEQ ID NO. 20.

12. The fusion protein of embodiment 1 or embodiment 7, wherein the first and second Fc domain comprises an amino acid substitution at position C226 or C229 according to EU numbering.

13. The fusion protein of embodiment 12, wherein the first and second Fc domain comprises amino acid substitutions C226S or C229S, according to EU numbering.

14. The fusion protein of embodiment 1 or embodiment 7, wherein the first and second Fc domain comprises an amino acid substitution at amino acid position 11 or 14, numbering according to the amino acid sequence of SEQ ID NO: 18.

15. The fusion protein of embodiment 14, wherein the first and second Fc domain comprises a serine residue at amino acid position 11 or 14, numbering according to the amino acid sequence of SEQ ID NO: 18.

16. The fusion protein of any one of embodiments 12-15, wherein the first or second Fc domain comprises the amino acid sequence set forth in SEQ ID NO: 18.

17. The fusion protein of embodiment 1 or embodiment 7, wherein the first and/or second Fc domain comprises a mutation that reduces FcRn binding.

18. The fusion protein of any one of embodiments 1-17, wherein the fusion protein forms a pentamer.

19. A pharmaceutical composition comprising the fusion protein of any one of embodiment 1-18.

20. Nucleic acid encoding the fusion protein of any one of embodiments 1-18.

21. A host cell comprising the nucleic acid of embodiment 20.

22. A method of producing the fusion protein of any one of embodiments 1-18, comprising culturing a host cell comprising nucleic acid encoding the fusion protein under conditions to express the fusion protein.

23. The method of embodiment 22, wherein the host cell is a CHO cell or a 293 cell.

24. The method of embodiment 22 or embodiment 23, wherein the host cell does not glycosylate the SAP component protein.

25. A method of treating an amyloid disease comprising administering the fusion protein of any one of embodiment 1-18 to an individual in need thereof.

26. The method of embodiment 25, wherein the amyloid disease comprises systemic amyloidosis.

27. A fusion protein comprising a structure represented by the following formula, from N-terminus to C-terminus, hinge1-Fc1-L1-hinge2-Fc2, wherein hinge1 is a first hinge sequence, Fc1 is a first Fc domain sequence, L1 is a linker, hinge 2 is a second hinge sequence, and Fc2 is a second Fc domain sequence, wherein the first and second Fc domain comprises amino acid substitutions C226S or C229S according to EU numbering, and/or wherein the first and second Fc domain comprises a serine residue at amino acid position 11 or 14, numbering according to the amino acid sequence of SEQ ID NO: 18.

28. The fusion protein of embodiment 27, wherein the fusion protein further comprise a human serum amyloid P (SAP) component protein at the N-terminus of the fusion protein.

1A. A fusion protein comprising a structure represented by the following formula, from N-terminus to C-terminus, SAP-Fc1-L1-Fc2, wherein Fc1 is a first Fc domain sequence comprising hinge-CH2-CH3, L1 is a linker, and Fc2 is a second Fc domain sequence comprising hinge-CH2-CH3, wherein SAP is a human serum amyloid P (SAP) component protein, wherein Fc1 and Fc2 comprise an amino acid substitution at position C226 and/or C229 according to EU numbering.

2A. The fusion protein of embodiment 1A, wherein Fc1 and Fc2 comprise an amino acid substitution at position C226 and C229 according to EU numbering.

3A. The fusion protein of embodiment 1A or 2A, wherein the fusion protein comprises the amino acid sequence set forth in SEQ ID NO: 1, SEQ ID NO: 2, SEQ ID NO: 3, SEQ ID NO: 4, SEQ ID NO: 23, or SEQ ID NO: 24.

4A. The fusion protein of embodiment 3A, wherein the fusion protein comprises the amino acid sequence set forth in SEQ ID NO: 1 without the C-terminal lysine, SEQ ID NO: 2 without the C-terminal lysine, SEQ ID NO: 3 without the C-terminal lysine, SEQ ID NO: 4 without the C-terminal lysine, SEQ ID NO: 23 without the C-terminal lysine, or SEQ ID NO: 24 without the C-terminal lysine.

5A. The fusion protein of embodiment 1A or 2A, wherein the fusion protein comprises the polypeptide sequence of TNT 146, TNT 151, TNT 155, TNT 156, TNT 170, or TNT 171.

6A. A fusion protein comprising a first polypeptide and a second polypeptide, wherein the first polypeptide comprises a human serum amyloid P (SAP) component protein linked to the N-terminus of a first human Fc domain (Fc1), wherein the second polypeptide comprises a second human Fc domain (Fc2) but does not comprise a human SAP component protein, wherein the first and the second Fc domains form a dimer, and wherein the one of the two Fc domains comprises a knob mutation and the other Fc domain comprises a hole mutation.

7A. The fusion protein of embodiment 6A, wherein the first polypeptide comprises a knob mutation and the second polypeptide comprises a hole mutation.

8A. The fusion protein of embodiment 7A, wherein the first polypeptide comprises the amino acid sequence set forth in SEQ ID NO:5, SEQ ID NO:7, SEQ ID NO: 8, or SEQ ID NO: 10 and the second polypeptide comprises the amino acid sequence set forth in SEQ ID NO:6 or SEQ ID NO:9.

9A. The fusion protein of embodiment 8A, wherein
the first polypeptide comprises the amino acid sequence set forth in SEQ ID NO:5 and the second polypeptide comprises the amino acid sequence set forth in SEQ ID NO:6;
the first polypeptide comprises the amino acid sequence set forth in SEQ ID NO:7 and the second polypeptide comprises the amino acid sequence set forth in SEQ ID NO:6;
the first polypeptide comprises the amino acid sequence set forth in SEQ ID NO:8 and the second polypeptide comprises the amino acid sequence set forth in SEQ ID NO:9; or
the first polypeptide comprises the amino acid sequence set forth in SEQ ID NO:10 and the second polypeptide comprises the amino acid sequence set forth in SEQ ID NO:6.

10A. The fusion protein of embodiment 8A, wherein
the first polypeptide comprises the amino acid sequence set forth in SEQ ID NO:5 with or without the C-terminal lysine, and the second polypeptide comprises the amino acid sequence set forth in SEQ ID NO:6 with or without the C-terminal lysine;
the first polypeptide comprises the amino acid sequence set forth in SEQ ID NO:7 with or without the C-terminal lysine and the second polypeptide comprises the amino acid sequence set forth in SEQ ID NO:6 with or without the C-terminal lysine;
the first polypeptide comprises the amino acid sequence set forth in SEQ ID NO:8 with or without the C-terminal lysine and the second polypeptide comprises the amino acid sequence set forth in SEQ ID NO:9 with or without the C-terminal lysine; or the first polypeptide comprises the amino acid sequence set forth in SEQ ID NO:10 with or without the C-terminal lysine and the second polypeptide comprises the amino acid sequence set forth in SEQ ID NO:6, with or without the C-terminal lysine.

11A. The fusion protein of embodiment 6A, wherein the fusion protein comprises the first polypeptide and the second polypeptide sequences of TNT 148, TNT 152, TNT 157, TNT 158, TNT 147, TNT 159, TNT 160, or TNT 161 according to Table 2.

12A. The fusion protein of embodiment 6A, wherein the Fc domain of the first polypeptide comprises a hole mutation and the Fc domain of the second polypeptide comprises a knob mutation.

13A. The fusion protein of embodiment 6A, wherein the first polypeptide comprises the amino acid sequence set forth in SEQ ID NO: 11, SEQ ID NO: 13, SEQ ID NO: 14, or SEQ ID NO: 16 and the second polypeptide comprises the amino acid sequence set forth in SEQ ID NO: 12 or SEQ ID NO: 15.

14A. The fusion protein of embodiment 13A, wherein
the first polypeptide comprises the amino acid sequence set forth in SEQ ID NO:11 and the second polypeptide comprises the amino acid sequence set forth in SEQ ID NO:12;
the first polypeptide comprises the amino acid sequence set forth in SEQ ID NO:13 and the second polypeptide comprises the amino acid sequence set forth in SEQ ID NO:12;
the first polypeptide comprises the amino acid sequence set forth in SEQ ID NO:14 and the second polypeptide comprises the amino acid sequence set forth in SEQ ID NO:15; or
the first polypeptide comprises the amino acid sequence set forth in SEQ ID NO:16 and the second polypeptide comprises the amino acid sequence set forth in SEQ ID NO:15.

15A. The fusion protein of embodiment 13A, wherein
the first polypeptide comprises the amino acid sequence set forth in SEQ ID NO:11 with or without the C-terminal lysine and the second polypeptide comprises the amino acid sequence set forth in SEQ ID NO:12 with or without the C-terminal lysine;
the first polypeptide comprises the amino acid sequence set forth in SEQ ID NO:13 with or without the C-terminal lysine and the second polypeptide comprises the amino acid sequence set forth in SEQ ID NO:12 with or without the C-terminal lysine;
the first polypeptide comprises the amino acid sequence set forth in SEQ ID NO:14 with or without the C-terminal lysine and the second polypeptide comprises the amino acid sequence set forth in SEQ ID NO:15 with or without the C-terminal lysine; or the first polypeptide comprises the amino acid sequence set forth in SEQ ID NO:16 with or without the C-terminal lysine and the second polypeptide comprises the amino acid sequence set forth in SEQ ID NO:15 with or without the C-terminal lysine.

16A. The fusion protein of embodiment 1A or embodiment 6A, wherein the human SAP is a wild-type SAP, optionally comprising the amino acid sequence set forth in SEQ ID NO:17.

17A. The fusion protein of embodiment 1A or embodiment 6A, wherein the human SAP comprises an amino acid substitution at position N32 or N110 according to SEQ ID NO:17.

18A. The fusion protein of embodiment 17A, wherein the human SAP comprises the amino acid sequence set forth in SEQ ID NO. 20.

19A. The fusion protein of any one of embodiments 6A or 16A-18A wherein Fc1 and Fc2 comprise an amino acid substitution at position C226 and/or C229 according to EU numbering.

20A. The fusion protein of embodiment 19A, wherein Fc1 and Fc2 comprise an amino acid substitution at position C226 and C229 according to EU numbering.

21A. The fusion protein of any one of embodiments 1A, 2A, 6A, or 16A-20A, wherein Fc1 and Fc2 comprise amino acid substitutions C226S and/or C229S, according to EU numbering.

22A. The fusion protein of embodiment 21A, wherein Fc1 and Fc2 comprise amino acid substitutions C226S and C229S, according to EU numbering.

23A. The fusion protein of any one of embodiments 1A, 2A, 6A, or 15A-17A, wherein Fc1 and/or Fc2 comprises an amino acid substitution at amino acid position 11 and/or 14, numbering according to the amino acid sequence of SEQ ID NO: 18.

24A. The fusion protein of embodiment 23A, wherein Fc1 and/or Fc2 comprises a serine residue at amino acid position 11 and/or 14, numbering according to the amino acid sequence of SEQ ID NO: 18.

25A. The fusion protein of embodiment 23A or 24A, wherein Fc1 and/or Fc2 comprises the amino acid sequence set forth in SEQ ID NO: 18.

26A. The fusion protein of embodiments 1A, 2A, 6A, or 16A-18A, wherein the first and/or second Fc domain comprises a mutation that reduces FcRn binding.

27A. A fusion protein comprising a structure represented by the following formula, from N-terminus to C-terminus, Fc1-L1-Fc2, wherein Fc1 is a first Fc domain sequence comprising hinge-CH2-CH3, L1 is a linker, and Fc2 is a second Fc domain sequence comprising hinge-CH2-CH3, wherein Fc1 and Fc2 comprise amino acid substitutions C226S and/or C229S according to EU numbering, and/or wherein Fc1 and Fc2 comprise a serine residue at amino acid position 11 and/or 14, numbering according to the amino acid sequence of SEQ ID NO: 18.

28A. The fusion protein of embodiment 27A, wherein the fusion protein further comprise a human serum amyloid P (SAP) component protein at the N-terminus of the fusion protein.

29A. The fusion protein of embodiment 28A, wherein the human SAP is a wild-type SAP, optionally comprising the amino acid sequence set forth in SEQ ID NO:17.

30A. The fusion protein of embodiment 28A, wherein the wherein the human SAP comprises an amino acid substitution at position N32 or N110 according to SEQ ID NO:17.

31A. The fusion protein of embodiment 30A, wherein the human SAP comprises the amino acid sequence set forth in SEQ ID NO. 20.

32A. The fusion protein of any one of embodiments 1A-31A, wherein the fusion protein forms a pentamer or a deccamer.

33A. The fusion protein of any one of embodiments 1A-32A, wherein the fusion protein comprises a human Fc region.

34A. The fusion protein of any one of embodiments 1A-33A, wherein the fusion protein comprises a human IgG1 Fc region.

35A. The fusion protein of any one of embodiments 1A-34A, wherein the fusion protein has reduced aggregation compared to a fusion protein lacking the one or more amino acid substitutions.

36A. A pharmaceutical composition comprising the fusion protein of any one of embodiments 1A-35A, and a pharmaceutically acceptable carrier.

37A. The pharmaceutical composition of embodiment 36A, wherein at least 50% of the fusion protein is in a pentamer and/or a decamer.

38A. Nucleic acid encoding the fusion protein of any one of embodiments 1A-35A.

39A. A vector comprising the nucleic acid of embodiment 38A.

40A. A host cell comprising the nucleic acid of claim 38 or the vector of embodiment 39A.

41A. The host cell of embodiment 40A, wherein the host cell is a CHO cell or a 293 cell.

42A. A method of producing the fusion protein of any one of embodiments 1A-35A, comprising culturing a host cell comprising nucleic acid encoding the fusion protein under conditions to express the fusion protein.

43A. The method of embodiment 42A, wherein the host cell is a CHO cell or a 293 cell.

44A. The method of embodiment 42 or embodiment 43, wherein the host cell does not glycosylate the SAP component protein.

45A. A method of treating an amyloid disease in an individual, comprising administering the fusion protein of any one of embodiments 1A-35A to the individual.

46A. A method of treating an amyloid disease in an individual, comprising administering a fusion protein produced by the method of any one of embodiments 42A-44A to the individual.

47A. The method of embodiment 45A or claim 46A, wherein the amyloid disease is selected form the group consisting of AA amyloidosis, AL amyloidosis, AH amyloidosis, amyloidosis, ATTR amyloidosis, ALect2 amyloidosis, IAPP amyloidosis of type II diabetes, and Alzheimer's disease.

48A. An SAP-Fc fusion protein produced by the method of any one of embodiments 42A-45A.

49A. The method of any one of embodiments 45A-47A, wherein the individual is a human.

EXAMPLES

Example 1. Production of the SAP-scFc Construct

Figures 6A, 6B:
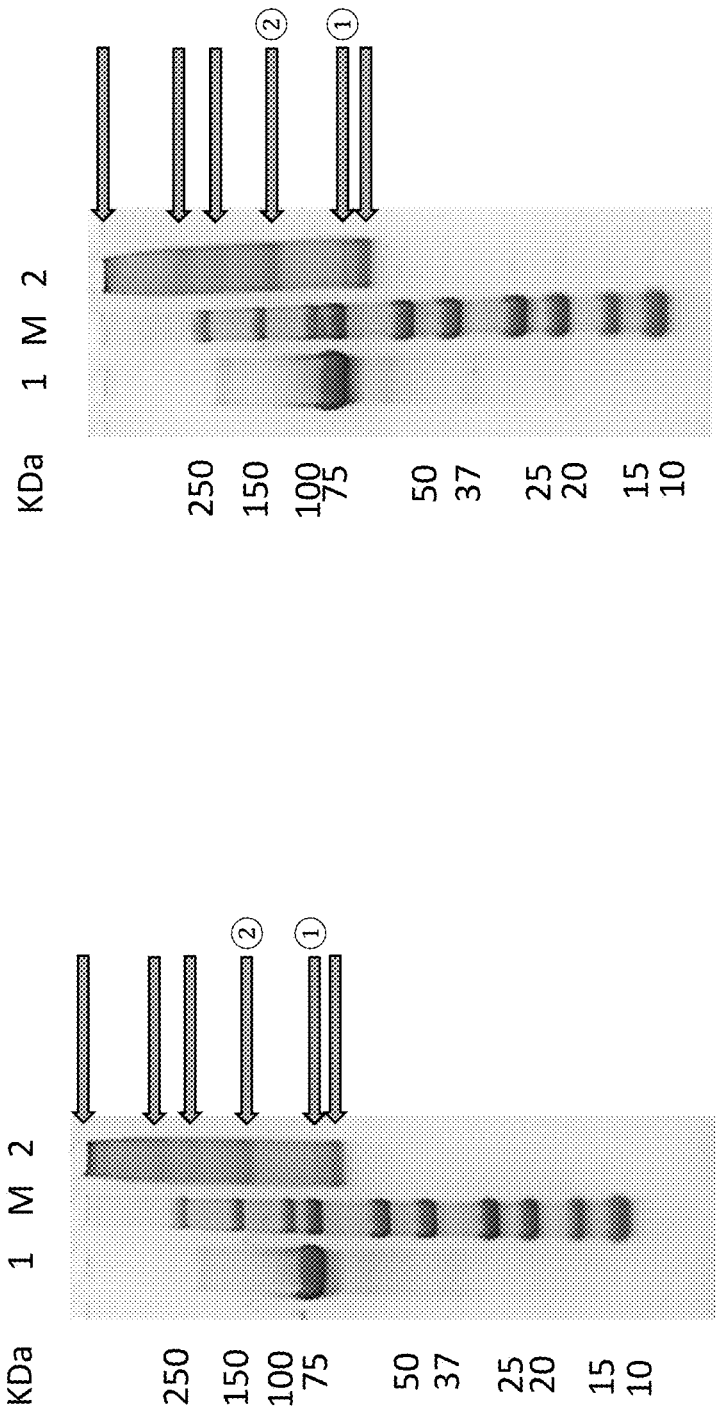
FIG. 6A and FIG. 6B show SDS-PAGE analysis of reduced and non-reduced SAP-Fc after purification steps. The lane labeled as "1" shows reduced sample of the purification product, the lane labeled as "2" shows non-reduced sample of the purification product, the lane labeled as "M" shows protein marker (ALL BLUE PRECISION PLUS, BIO-RAD®, Cat #161-0373). The arrows indicate monomer (labeled as "①"), dimer (labeled as "②"), and other oligomers.
Figure 7A:
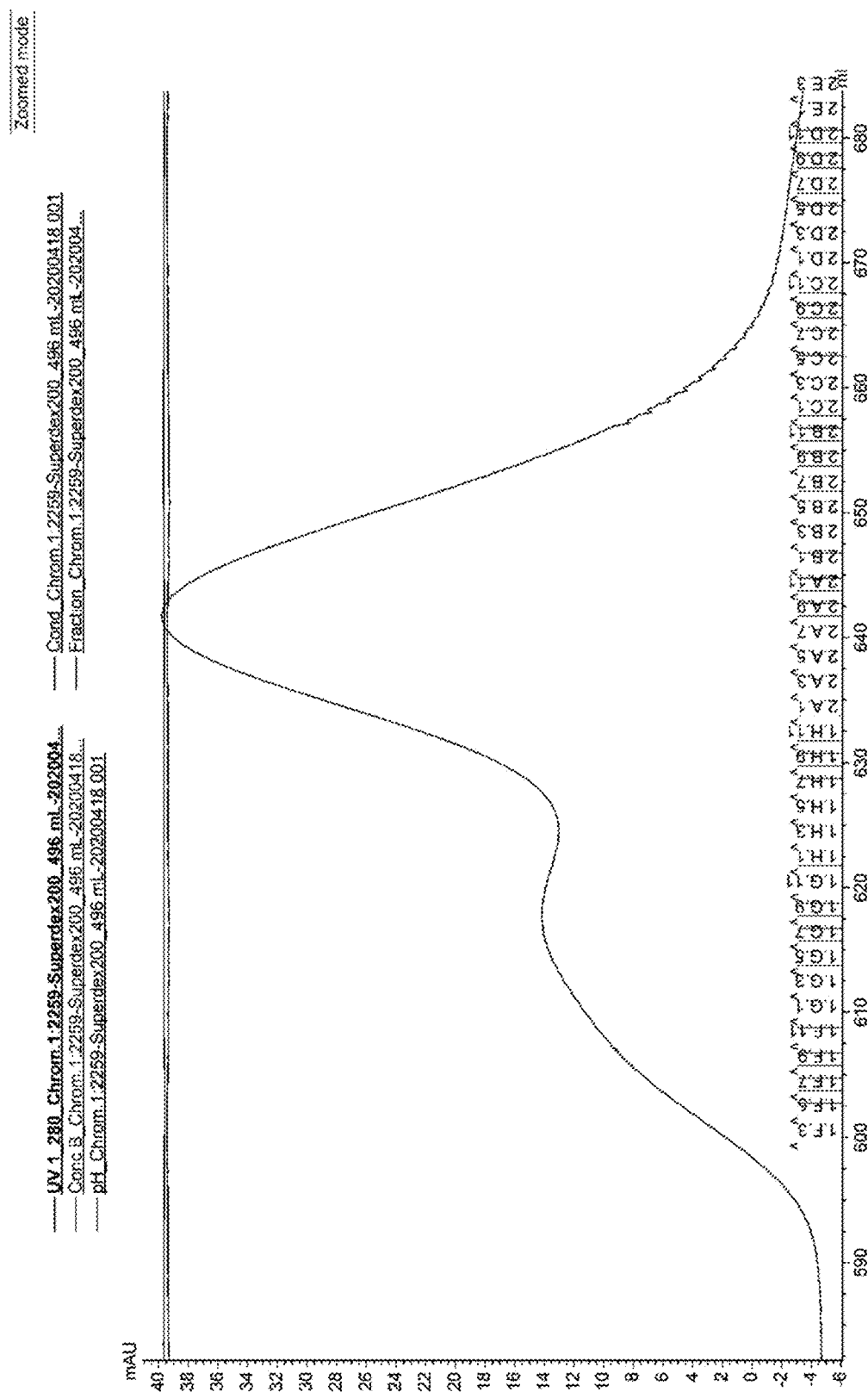
FIG. 7A shows the major elution peak of the SEC chromatogram. Sample fractions are labeled on the x-axis.
Figure 7B:
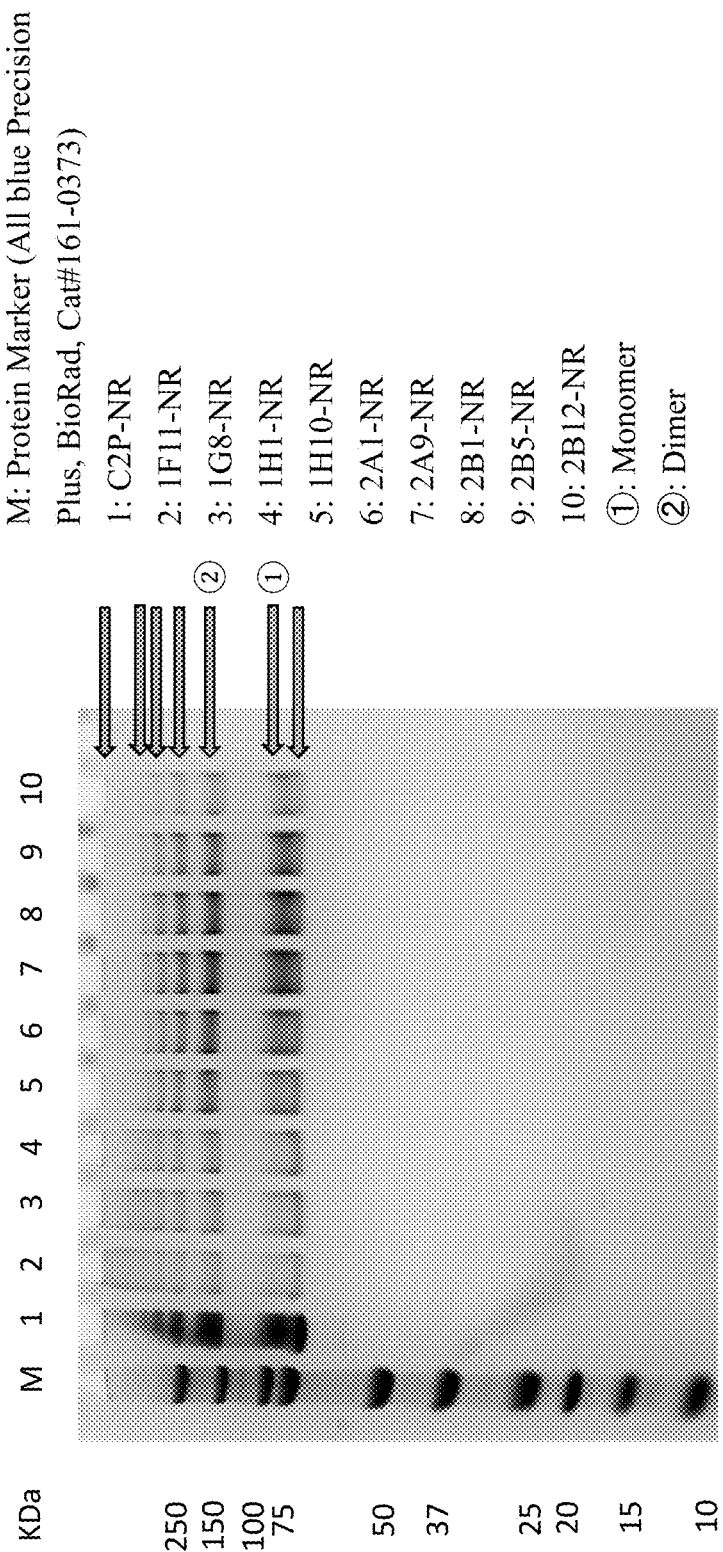
FIG. 7B shows non-reduced SDS-PAGE analysis of sample fractions from this SEC purification step.
Figure 7C:
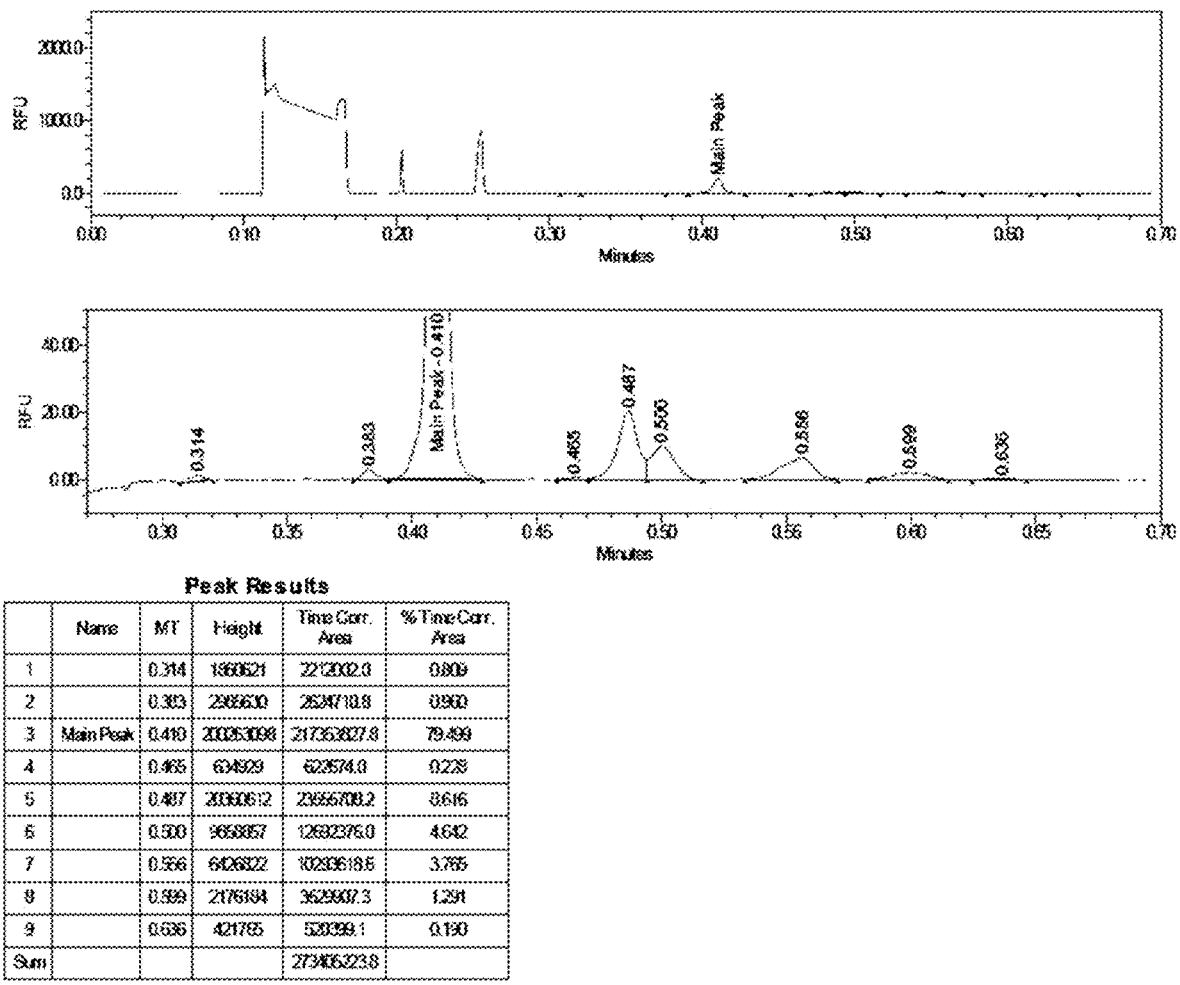
FIG. 7C shows non-reduced microfluidic electrophoresis analysis of fraction "2B1".
Figure 7D:
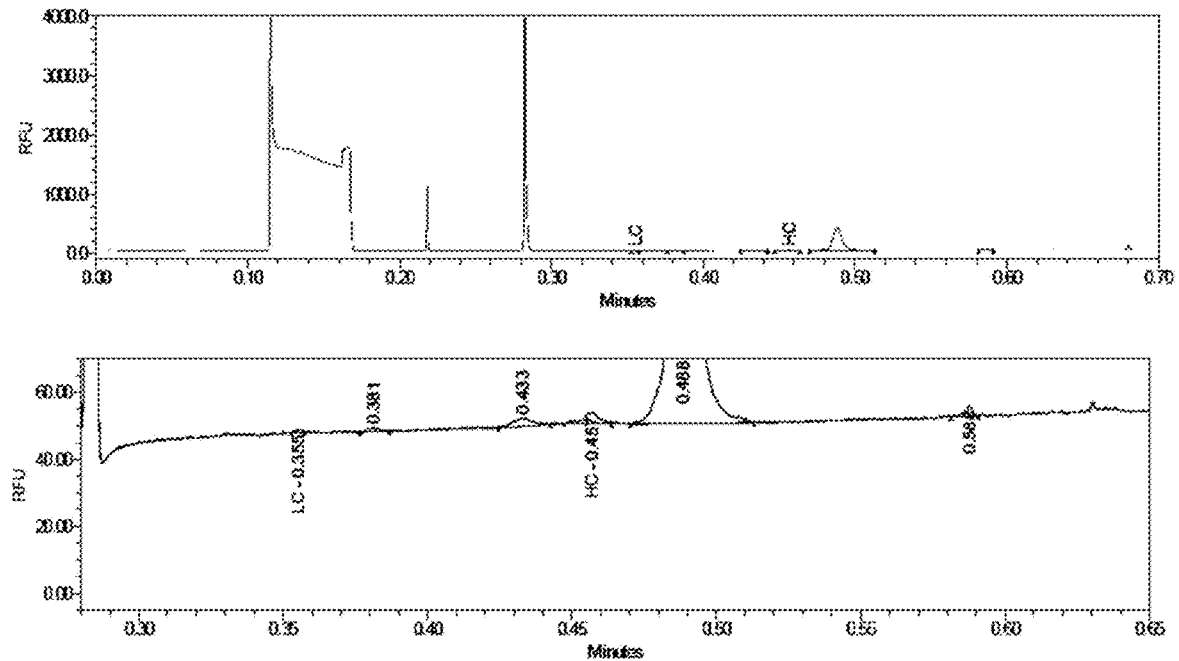
FIG. 7D shows reduced microfluidic electrophoresis analysis of fraction "2B1".
Figure 7E:
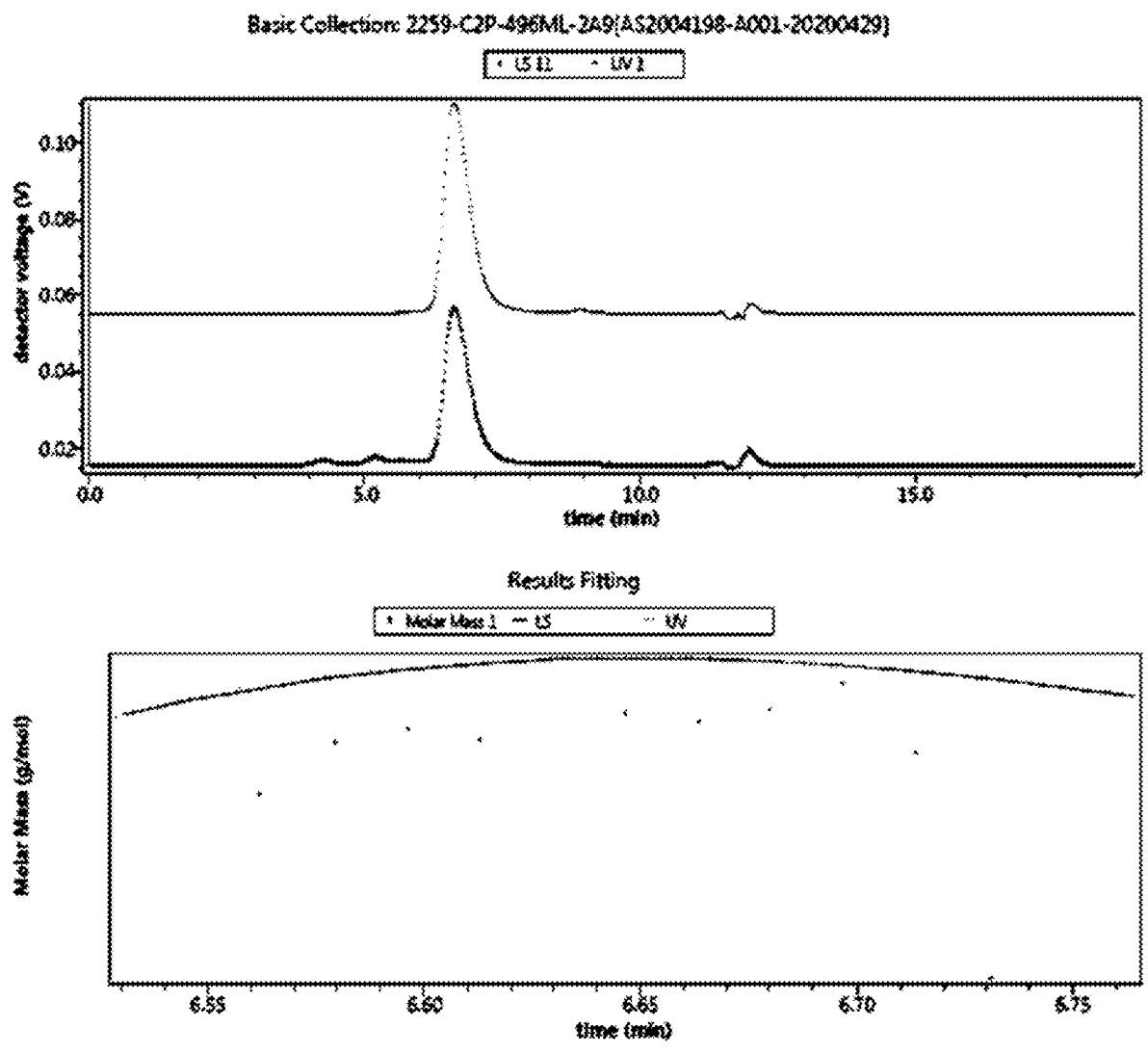
FIG. 7E shows size exclusion chromatography multi-angle light scattering (SEC-MALS) analysis of fraction "2A9".
Figure 7F:
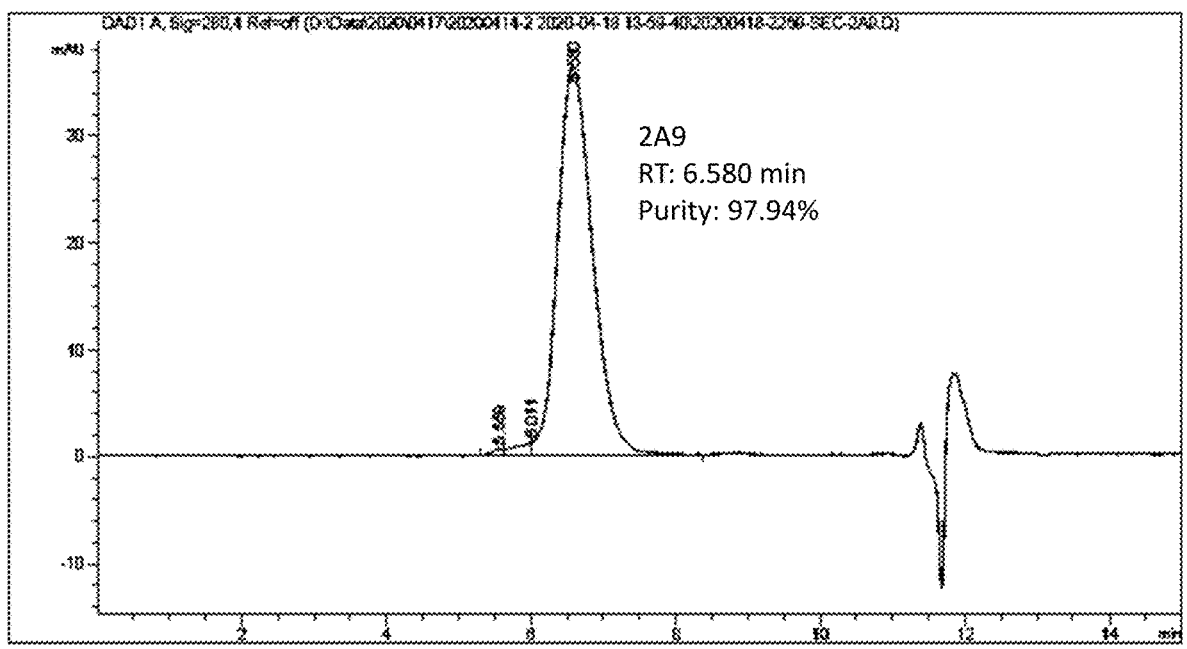
FIG. 7F shows SEC-HPLC analysis of fraction "2A9".
Figure 7G:
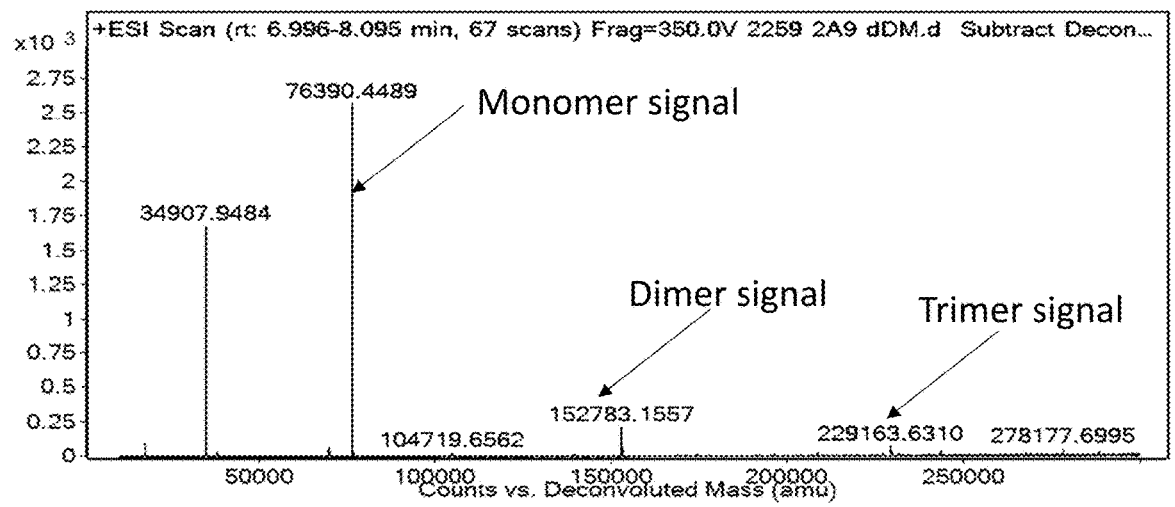
FIG. 7G shows deglycosylated mass analysis of fraction "2A9".

SAP-scFc was purified by a Protein A affinity (MABSELECT SURE™ LX, CYTIVA®) purification step and a 1700 ml size-exclusion chromatography (SEC) purification step. However, these purification steps were not able to separate monomer and dimer from other oligomers (FIG. 6A and FIG. 6B). To better separate monomer and dimer from other oligomers, the purification products of 1700 mL SEC were further polished by a 496 mL SEC purification step (FIG. 7A). SDS-PAGE analysis shows that fractions obtained in this step still contained a mixture of monomer, dimer, and other oligomers (FIG. 7B). The fraction "2B1" from the 496 mL SEC was selected for analysis by reduced and non-reduced microfluidic electrophoresis (LABCHIP® GXII, PERKINELMER®). Non-reduced microfluidic electrophoresis of fraction "2B1" showed as multiple oligomer peaks, while the reduced microfluidic electrophoresis showed a major monomer peak (FIGS. 7C-7D). The fraction "2A9" from the 496 mL SEC was selected for analysis by size exclusion chromatography multi-angle light scattering (SEC-MALS). The SEC-MALS result shows the SAP-scFc protein exists as a large molecular weight complex (FIG. 7E). These analyses indicate the 496 mL SEC purification step did not improve the separation of the monomer and dimer from other oligomers. SEC-HPLC analysis of the "2A9" fraction after the 496 mL SEC purification step showed a single peak (FIG. 7F), while denatured deglycosylated mass analysis showed monomer, dimer, and trimer signals (FIG. 7G). Thus, it is hypothesized that SAP-scFc could exist as a complex of monomer, dimer, and trimer combined through noncovalent interactions.

The purification product of 1700 mL SEC was also subjected to further small scale polishing step using SP SEPHAROSE high performance strong cation exchange chromatography (HITRAP™ SP HP, CYTIVA®), POROS™ XS strong cation exchange chromatography (THERMO FISHER SCIENTIFIC®), PHENYL SEPHAROSE 6 fast flow hydrophobic interaction chromatography (HITRAP™ PHENYL FF, CYTIVA®), BUTYL-S SEP- HAROSE 6 fast flow hydrophobic interaction chromatography (HITRAP™ BUTYL-S FF, CYTIVA®), BIOPROCESS CAPTO PHENYL IMPRES hydrophobic interaction chromatography (HITRAP™ CAPTO PHENYL IMPRES, CYTIVA®), and CHT™ ceramic hydroxyapatite calcium-affinity cation-exchange chromatography (BIO-RAD®). However, none of the small scale polishing methods improved the separation of the monomer and dimer from other oligomers.

Example 2. Modified SAP-Fc Fusion Proteins

As described in Example 1, the structure of the SAP-Fc caused difficulties in the purification process. To improve the expression and purification profile, modifications of the SAP-Fc structure were explored.

Modification of the SAP-Fc to Remove Cysteine Residues in the Hinge Region

TNT 146(293) and TNT 146(CHO) were produced by point mutations of cysteine residue at position 226 to serine and cysteine residue at position 229 to serine (C226S/C229S, EU numbering scheme), thus removing cysteine residues in the SAP-Fc hinge region (Table 1).

Modification of the SAP-Fc Using the "Knob-Hole" Method to Generate the Fc Region TNT 147(293), TNT 148(293), and TNT 148(CHO) were produced by modifying the SAP-Fc using the "knob-hole" method to generate the Fc region (Table 1). The knob mutant was produced by point mutation of threonine at positon 336 to tryptophan (T366W, EU numbering scheme). The hole mutant was produced by point mutation of threonine at position 366 to serine, leucine at position 368 to alanine, and tyrosine at position 407 to valine (T366S/L368A/Y407V, EU numbering scheme).

Modification of the SAP-Fc to Remove the Glycosylation Site in the SAP

TNT 151(293) and TNT 151(CHO) were produced by modifying the SAP-Fc to remove the glycosylation site in the SAP (Table 1). The aglycosylated SAP was produced by point mutation of asparagine at position 32 to serine and asparagine at position 110 to serine (N32S/N110S, numbered from first amino acid of SAP).

Modification of the SAP-Fc Using the "Knob-Hole" Method to Generate the Fe Region and to Remove the Glycosylation Site in the SAP TNT 152(293) and TNT 152(CHO) were produced by modifying the SAP-Fc to remove the glycosylation site in the SAP and using the "knob-hole" method to generate the Fc region (Table 1). The aglycosylated SAP and "knob-hole" Fc region were produced as described above.

Example 3. Production of SAP-Fc and its Modified Proteins

Production of SAP-Fc Constructs

The level of production of the recombinant SAP-Fc protein was assayed by ELISA. Firstly, MaxiSorp™ plates (NUNC) were coated with an anti-human IgG primary antibody (1 µg/ml, Beckman Coulter) overnight at 4° C. After 3 washes with PBS/0.05% tween-20, 50 µl of the samples diluted in complete medium were incubated for 2 hrs at 37° C. At the same time, a standard range of human IgG diluted in complete medium was incubated. After 3 washes, an anti-IgG antibody (Beckman Coulter) coupled to alkaline phosphatase (1 µg/ml) was added and incubated for 1 hr 30 min at 37° C. After a final series of washing, a volume of 100 µl of the alkaline phosphatase substrate was added and the reaction was then stopped after a few minutes using 3M NaOH. The plate was read by spectrometry at 405 nm.

The SAP-Fc fusion protein obtained was then purified by affinity chromatography on an ÄKTA$_{FPLC}$ system (GE Healthcare) using protein A affinity columns (Pierce) owing to the strong affinity of protein A for the Fc segments and owing to the presence of Fc region fragments in the chimeric proteins according to the invention. The UV detector located downstream of the column makes it possible to monitor the progression; when the absorption of the non-retained phase descends to a threshold value, the protein was eluted with 0.1 M glycine at pH 2.6. The various fractions were collected according to the chromatogram peaks. The eluates obtained were then neutralized with Tris at pH 8.8.

The purified protein was concentrated by means of Amicon® Ultra4 30 k filters (Millipore), which make it possible to eliminate molecules having a size less than 30 kDa. The solutions were placed in the filters and centrifuged at 4000 g for the time required to obtain the desired volume and the desired concentration.

The purified proteins (or culture supernatants) were detected by Western blotting using denaturing gel. The proteins were mixed with a volume of loading buffer containing β-mercaptoethanol (Bio Rad) and boiled for 5 min. They were then migrated by electrophoresis on a polyacrylamide gel (SDS-PAGE) composed of a stacking phase at 7.5% and a separating phase at 10%. The proteins were then transferred onto a PVDF membrane and saturated with 5% milk. They were then incubated for 1 hr at ambient temperature in the presence of the mouse anti-SAP (Abeam) or anti-IgG antibody coupled to HRP (BECKMAN COULTER®) (1 µg/ml). The anti-SAP antibody was revealed with a goat anti-mouse IgG secondary antibody coupled to HRP (SANTA CRUZ®) (0.2 µg/ml). The chemiluminescence reaction was triggered by adding the ECL substrate (PIERCE®) and revealed on an autoradiographic film (KODAK®).

The purified proteins (or culture supernatants) were also detected by Western blotting using semi-native gel. The proteins were mixed with a volume of loading buffer without β-mercaptoethanol and then migrated in an SDS-12% PAGE gel. The rest of the protocol is the same as for the denaturing gel.

Figure 16A:
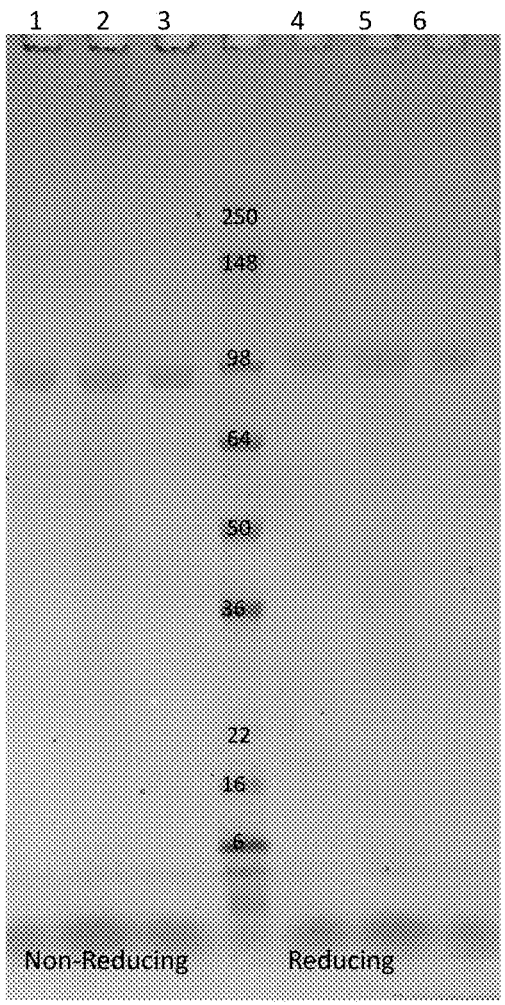
FIG. 16A and FIG. 16B shows SDS PAGE gels of purified SAP-Fc constructions.
Figure 16B:
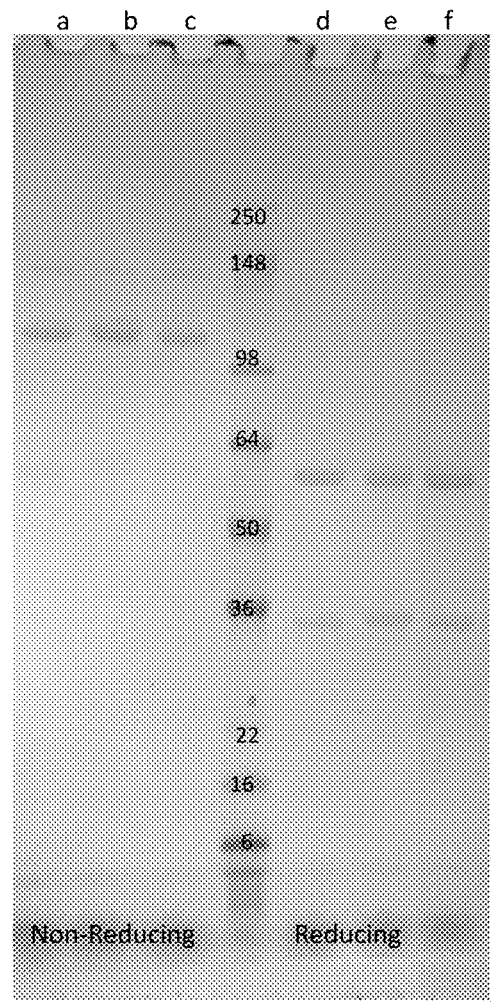

FIG. 16A and FIG. 16B shows SDS PAGE gels of the purified fusion proteins. For these experiments, TNT 146, TNT 147, TNT 148, TNT 155, and TNT 160 were purified through a two-step purification. TNT 151 was purified through a single Protein A purification step.

Example 4. Binding of Modified SAP-Fc to Fibrils

SAP-Fc and SAP-scFc binding to fibrils and extracts was studied by ELISA assay.

Using a Europium-linked immunosorbent assay (Eu-LISA) method for humanized IgG, a suspension of rVλ6Wil fibrils (sonicated) at 0.83 µM was prepared in phosphate buffered saline (PBS). The fibrils were coated onto the wells of a 96-well microplate by adding 50 µL to each well. The plate was dried at 37° C overnight. The wells of the microplate were blocked by addition of Superblock in tris-buffered saline (TBS) with 2 mM calcium chloride (Ca) (Thermofisher) (SBT) using 200 µL/well and left at 37° C for 1 hr. The primary (test) SAP-Fc fusion protein, humanized immunoglobulin, hIgG1 or c11-1F4 were added. The plate was incubated for 1 hr at 37° C. After a wash step (plates were washed 3× using TBS/Ca+0.05% tween 20), the secondary antibody was added—a 1:3000 dilution of biotinylated goat anti-human IgG (Sigma) in SBTT at 100 □L/well. The plate was incubated for 1 hr at 37□ C. After another wash step, 100 □L/well of a 1:1000 dilution of europium/streptavidin (Perkin Elmer) in SBT was added. The plate was incubated for 1 hr at 37□ C. After a final wash step, 100 □L/well of europium enhancement solution (Perkin Elmer) was added. Time-resolved fluorescence emission was read using a microplate reader (Wallac).

Figure 8A:
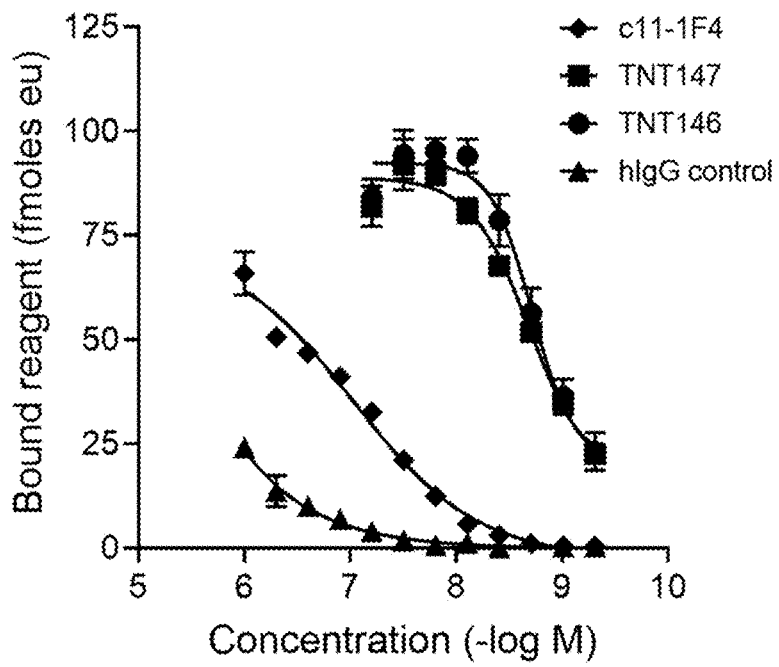
FIG. 8A shows an ELISA assay of hIgG (control), c11-1F4, TNT 146(293), and TNT 147(293) binding to synthetic rVλ6Wil fibrils.
Figure 8B:
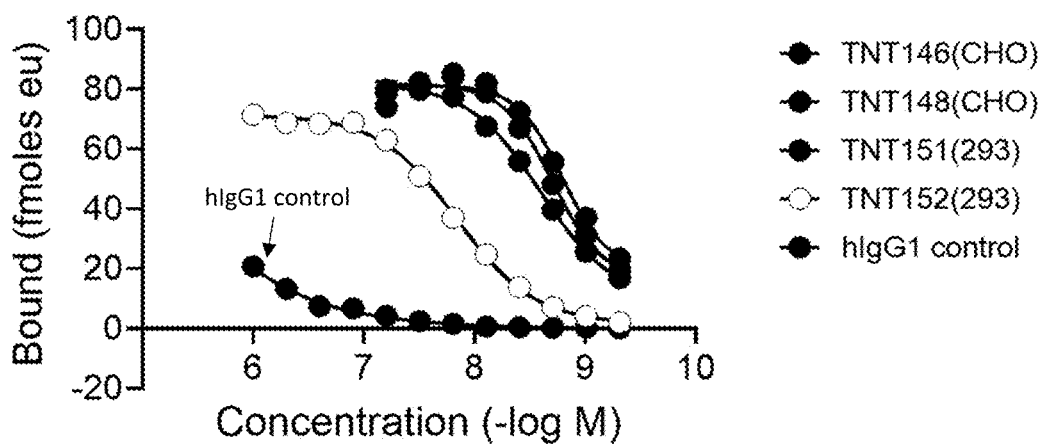
FIG. 8B shows ELISA assay of hIgG (control), TNT 146(CHO), TNT 148(CHO), TNT 151(293), and TNT 152(293) binding to synthetic rVλ6Wil fibrils.
Figure 9A:
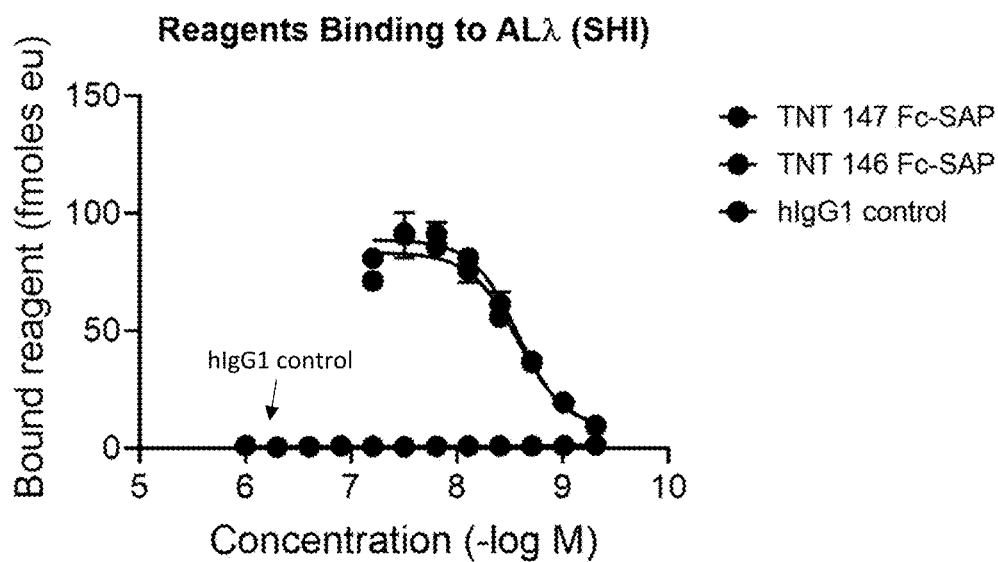
FIG. 9A and FIG. 9B show an ELISA assay of hIgG (control), TNT 146(293), and TNT 147(293) binding to SHI ALλ and Per125 wtATTR.
Figure 9B:
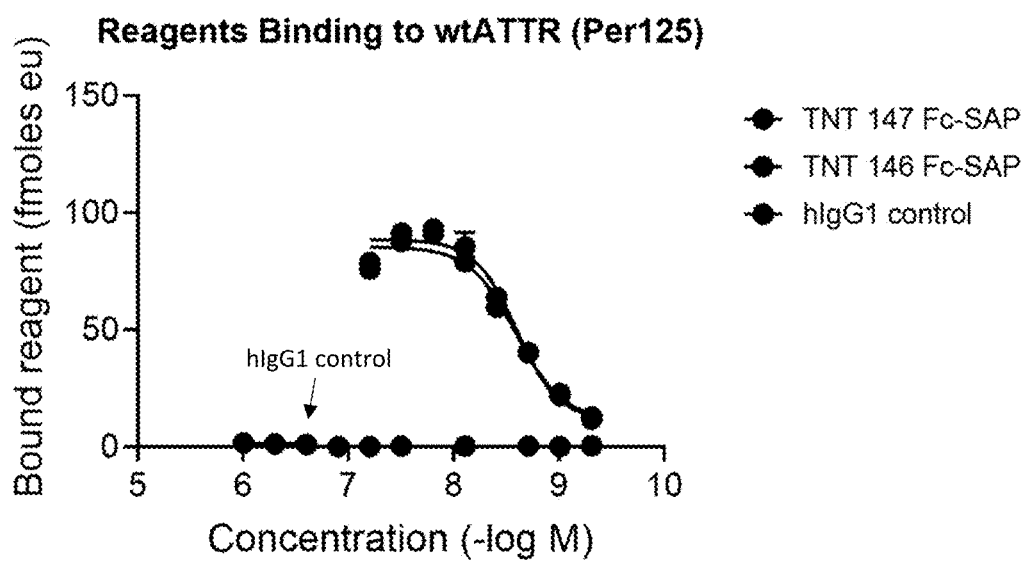
Figure 10A:
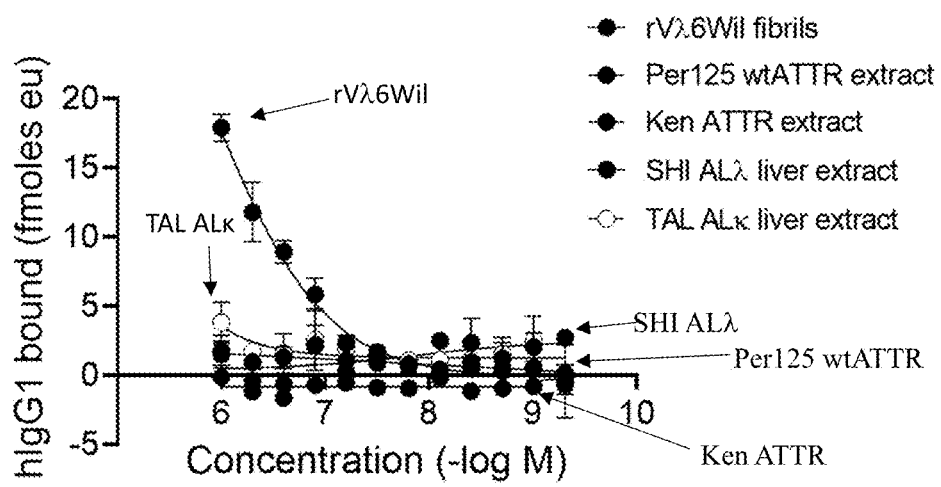
FIG. 10A shows an ELISA assay of IgG1 binding to rVλ6Wil fibrils, Per125 wtATTR extract, Ken ATTR extract, SHI ALλ liver extract, and TAL ALκ liver extract.
Figure 10B:
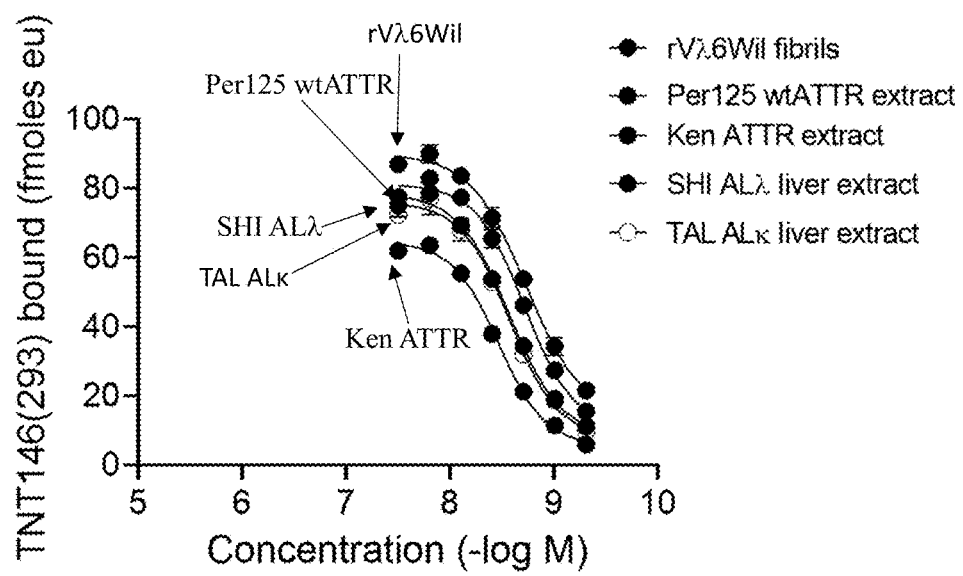
FIG. 10B shows an ELISA assay of TNT 146(293) binding to rVλ6Wil fibrils, Per125 wtATTR extract, Ken ATTR extract, SHI ALλ liver extract, and TAL ALκ liver extract.
Figure 10C:
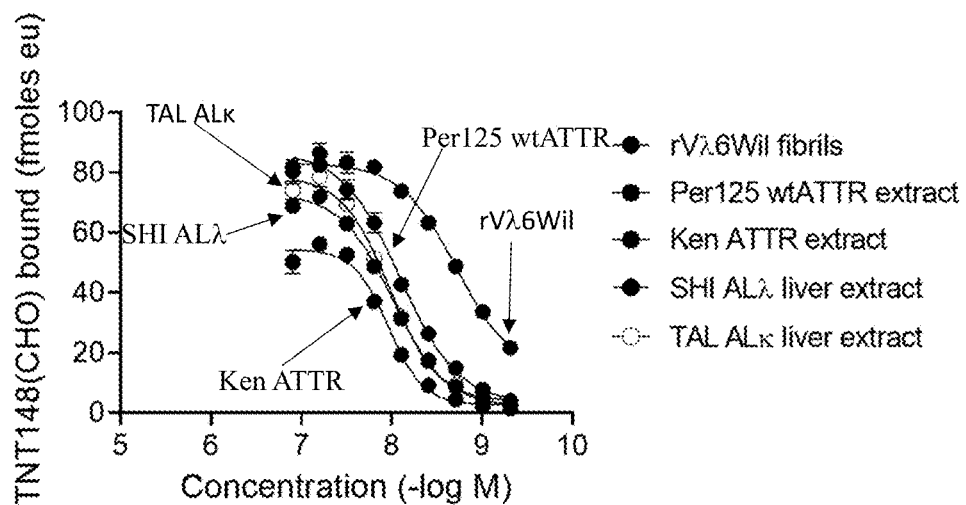
FIG. 10C shows ELISA assay of TNT 148(CHO) binding to rVλ6Wil fibrils, Per125 wtATTR extract, Ken ATTR extract, SHI ALλ liver extract, and TAL ALκ liver extract.
Figure 10D:
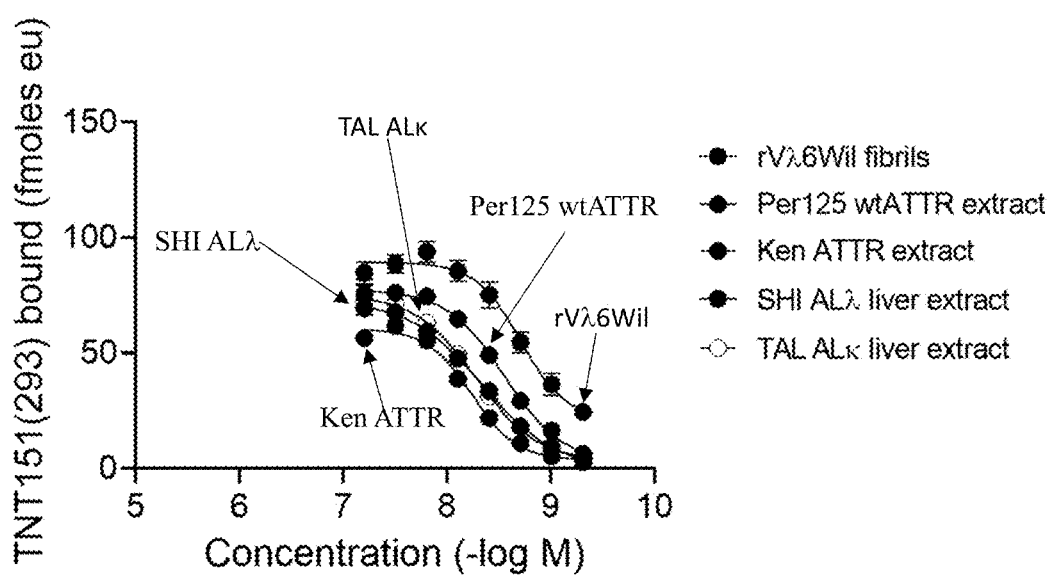
FIG. 10D shows an ELISA assay of TNT 151(293) binding to rVλ6Wil fibrils, Per125 wtATTR extract, Ken ATTR extract, SHI ALλ liver extract, and TAL ALκ liver extract.
Figure 10E:
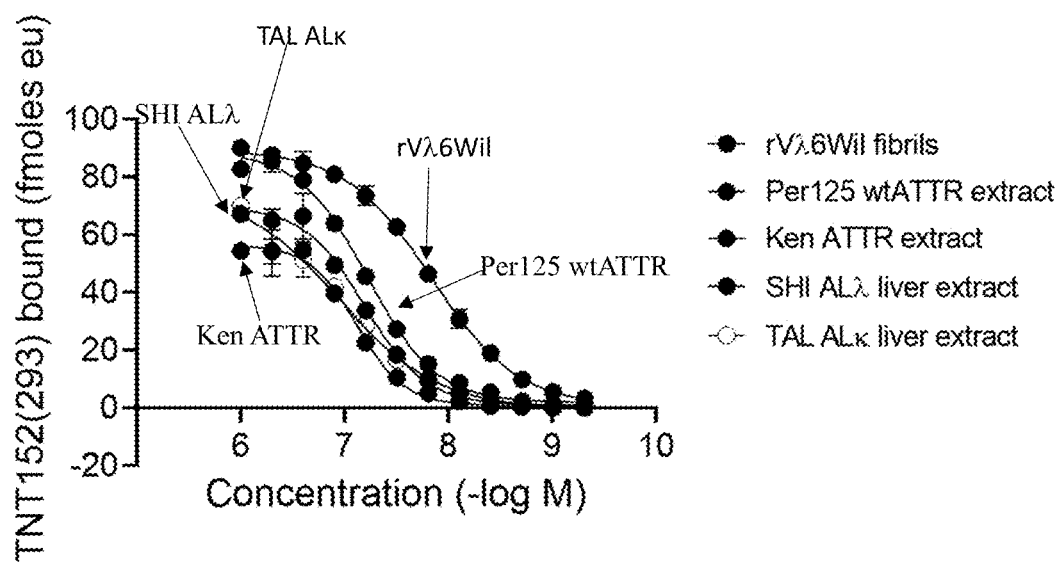
FIG. 10E shows ELISA assay of TNT 152(293) binding to rVλ6Wil fibrils, Per125 wtATTR extract, Ken ATTR extract, SHI ALλ liver extract, and TAL ALκ liver extract.

The result in FIG. 8A shows TNT 146(293) and TNT 147(293) supplied originally bind synthetic rVλ6Wil fibrils with affinity (EC50) greater than hIgG1 control and c11-1F4 in an ELISA assay. FIG. 8B shows TNT 146(CHO), TNT 148(CHO), TNT 151(293) bind to rVλ6Wil fibrils equally well, with the exception of TNT 152(293). The results in FIGS. 9A-9B show the knob-hole and cys-mutated versions of SAP-Fc retain amyloid reactivity in vitro.

The results in FIGS. 10A-10E and Table 4 show that all constructs exhibit EC50 values in the range of 1-10 nM, except TNT 152(293) and TNT 148(CHO). The highest binding to wtATTR extract was seen with the SAP-scFc reagents TNT 146(293), TNT 146(CHO), TNT 151(293) (Table 4). Aglycosylation of the SAP, in the context of the SAP-scFc retains amyloid reactivity in vitro with similar EC50, except for TNT 152(293), which has a higher EC50 for amyloid extracts than hIgG1-peptide fusions (FIG. 8B and Table 4).

For the pulldown assay twenty-five microliters of 1 mg/mL AL extract, or synthetic rVλ6Wil variable domain fibrils (REF) were centrifuged in a 0.5 mL microfuge tube at 21,000×g for 5 min. The supernatant was discarded and the pellet was resuspended in 200 μl of PBS with 0.05% tween-20 (PBST). 125I-p5+14 (~100,000 counts per minute (CPM); ~5 ng peptide) or 125I-labeled SAP-Fc fusion proteins were added to the suspension. The mixture was rotated at RT for 1 h. Samples were then centrifuged twice at 15,000×g for 10 min. Supernatants and pellets were separated after each step and the radioactivity in each was measured using a Cobra II gamma counter (Perkin Elmer) with a 1 min acquisition. The percentage of 125I-p5+14 or 125I-labeled SAP-Fc fusion proteins bound to pellet was determined as follows:

$$\text{Pellet } CPM/(\text{Pellet } CPM + \text{Supernatant } CPM) \times 100$$

In the pulldown assay, $^{125}$I-labeled TNT 146 and TNT 147 showed weak binding to substrates with EC50 in the nanomolar range (Table 5), indicating that oxidative radioiodination may negatively impact the product, resulting in loss of activity; amyloid extract presented as soluble material may present different binding sites; and higher concentrations of reagent may drive binding in the ELISA format.

TABLE 4

SAP-Fc and SAP-scFc binding to fibrils and extracts in ELISA assay

| | | Substrate | | | | | |
|---|---|---|---|---|---|---|---|
| | | rVλ6Wil fibrils | rVλ6Wil fibrils | Per125 wtATTR extract | Ken hATTR extract | SHI ALλ liver extract | TAL ALκ liver extract |
| TNT146 (293) | LogEC50 | | 8.375 | 8.717 | 8.471 | 8.575 | 8.574 |
| | EC50 | | 1.84E−09 | 1.92E−09 | 3.38E−09 | 2.66E−09 | 2.67E−09 |
| | MAX | | 89.9 | 81.15 | 64.55 | 78.52 | 76.03 |
| TNT146 (CHO) | LogEC50 | 8.794 | 8.841 | 8.772 | 8.508 | 8.63 | 8.574 |
| | EC50 | 1.61E−09 | 1.44E−09 | 1.69E−09 | 3.10E−09 | 2.34E−09 | 2.67E−09 |
| | MAX | 81.28 | 79.02 | 71.18 | 51.72 | 57.21 | 66.69 |
| TNT148 (CHO) | LogEC50 | 8.596 | 8.717 | 8.094 | 7.966 | 8.014 | 7.98 |
| | EC50 | 2.54E−09 | 1.92E−09 | 8.05E−09 | 1.08E−08 | 9.68E−09 | 1.05E−09 |
| | MAX | 81.81 | 83.07 | 87.02 | 54.48 | 73.11 | 78.85 |
| TNT151(293) | LogEC50 | 8.708 | 8.71 | 8.553 | 8.242 | 8.348 | 8.243 |
| | EC50 | 1.96E−09 | 1.95E−09 | 2.80E−09 | 5.73E−09 | 4.49E−09 | 5.71E−09 |
| | MAX | 81.71 | 89.31 | 77.42 | 60.51 | 72.71 | 75.21 |
| TNT152(293) | LogEC50 | 7.843 | 7.839 | 7.221 | 7.119 | 7.195 | 6.956 |
| | EC50 | 1.44E−09 | 1.45E−09 | 6.01E−09 | 7.60E−09 | 6.38E−09 | 1.11E−09 |
| | MAX | 71.35 | 89.33 | 88.86 | 56.48 | 69.75 | 75.39 |

The binding of SAP-Fc fusions to fibrils and extracts was also tested in a pulldown assay. Synthetic amyloid fibrils from rVλ6Wil were prepared as follows: a 1 mL-volume containing 1 mg/mL of monomer in phosphate-buffered saline (PBS), 0.01% w/v NaN3, pH7.5, was filtered through a 0.2 mm pore-sized filter, added to a 15 mL conical polypropylene tube (BD BioSciences, Bedford, MA) and shaken at a 45° angle at 225 rpm for 3-5 d at 37° C. until the reaction mixture became opaque.

Purified human amyloid tissue extracts were prepared using autopsy-derived tissues from patients with light chain-(AL) or transthyretin-associated (ATTR) amyloidosis using the water flotation method as described by Pras et al., J Exp Med (1969) 130(4):777-795 without modification. Purified amyloid material isolated in the water wash, and amyloid rich pellet, was collected and stored lyophilized at RT until used.

TABLE 5

TNT146 and TNT147 binding to fibrils and extracts in pulldown assay

| | TNT146 | TNT147 | IgG ctrl |
|---|---|---|---|
| rVλ6Wil synthetic fibrils | 67.00** | 61.97** | |
| Aβ(1-40) fibrils | | | |
| hIAPP fibril | | | |
| Vκ4(LEN(1-22) beads | | | |
| HIG ALκ1 | | | |
| TAL ALκ | 1.76 | 1.10 | 0.10 |
| SHI ALλ | 1.90 | 1.51 | 0.17 |
| TYL ALλ | | | |
| CAB ALκ4 | | | |
| SNO hATTR | | | |
| KEN hATTR | 1.50 | 0.71 | 0.15 |
| wtATTR - PER125 | 2.64 | 1.66 | 0.13 |
| wtATTR - PER253 | | | |

TABLE 5-continued

TNT146 and TNT147 binding to fibrils and extracts in pulldown assay

| | TNT146 | TNT147 | IgG ctrl |
|---|---|---|---|
| AA mose liver homog. | | | |
| WT mouse liver homog. | | | |

Example 5. Biodistribution of SAP-Fc in Mice

AA Amyloidosis Mice Model

The AA amyloidosis mice is a line of mice that express the human IL6 (huIL6) protein from a stably inserted transgene. The B6(C)-Tg(H2-Ld-IL-6)Kish (H2/huIL-6) strain was derived at the National Institutes of Health by introgressive backcrossing of the original H2-Ld-IL-6 Tg C57BL/6 transgenic mice onto the Balb/c background for more than 20 generations (Kovalchuk et al., PNAS (2002) 99:1509-1514). These mice constitutively express the huIL6 transgene under the control of the mouse major histocompatibility complex class 1 (H2-Ld) promoter. The transgene segregates with an autosomal pattern of Mendelian inheritance (Suematsu et al., PNAS (1992) 89:232-235). Because of the role of IL6 in maintenance of the inflammatory response and lymphocyte proliferation during the immune response, early generations of these transgenic animals had high sAA levels and an extensive lymphocytosis with development of polyclonal plasma cell proliferation in 56% of mice at 18 mo of age (Kovalchuk et al., PNAS (2002) 99:1509-1514). Human IL6 serum levels in the early generations of this transgenic line were 0.5 to 1 ng/mL; however, backcrossed Balb/c mice bred in our facility for approximately 2 y had approximately 300-fold higher levels of circulating huIL6 levels at 8 wk of age (0.3 to 1 µg/mL) (Solomon et al., Am J Pathol (1999) 154:1267-12724). In response to the proinflammatory huIL6 cytokine, the mice experience a chronic inflammatory state that results in increased concentrations of circulating sAA-conjugated high-density lipoprotein. The spontaneous onset of AA amyloidosis in these mice typically occurred at age 5 mo, presenting first as perifollicular deposits in the spleen only detectable histologically by biopsy (Solomon et al., Am J Pathol (1999) 154:1267-12724). Over the course of the next 3 to 4 mo, amyloid was detected in the periportal vasculature and sinusoids within the liver, tongue, heart and intestinal villi, as well as renal interstitium, glomerulae, and papilla. In addition, cast nephropathy was commonly observed, as was extramedullary hematopoiesis and splenomegaly due to amyloidosis or lymphoid hyperplasia (or both) resulting from the elevated IL6 concentrations.

The nature of the amyloid in H2/huIL-6 mice was documented immunohistochemically by using AA-specific monoclonal antibodies (Solomon et al., Am J Pathol (1999) 154:1267-12724). In addition, liquid chromatography-coupled mass spectrometry showed that isolated tissue-derived AA fibrils were comprised of a truncated form of sAA containing the first 77 N-terminal amino acids (residues 1 to 77) (Solomon et al., Am J Pathol (1999) 154:1267-12724). No evidence of apolipoproteins AI and AII or immunoglobulin light chain has been found during immunohistochemical examination and liquid chromatography-coupled mass spectrometry of the amyloid extracted from these mice.

Biodistribution of SAP-Fc was studied in wild type (WT) mice and AA amyloidosis mice model.

The biodistribution of SAP-Fc was studied in wild type (WT) mice and AA amyloidosis mice model by tissue micro-autoradiography. The AA amyloidosis mice model was generated by IV administration of 10 mg of isolated amyloid enhancing factor (AEF, Axelrad et al., Lab Invest (1982)47: 139-146.) in 100 mL of sterile phosphate-buffered saline (PBS) in H2-Ld-huIL-6 Tg Balb/c transgenic mice that constitutively express the human interleukin-6 transgene. Mice used in these studies were 4-6 wk post induction. The AA mice model is characterized by interstitial cardiac amyloid deposition, extensive sinusoidal amyloid deposits in liver, initial and massive perifollicular amyloid deposits in spleen, and later amyloid deposits in pancreas, kidney, adrenal glands, and intestine.

AA or WT mice were injected with 10 µg 125I labeled TNT 146(293) and TNT 147(293), then euthanized at 48 h post injection. Samples of spleen, pancreas, left and right kidney, liver, heart, muscle, stomach, upper and lower intestine, and lung tissue were harvested from WT and AA mice after euthanasia. Each sample was placed into a tared plastic vial and weighed, and the 125I radioactivity was measured by using an automated Wizard 3 gamma counter (1480 Wallac Gamma Counter, PERKIN ELMER®). The biodistribution data were expressed as percentage of injected dose per gram of tissue (% ID/g). In addition, samples of each tissue were fixed in 10% buffered formalin for 24 h and embedded in paraffin for histology and autoradiography. For autoradiography, 4- to 6-µm thick sections were cut from formalin-fixed, paraffin-embedded blocks onto Plus microscope slides (FISHER SCIENTIFIC®), dipped in NTB2 emulsion (EASTMAN KODAK®), stored in the dark, and developed after a 96-h exposure. Each section was counterstained with hematoxylin. Alternatively, AA or WT mice were injected with 500 µg unlabeled TNT 147(293) then euthanized at 48 h post injection. The samples of each tissue were fixed in 10% buffered formalin for 24 h and embedded in paraffin. 4- to 6-µm thick sections were cut from formalin-fixed, paraffin-embedded blocks onto Plus microscope slides (FISHER SCIENTIFIC®), then the sections were stained using anti-human Fc. Tissue amyloid deposits were identified microscopically in consecutive tissue sections viewed under cross-polarized illumination after staining with alkaline Congo red. All tissue sections were examined by light microscopy (DM500, LEICA®) fitted with cross-polarizing filters (for the detection of Congo red birefringence). Digital microscopic images were acquired by using a cooled charge-coupled device camera (SPOT, DIAGNOSTIC INSTRUMENTS®).

Figure 11A:
FIG. 11A shows amyloid deposition stained by Congo red (left column) and autoradiography of $^{125}$I labeled TNT 146(293) in AA mouse injected with 10 μg SAP-Fc 146 (right column).
Figure 11A:
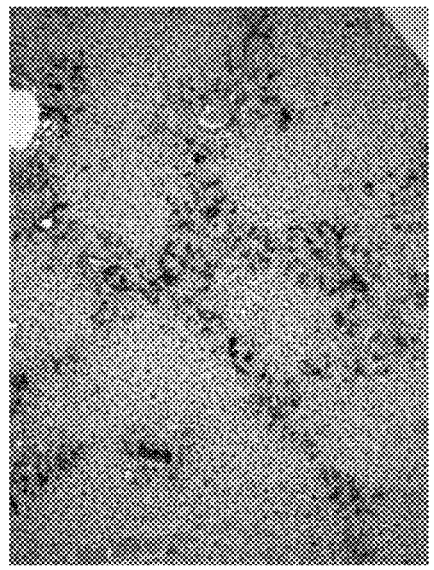
Figure 11A:
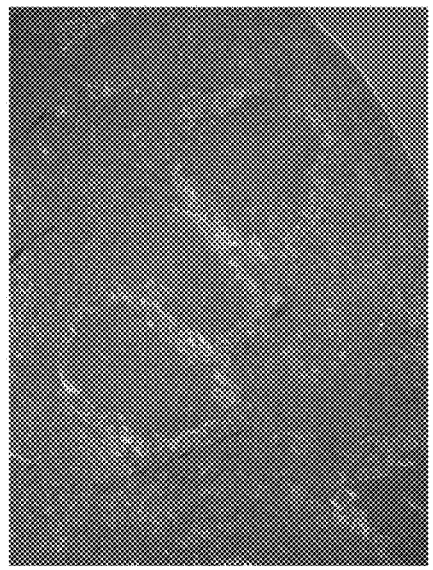
Figure 11A:
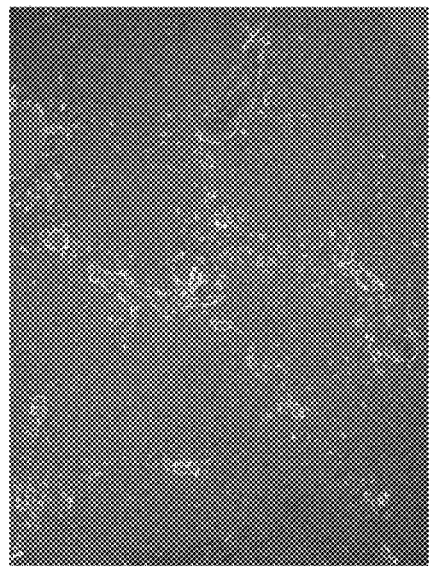
Figure 11B:
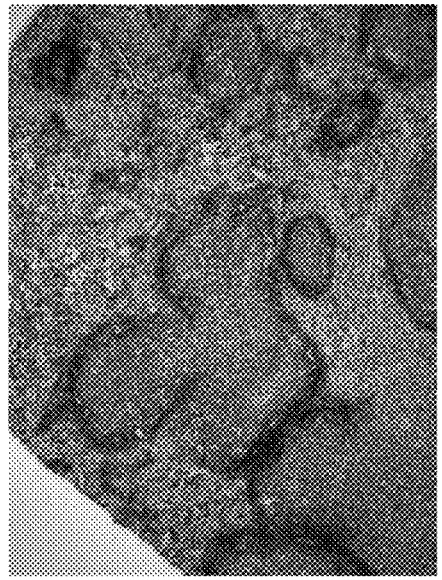
FIG. 11B shows amyloid deposition stained by Congo red (left column) and autoradiography of $^{125}$I labeled TNT 147(293) in AA mouse injected with 10 SAP-Fc 147 (right column).
Figure 11B:
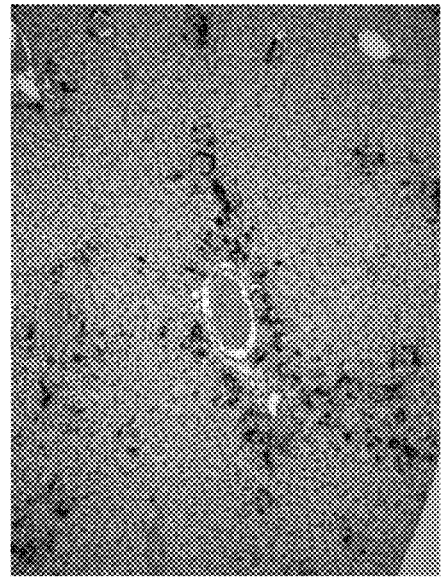
Figure 11B:
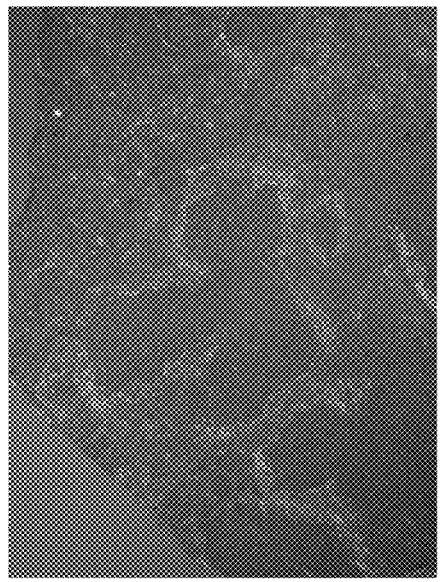
Figure 11B:
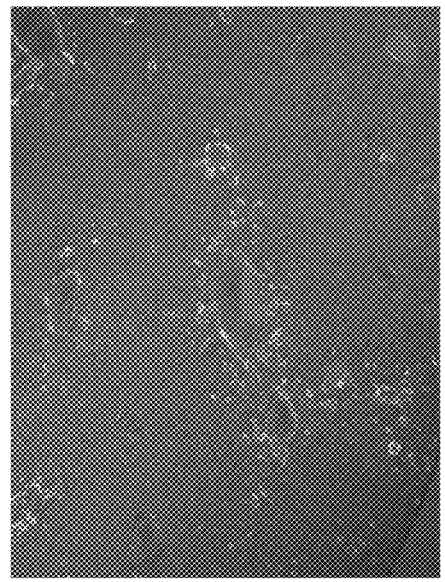
Figure 11C:
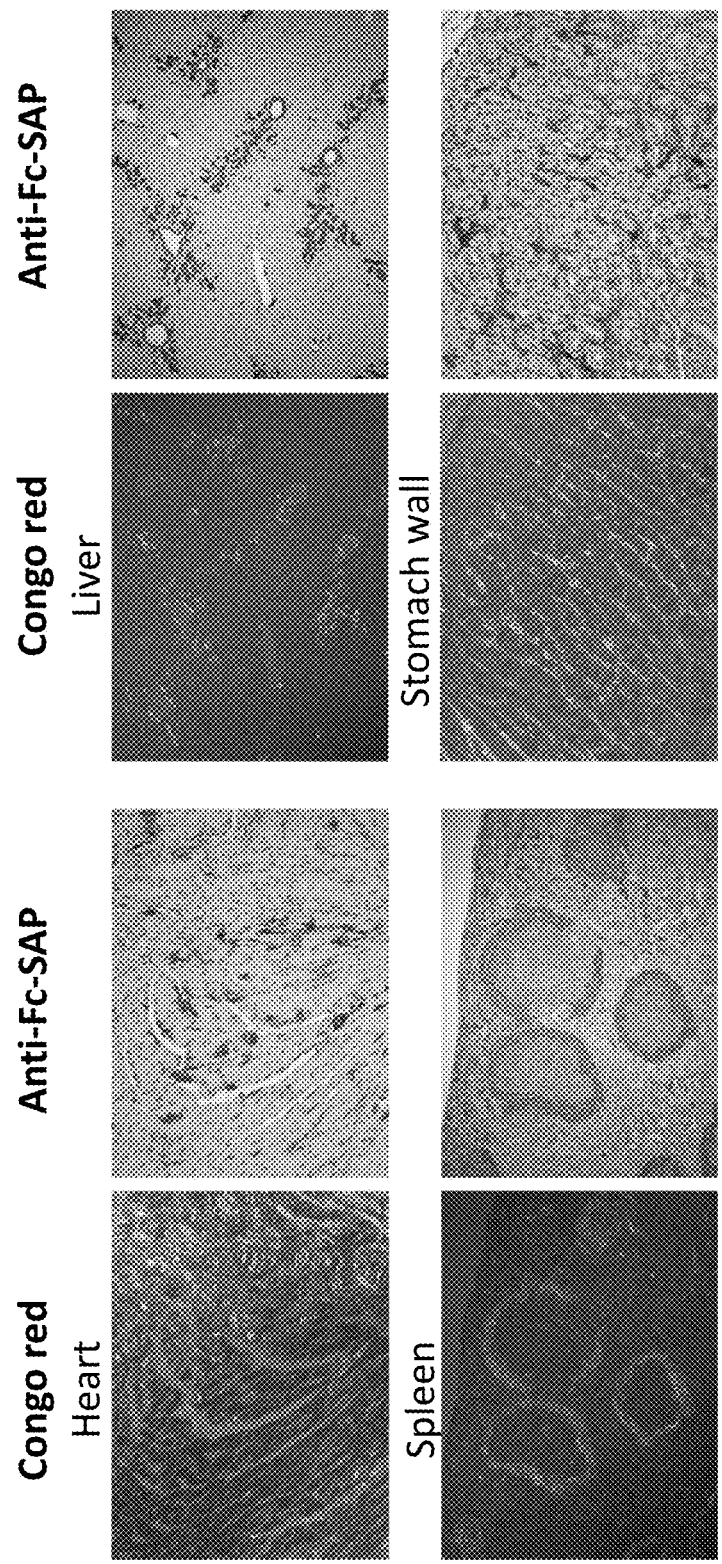
FIG. 11C shows amyloid deposition stained by Congo red (first and third column) and anti-human Fc immunostaining of AA mouse injected with 500 SAP-Fc 147 (second and forth column).

The results in FIGS. 11A-11C show TNT 146(293) and TNT 147(293) specifically bind AA amyloid in mice with systemic disease, both when they were radiolabeled with 125I and unlabeled. Specific binding of both TNT 146(293) and TNT 147(293) to amyloid deposits was evidenced in the scant AA deposits in the heart by autoradiography.

Figure 12A:
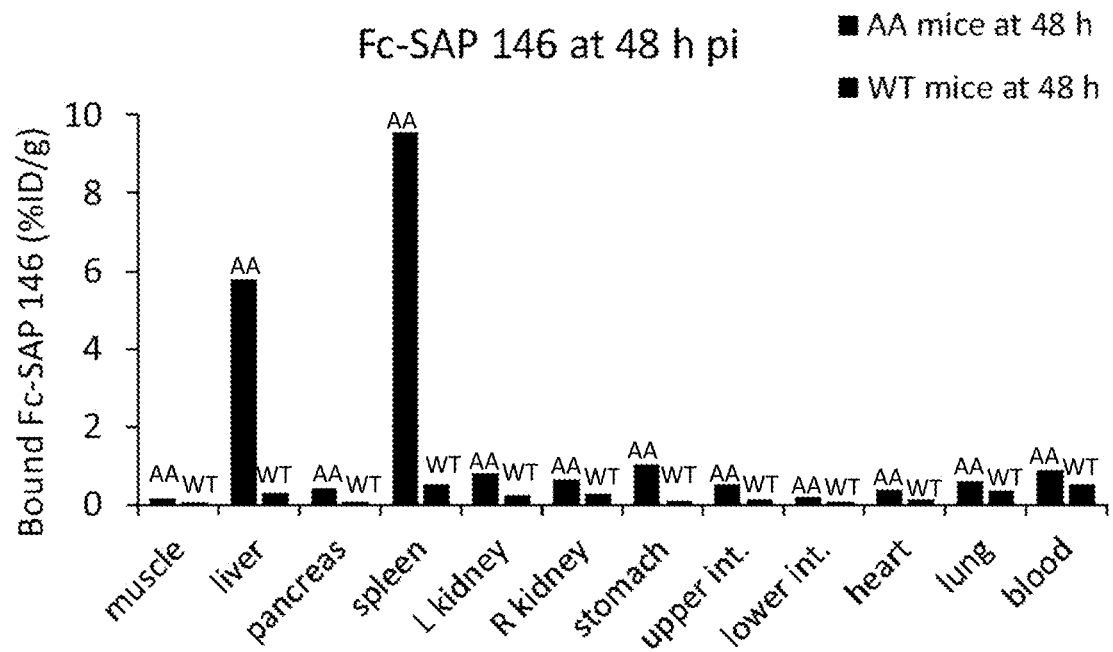
FIG. 12A and FIG. 12B show a comparison of SAP-Fc biodistribution in AA mice versus wild type (WT) mice.
Figure 12B:
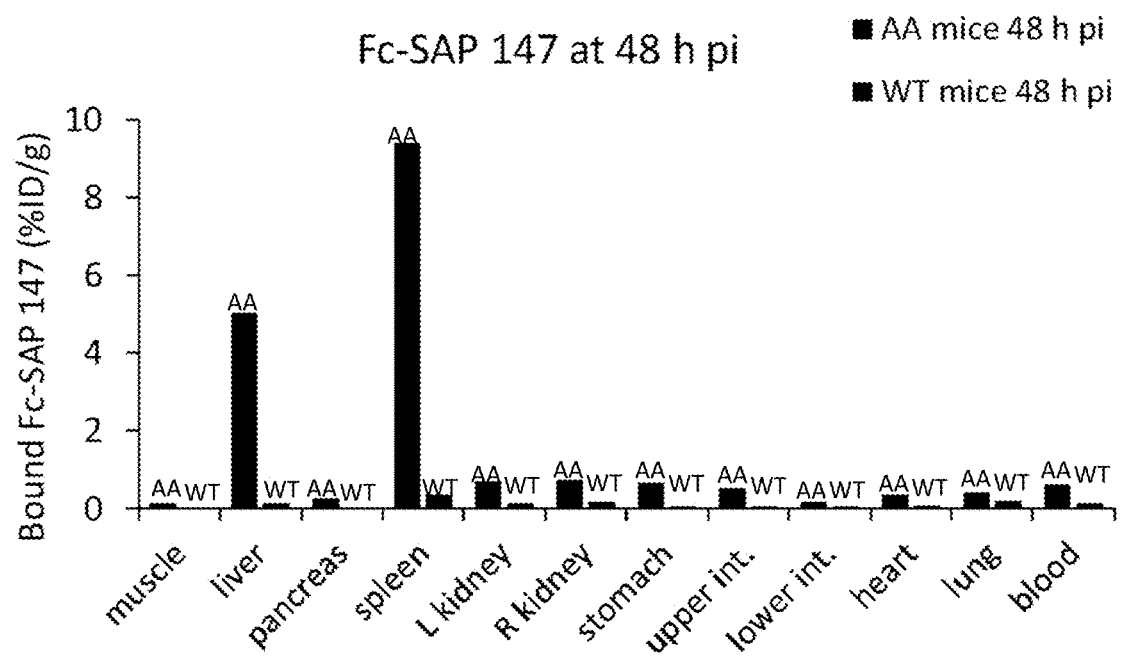

The results in FIGS. 12A-12B show 125I labeled TNT 146(293) and TNT 147(293) accumulated in liver and spleen in AA mice, and do not accumulate in amyloid-free tissues of WT mice.

Example 6. Multimerization Analysis of SAP-Fc Constructs

High avidity binding of SAP to amyloid is afforded by appropriate multimerization of the protein as pentamer or decamer. On the other hand, large and/or inappropriate aggregation of SAP-Fc may be cleared rapidly from the circulation, thus negatively impacting its PK and function.

As a result, analysis of the high order aggregation of SAP-Fc constructs is important for understanding their functions in vivo.

The multimerization and aggregation of SAP-Fc constructs were analyzed by size exclusion chromatography (SEC). A matrix appropriate for proteins with 10-1300 kDa molecular weight was used in this analysis. Commercial protein preparations were used as molecular weight standards. The estimated molecular weight for SAP-Fc monomer is about 75 kDa, the estimated molecular weight for SAP-Fc pentamer is about 375 kDa, and the estimated molecular weight for SAP-Fc decamer is about 750 kDa.

Figure 13:
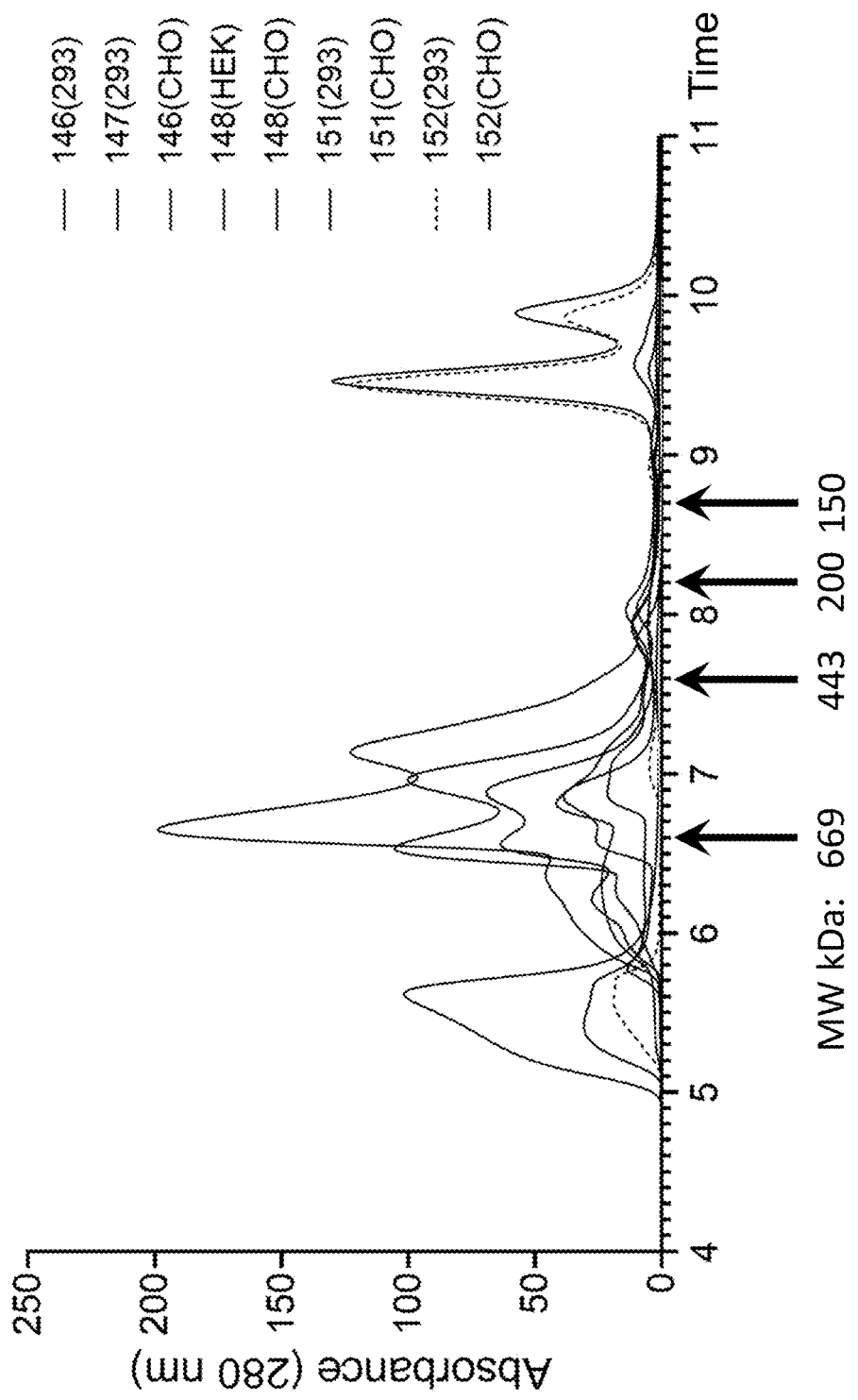
FIG. 13 shows SEC chromatograms of TNT 146(293), TNT 147(293), TNT 146(CHO), TNT 148(HEK), TNT 148(CHO), TNT 151(293), TNT 151(CHO), TNT 152(293), and TNT 152(CHO). Arrows on the bottom indicate time of elution for 150 kDa, 200 kDa, 443 kDa, and 669 kDa molecular weight standards.

The results in FIG. 13 show that the SAP-Fc constructs all had different mutimerization structures, while TNT 146 (293) and TNT 147(293) were the most homogeneous. Production in CHO versus HEK-293 cells greatly influenced the mutimerization structures of TNT 151 and TNT 152 constructs (FIG. 13).

Figure 14A:
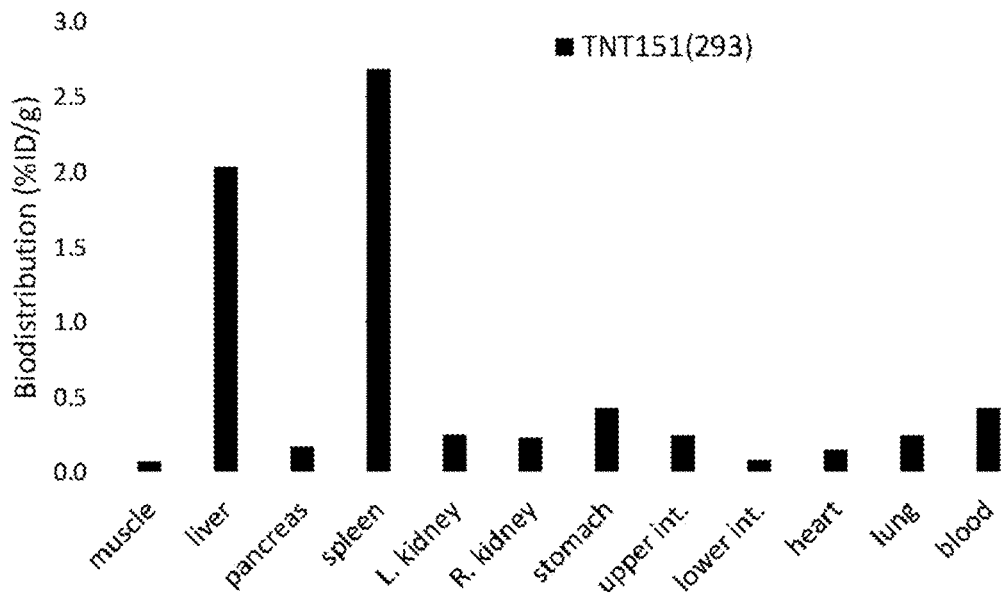
FIG. 14A shows biodistribution of TNT 151(293) in AA mice.
Figure 14B:
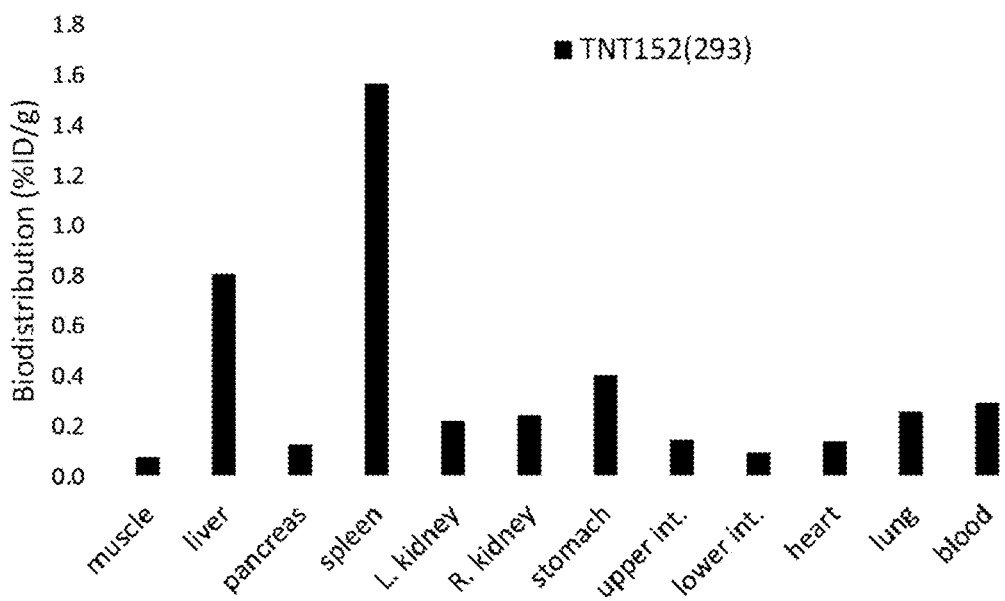
FIG. 14B shows biodistribution of TNT 152(293) in AA mice.
Figure 14C:
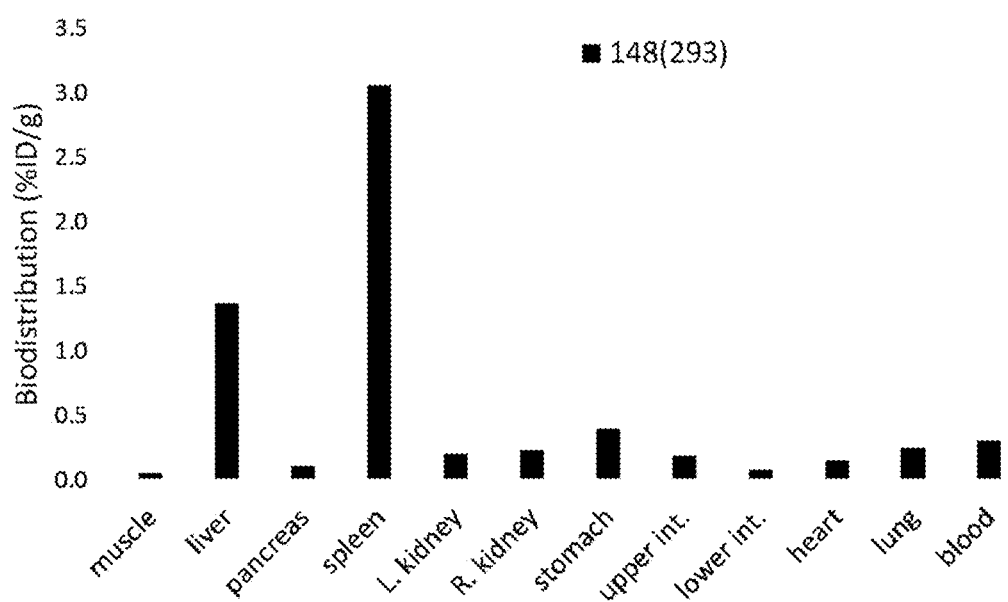
FIG. 14C shows biodistribution of TNT 148(293) in AA mice.

Uptake and biodistribution of these constructs in mice were also compared. TNT 146(293) and TNT 147(293) both showed about 10% distribution in spleen (FIGS. 12A-12B). Other constructs showed less distribution in spleen: TNT 151(293) showed about 2.5% distribution in spleen, which was 4 times less than TNT 146(293) and TNT 147(293) (FIG. 14A); TNT 152(293) showed about 2% distribution in spleen, which was 5 times less than TNT 146(293) and TNT 147(293) (FIG. 14B); TNT 148(293) showed about 3% distribution in spleen, which was 3.3 times less than TNT 146(293) and TNT 147(293) (FIG. 14C). Taken together with the SEC chromatograms of the mutimerization analysis, these results indicate the dimer peak between 450-669 kDa correlates with optimal SAP-Fc uptake in AA mice (FIGS. 12A-12B, 14A-14C, and 13).

Example 7. Phagocytosis of rVλ6Wil Fibrils by THP1 Cells

Phagocytosis was studied using the pHrodo red-labeled rVλ6Wil fibrils system.

For assays of solid phase Wil fibril uptake, 24-well tissue culture plates are coated with Type I rat collagen (75 μg/ml in 20 mM acetic acid, 0.4 ml) for 2 hours at room temperature, washed with 0.5 ml PBS, and coated with 20 μg/well of pHrodo red-labeled rVλ6 fibrils (30% labeled fraction) overnight in 0.5 ml of PBS at 4° C. The wells are washed with 0.5 ml PBS, and 0.5 ml serum-free phenol red-free RPMI 1640 is added. Antibody opsonins or SAP-Fc proteins are added, followed by immediate addition of RAW 264.7 or uninduced THP-1 cells in serum-free, phenol red-free RPMI 1640 ($1.2\times10^6$ in 0.5 ml) for a 4 hour incubation at 37° C. For uptake measurement, cells from each well are transferred to triplicate wells of a black plastic/clear bottom 96-well microplate (Corning) for fluorescence measurement in a BioTek SynergyHT-1 microplate reader at 530/25 nm excitation and 645/40 nm emission in well-scanning mode. Background readings from wells incubated in 1 ml of medium alone are subtracted to give relative fluorescence units.

Figure 15:
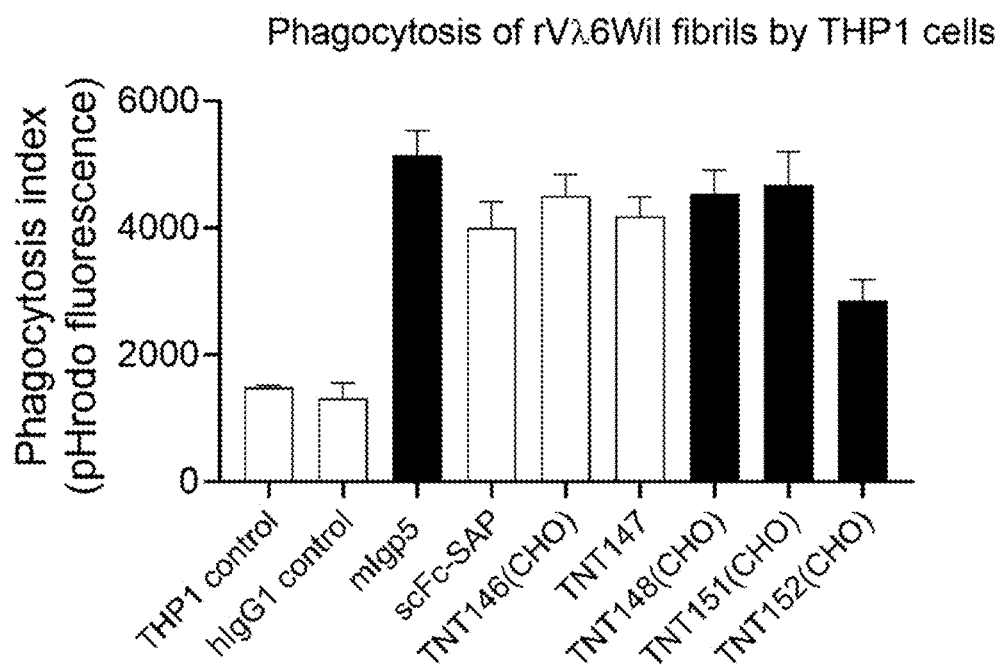
FIG. 15 shows phagocytosis of rVλ6Wil fibrils by THP1 cells without treatment (THP1 control), treated with hIgG1 (hIgG1 control), mlgp5 (a murine antibody-peptide fusion), SAP-Fc TNT 146(CHO), TNT 147(239) (labeled as TNT 147), TNT 148(CHO), TNT 151(CHO), and TNT 152 (CHO).

The result in FIG. 15 shows SAP-Fc TNT 146(CHO), TNT 147(239), TNT 148(CHO), and TNT 151(CHO) serve as excellent opsonizing agents, while TNT 152(CHO) was the least effective reagent, which is consistent with its weaker binding to rVλ6Wil fibril.

Example 8. Phase 0 Biodistribution Study

AUR03 is an SAP-Fc radiolabeled with 124I using Iodogen tube method used in this study. The objectives of the phase 0 study are to: 1) determine the biodistribution, including off-target binding and target engagement in patients with systemic amyloidosis; 2) determine if AUR03 engages target amyloid-laden organs such as heart and kidney; 3) determine if AUR03 binds amyloid-laden organs in both ATTR and AL patients; 4) differentiate AUR03 from other drugs by amyloid type or organs for development planning.

30 patients are recruited into two cohorts. 15 ATTR patients with evidence of cardiac involvement are recruited into cohort 1a; 15 AL patients with abdominothoracic organ involvement are recruited into cohort 1b. Patients in both cohorts receive one dose of 100 μg AUR03 and are then imaged at 2 days and 5 days post-injection at 1-2 clinical sites.

Pre- and post-injection blood is collected for CBC, ClinChem, NT-proBNP, and LDH studies. Blood samples are collected for PK determination, and radioactivity in blood samples is measured over 72 hours.

Example 9: In Vivo Phagocytosis

A batch of 12 mg human ALλ(SHI) amyloid, containing 10% pHrodo red labeled material, was preincubated with 600 μg of TNT 146 in tris-buffered saline with 2 mM CaCl2 for 30 min with mixing at room temperature (RT). The increase in fluorescence emission of fluorophore pHrodo red is associated with acidification of the amyloid during phagocytosis by macrophages and potentially neutrophils. Immunocompromised NU/NU (nude) mice (n=5) received 2 mg of human ALλ(SHI) as a subcutaneous injection in the left flank of the mouse. A control group of NU/NU mice (n=5) received a similar subcutaneous dose of 2 mg of human ALλ(SHI) without TNT 146 pretreatment. The fluorescence emitted by the pHrodo red fluorophore was monitored serially by optical imaging with the mice under 2% isoflurane anesthesia. Images were collected on days 1, 3, 8, 10, 12 and 14 post injection of the amyloid. On day 15 the mice were euthanized.

Figure 17A:
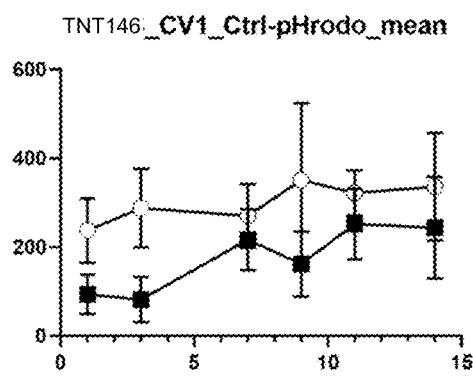
FIG. 17A and FIG. 17B show quantitation of pHrodo red fluorescence emission from optical imaging of mice with subcutaneous human ALλ amyloid.
Figure 17B:
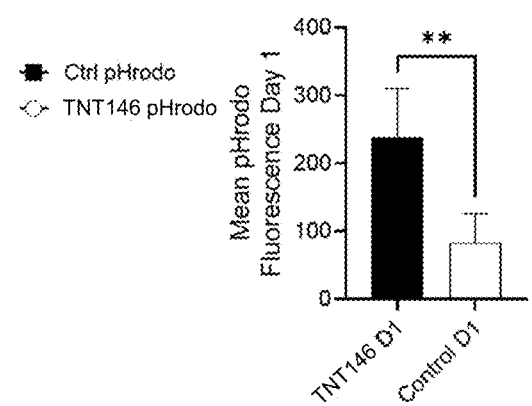
Figure 18A:
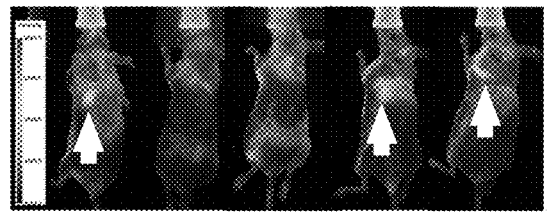
FIG. 18A and FIG. 18B show optical imaging of mice with pHrodo red-labeled human ALλ subcutaneous amyloid at day 14 post injection. Arrows indicate the location of the labeled amyloid.
Figure 18:
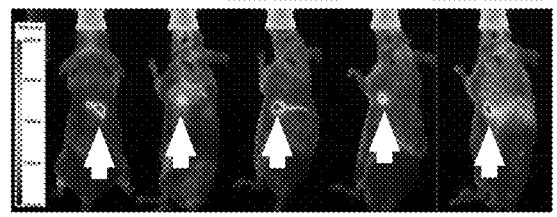

Quantitation of pHrodo red by optical imaging revealed an initial increase in the emission in TNT 146 treated mice, which was sustained throughout the course of the study (FIG. 17A). At day 1 (24 h post injection of the amyloid) the fluorescence emission to TNT 146-treated amyloid was significantly higher than control animals (FIG. 17B). At day 14, the TNT 146-treated amyloid exhibited visibly higher fluorescence emission than control animals (FIG. 18). These data indicate that the binding of TNT 146 to amyloid enhances the phagocytosis of human amyloid when injected subcutaneously in mice.

Example 10 Complement-Enhanced Phagocytosis of Amyloid Fibrils

Step 1: Differentiation of THP-1 Cells into MO Macrophages

Count and plate $10^6$ cells/well into the central wells of a 24-well tissue culture plate (Costar 3526) in complete DMEM/F12 (Hyclone, SH 30023.01) supplemented with 10% FBS (Hyclone, SH 30071.03), 1% Pen-Strep (Gibco, 15140-122) and 1% Gentamycin (Gibco, 15710-064).

Add 50 ng/mL PMA (Sigma, P8139) and allow cells to differentiate for 24 h at 37° C. in a 5% CO2 incubator.

After 24 hrs, carefully remove medium containing PMA by manual aspiration.

Replenish the wells with 1 mL of complete DMEM-F12 medium and allow the cells to rest for a minimum of 48 h.

Step 2: Sample Preparation

Rinse the wells once with 1 ml of DPBS (Hyclone, SH 30028.02).

Add 500 µL of serum-free RPMI-1640 without phenol red (Hyclone, SH30605.01) into each well and incubate the plate at 37° C. until the start of the assay.

Prepare the reaction by addition of 500 µl of RPMI-1640 into microfuge tubes followed by addition of TNT 146 or control Fc at 3 µg. Mix well.

To the microfuge tubes, add pHrodo red-labeled (pHrodo™ Red SE, ThermoFisher, P36600) rVλ6Wil fibrils (20 µg).

Next add 20 µg Guinea pig complement to half the wells. Mix well and incubate for 5 min at room temperature.

Transfer the contents of each microfuge tube into their respective wells on the 24-well plate (the total volume in each well will now be 1 mL).

Mix gently by hand, by moving the plate in perpendicular motion (rather than swirling motion).

Incubate the tissue culture plate at 37° C. in a 5% CO2 incubator for 1 h to facilitate phagocytosis.

Step 3: Image Acquisition and Quantification

Following the 1 h incubation, the fluorescence associated with the pHrodo red is recorded by fluorescence microscopy (Keyence BZ X800 V 1.3.1).

Four images are captured for each well to ensure all areas of the well are documented.

The amount of fluorescence in each image is quantified using image segmentation and (Image Pro Premier V 9.0).

The data are analyzed by calculating the mean and standard deviation of the four observations. Statistical analyses were performed using an unpaired, two-tailed t-test with α=0.05 (when the data are normally distributed) using Prism (v. 9.0, GraphPad).

Figure 19:
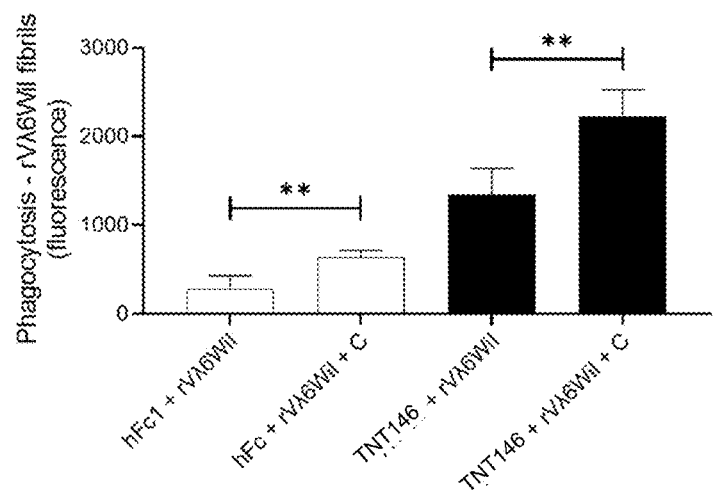
FIG. 19 shows quantitation of phagocytosis of rVλWil AL amyloid fibrils in the presence of guinea pig complement (denoted "C").
Figure 20A:
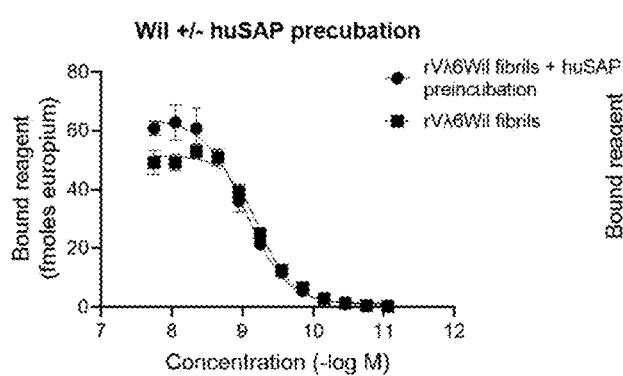
FIG. 20A-FIG. 20D show comparison of binding of a SAP-Fc fusion to amyloid extracts and synthetic fibrils following preincubation with human SAP at a concentration of 30 µg/mL.
Figure 20B:
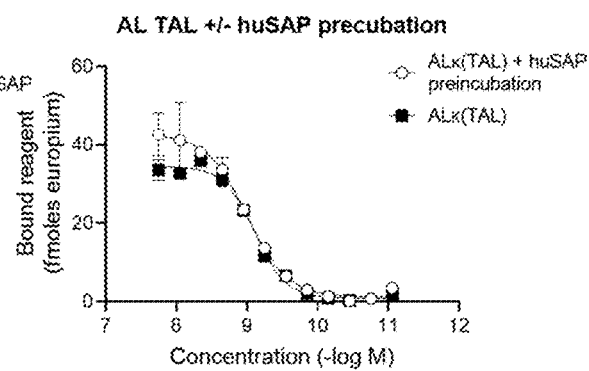
Figure 20C:
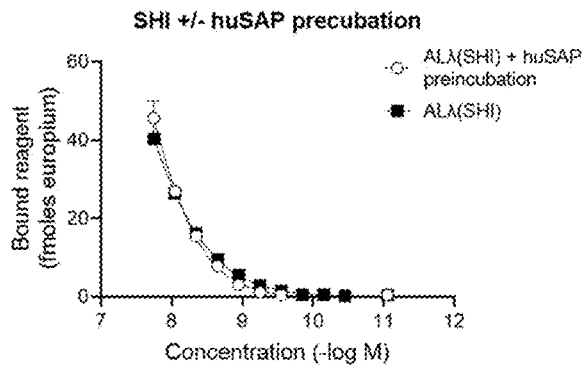
Figure 20D:
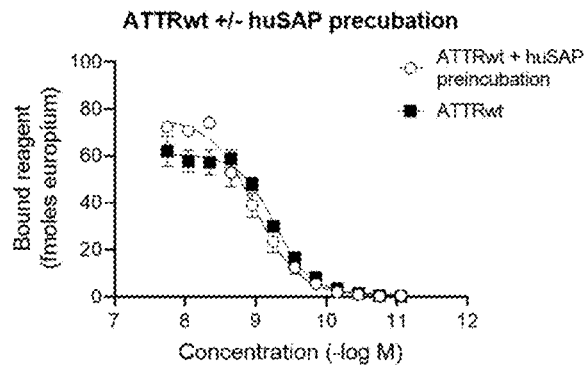

Activated human THP-1 cells effectively take up (phagocytose) synthetic rVλ6Wil AL amyloid-like fibrils when opsonized by the addition of TNT 146. In the presence of 20 µg of highly active guinea pig complement there is a significant increase in the fluorescence intensity of pHrodo red, indicating enhanced phagocytosis of the fibrils in the presence of TNT 146 and complement (FIG. 19).

Example 11 Binding of SAP-Fc Fusion to Amyloid Fibrils in the Presence of huSAP

Human amyloid extracts (ALκ TAL and ALλ SHI), ATTRwt, and synthetic AL amyloid-like fibrils (rVλ6Wil) were pretreated by incubation, in a 96-well microplate, in a solution of human serum amyloid P component (SAP) in TBS with 2 mM $CaCL_2$ for 30 min at 37° C. Stock solutions of rVλ6Wil and amyloid extracts at 0.83 µM and 0.06 mg/mL, respectively were used. Samples not incubated in human SAP served as controls. Following the incubation, the samples were washed TNT 146 (MW=410 kD) added to the microplate wells in a serial dilution from 100 nM in $TBS/CaCL_2$. Following a wash step, the bound TNT 146 was detected by the addition of a biotinylated anti-human Fc reagent. The bound TNT 146 was quantified, by measuring the time-resolved fluorescence, following addition of streptavidin-europium conjugate and developer solution.

The mean and SD of replicate wells was plotted, and the data fit to a sigmoidal algorithm with variable slope (Prism v9.1, Graphpad).

Pre-binding of human SAP to AL or ATTR amyloid extracts or amyloid-like fibrils did not negatively impact the ability of TNT 146 to bind the substrates. (FIG. 20A-20D).

Example 12 Binding of SAP-Fc Fusion to Amyloid Fibrils in the Presence of huSAP

Synthetic Aβ(1-40) amyloid-like fibrils were coated onto the wells of a 96-well microplate, in PBS. The wells were blocked followed by a wash step and TNT 146 (MW=410 kD) added to the microplate wells in a serial dilution in TBS/CaCL2. The bound TNT 146 was detected by the addition of a biotinylated anti-human Fc reagent. The bound TNT 146 was quantified, by measuring the time-resolved fluorescence, following addition of streptavidin-europium conjugate and developer solution. Human Fc was used as a control reagent.

The mean and SD of replicate wells was plotted, and the data fit to a sigmoidal algorithm with variable slope (Prism v9.1, Graphpad).

Figure 21:
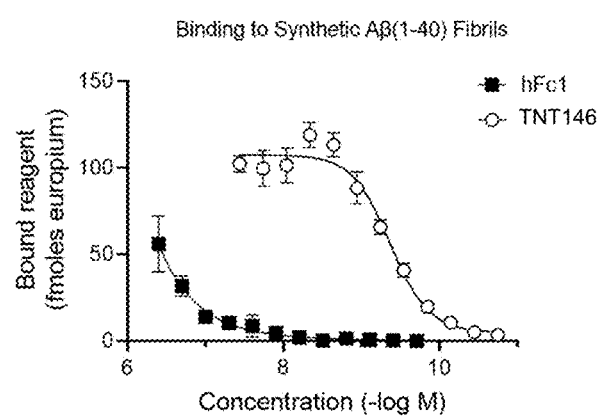
FIG. 21 shows binding of a SAP-Fc fusion to amyloid extracts in the presence of human SAP at a concentration of 30 µg/mL.

The binding of TNT 146 to Aβ(1-40) amyloid-like fibrils resulted in saturable binding with an estimated EC50 (concentration at 50% half maximal binding) of 0.4 nM (FIG. 21). The binding of the Fc was weak and no Ec50 could be accurately determined but was estimated to be ~0.2 mM.

What is claimed is:

1. A fusion protein comprising a structure represented by the following formula, from N-terminus to C-terminus, SAP-Fc1-L1-Fc2, wherein Fc1 is a first Fc domain sequence comprising hinge-CH2-CH3, L1 is a linker, and Fc2 is a second Fc domain sequence comprising hinge-CH2-CH3, wherein SAP is a human serum amyloid P (SAP) component protein, wherein Fc1 and Fc2 each comprise amino acid substitutions C226S and C229S, according to EU numbering, wherein the fusion protein comprises the amino acid sequence set forth in SEQ ID NO: 1 with or without the C-terminal lysine, or SEQ ID NO: 23 with or without the C-terminal lysine.

2. A fusion protein comprising a structure represented by the following formula, from N-terminus to C-terminus, SAP-Fc1-L1-Fc2, wherein Fc1 is a first Fc domain sequence comprising hinge-CH2-CH3, L1 is a linker, and Fc2 is a second Fc domain sequence comprising hinge-CH2-CH3, wherein SAP is a human serum amyloid P (SAP) component protein, wherein Fc1 and Fc2 each comprise amino acid substitutions C226S and C229S, according to EU numbering, wherein the human SAP comprises the amino acid sequence set forth in SEQ ID NO: 20.

3. The fusion protein of claim 2, wherein Fc1 and Fc2 each comprise the amino acid sequence set forth in SEQ ID NO: 18.

4. The fusion protein of claim 2, wherein the Fc1 or Fc2 comprises a mutation that reduces FcRn binding.

5. The fusion protein of claim 1, wherein the fusion protein forms a pentamer or a decamer.

6. The fusion protein of claim 1, wherein the fusion protein has reduced aggregation compared to a fusion protein lacking the amino acid substitutions.

7. A pharmaceutical composition comprising the fusion protein of claim 1, and a pharmaceutically acceptable carrier.

8. The fusion protein of claim 1, wherein the fusion protein is produced by a method comprising culturing a host cell comprising nucleic acid encoding the fusion protein under conditions to express the fusion protein.

9. The fusion protein of claim 2, wherein L1 comprises the amino acid sequence set forth in SEQ ID NO: 19.

10. The fusion protein of claim 3, wherein L1 comprises the amino acid sequence set forth in SEQ ID NO:19.

11. The fusion protein of claim 2, wherein the fusion protein forms a pentamer or a decamer.

12. The fusion protein of claim 2, wherein the Fc1 and Fc2 are human Fc domains.

13. The fusion protein of claim 12, wherein the Fc1 and Fc2 are human IgG1 Fc domains.

14. The fusion protein of claim 2, wherein the fusion protein has reduced aggregation compared to a fusion protein lacking the amino acid substitutions.

15. A pharmaceutical composition comprising the fusion protein of claim 2, and a pharmaceutically acceptable carrier.

16. The fusion protein of claim 2, wherein the fusion protein is produced by a method comprising culturing a host cell comprising nucleic acid encoding the fusion protein under conditions to express the fusion protein.

17. The fusion protein of claim 1, wherein the fusion protein comprises the amino acid sequence set forth in SEQ ID NO: 1 with or without the C-terminal lysine.

18. The fusion protein of claim 1, wherein the fusion protein comprises the amino acid sequence set forth in SEQ ID NO: 23 with or without the C-terminal lysine.

19. The fusion protein of claim 2, wherein the Fc1 and Fc2 each comprise
the amino acid sequence set forth in SEQ ID NO: 21.

* * * * *

SEQUENCE LISTING

```
<160> NUMBER OF SEQ ID NOS: 25

<210> SEQ ID NO 1
<211> LENGTH: 683
<212> TYPE: PRT
<213> ORGANISM: Artificial Sequence
<220> FEATURE:
<223> OTHER INFORMATION: Synthetic Construct

<400> SEQUENCE: 1

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60
```

```
Lys Glu Arg Val Gly Glu Tyr Ser Leu Tyr Ile Gly Arg His Lys Val
 65                  70                  75                  80

Thr Ser Lys Val Ile Glu Lys Phe Pro Ala Pro Val His Ile Cys Val
                 85                  90                  95

Ser Trp Glu Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
            115                 120                 125

Pro Lys Ile Val Leu Gly Gln Glu Gln Asp Ser Tyr Gly Gly Lys Phe
        130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val Glu Pro Lys Ser
            195                 200                 205

Ser Asp Lys Thr His Thr Ser Pro Pro Ser Pro Ala Pro Glu Leu Leu
210                 215                 220

Gly Gly Pro Ser Val Phe Leu Phe Pro Lys Pro Lys Asp Thr Leu
225                 230                 235                 240

Met Ile Ser Arg Thr Pro Glu Val Thr Cys Val Val Asp Val Ser
                245                 250                 255

His Glu Asp Pro Glu Val Lys Phe Asn Trp Tyr Val Asp Gly Val Glu
                260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu His Gln Asp Trp Leu Asn
290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
            340                 345                 350

Ser Leu Thr Cys Leu Val Lys Gly Phe Tyr Pro Ser Asp Ile Ala Val
            355                 360                 365

Glu Trp Glu Ser Asn Gly Gln Pro Glu Asn Asn Tyr Lys Thr Thr Pro
370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn His Tyr Thr Gln Lys Ser Leu Ser Leu
            420                 425                 430

Ser Pro Gly Lys Gly Gly Gly Ser Gly Gly Gly Ser Gly Gly
            435                 440                 445

Gly Gly Ser Glu Pro Lys Ser Ser Asp Lys Thr His Thr Ser Pro Pro
            450                 455                 460

Ser Pro Ala Pro Glu Leu Leu Gly Gly Pro Ser Val Phe Leu Phe Pro
465                 470                 475                 480

Pro Lys Pro Lys Asp Thr Leu Met Ile Ser Arg Thr Pro Glu Val Thr
```

```
                        485                 490                 495
    Cys Val Val Asp Val Ser His Glu Asp Pro Glu Val Lys Phe Asn
                    500                 505                 510

Trp Tyr Val Asp Gly Val Glu Val His Asn Ala Lys Thr Lys Pro Arg
                515                 520                 525

Glu Glu Gln Tyr Asn Ser Thr Tyr Arg Val Val Ser Val Leu Thr Val
            530                 535                 540

Leu His Gln Asp Trp Leu Asn Gly Lys Glu Tyr Lys Cys Lys Val Ser
    545                 550                 555                 560

Asn Lys Ala Leu Pro Ala Pro Ile Glu Lys Thr Ile Ser Lys Ala Lys
                    565                 570                 575

Gly Gln Pro Arg Glu Pro Gln Val Tyr Thr Leu Pro Pro Ser Arg Glu
                580                 585                 590

Glu Met Thr Lys Asn Gln Val Ser Leu Thr Cys Leu Val Lys Gly Phe
            595                 600                 605

Tyr Pro Ser Asp Ile Ala Val Glu Trp Glu Ser Asn Gly Gln Pro Glu
        610                 615                 620

Asn Asn Tyr Lys Thr Thr Pro Pro Val Leu Asp Ser Asp Gly Ser Phe
    625                 630                 635                 640

Phe Leu Tyr Ser Lys Leu Thr Val Asp Lys Ser Arg Trp Gln Gln Gly
                    645                 650                 655

Asn Val Phe Ser Cys Ser Val Met His Glu Ala Leu His Asn His Tyr
                660                 665                 670

Thr Gln Lys Ser Leu Ser Leu Ser Pro Gly Lys
            675                 680

<210> SEQ ID NO 2
<211> LENGTH: 683
<212> TYPE: PRT
<213> ORGANISM: Artificial Sequence
<220> FEATURE:
<223> OTHER INFORMATION: Synthetic Construct

<400> SEQUENCE: 2

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Ser
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65              70                  75                  80

Thr Ser Lys Val Ile Glu Lys Phe Pro Ala Pro Val His Ile Cys Val
                85                  90                  95

Ser Trp Glu Ser Ser Ser Gly Ile Ala Glu Phe Trp Ile Ser Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
```

```
                165                 170                 175
Pro Leu Pro Ala Asn Ile Leu Asp Trp Gln Ala Leu Asn Tyr Glu Ile
            180                 185                 190
Arg Gly Tyr Val Ile Lys Pro Leu Val Trp Val Glu Pro Lys Ser
        195                 200                 205
Ser Asp Lys Thr His Thr Ser Pro Ser Pro Ala Pro Glu Leu Leu
    210                 215                 220
Gly Gly Pro Ser Val Phe Leu Phe Pro Lys Pro Lys Asp Thr Leu
225                 230                 235                 240
Met Ile Ser Arg Thr Pro Glu Val Thr Cys Val Val Asp Val Ser
                245                 250                 255
His Glu Asp Pro Glu Val Lys Phe Asn Trp Tyr Val Asp Gly Val Glu
            260                 265                 270
Val His Asn Ala Lys Thr Lys Pro Arg Glu Glu Gln Tyr Asn Ser Thr
        275                 280                 285
Tyr Arg Val Val Ser Val Leu Thr Val Leu His Gln Asp Trp Leu Asn
    290                 295                 300
Gly Lys Glu Tyr Lys Cys Lys Val Ser Asn Lys Ala Leu Pro Ala Pro
305                 310                 315                 320
Ile Glu Lys Thr Ile Ser Lys Ala Lys Gly Gln Pro Arg Glu Pro Gln
                325                 330                 335
Val Tyr Thr Leu Pro Pro Ser Arg Glu Glu Met Thr Lys Asn Gln Val
            340                 345                 350
Ser Leu Thr Cys Leu Val Lys Gly Phe Tyr Pro Ser Asp Ile Ala Val
        355                 360                 365
Glu Trp Glu Ser Asn Gly Gln Pro Glu Asn Asn Tyr Lys Thr Thr Pro
    370                 375                 380
Pro Val Leu Asp Ser Asp Gly Ser Phe Phe Leu Tyr Ser Lys Leu Thr
385                 390                 395                 400
Val Asp Lys Ser Arg Trp Gln Gln Gly Asn Val Phe Ser Cys Ser Val
                405                 410                 415
Met His Glu Ala Leu His Asn His Tyr Thr Gln Lys Ser Leu Ser Leu
            420                 425                 430
Ser Pro Gly Lys Gly Gly Gly Ser Gly Gly Gly Ser Gly Gly
        435                 440                 445
Gly Gly Ser Glu Pro Lys Ser Ser Asp Lys Thr His Thr Ser Pro Pro
    450                 455                 460
Ser Pro Ala Pro Glu Leu Leu Gly Gly Pro Ser Val Phe Leu Phe Pro
465                 470                 475                 480
Pro Lys Pro Lys Asp Thr Leu Met Ile Ser Arg Thr Pro Glu Val Thr
                485                 490                 495
Cys Val Val Val Asp Val Ser His Glu Asp Pro Glu Val Lys Phe Asn
            500                 505                 510
Trp Tyr Val Asp Gly Val Glu Val His Asn Ala Lys Thr Lys Pro Arg
        515                 520                 525
Glu Glu Gln Tyr Asn Ser Thr Tyr Arg Val Val Ser Val Leu Thr Val
    530                 535                 540
Leu His Gln Asp Trp Leu Asn Gly Lys Glu Tyr Lys Cys Lys Val Ser
545                 550                 555                 560
Asn Lys Ala Leu Pro Ala Pro Ile Glu Lys Thr Ile Ser Lys Ala Lys
                565                 570                 575
Gly Gln Pro Arg Glu Pro Gln Val Tyr Thr Leu Pro Pro Ser Arg Glu
            580                 585                 590
```

```
Glu Met Thr Lys Asn Gln Val Ser Leu Thr Cys Leu Val Lys Gly Phe
            595                 600                 605

Tyr Pro Ser Asp Ile Ala Val Glu Trp Glu Ser Asn Gly Gln Pro Glu
        610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                645                 650                 655

Asn Val Phe Ser Cys Ser Val Met His Glu Ala Leu His Asn His Tyr
            660                 665                 670

Thr Gln Lys Ser Leu Ser Leu Ser Pro Gly Lys
            675                 680
```

<210> SEQ ID NO 3
<211> LENGTH: 683
<212> TYPE: PRT
<213> ORGANISM: Artificial Sequence
<220> FEATURE:
<223> OTHER INFORMATION: Synthetic Construct

<400> SEQUENCE: 3

```
His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val Glu Pro Lys Ser
        195                 200                 205

Ser Asp Lys Thr His Thr Ser Pro Ser Pro Ala Pro Glu Leu Leu
    210                 215                 220

Gly Gly Pro Ser Val Phe Leu Phe Pro Pro Lys Pro Lys Asp Thr Leu
225                 230                 235                 240

Met Ala Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270
```

```
Val His Asn Ala Lys Thr Lys Pro Arg Glu Glu Gln Tyr Asn Ser Thr
    275                 280                 285

Tyr Arg Val Val Ser Val Leu Thr Val Leu Ala Gln Asp Trp Leu Asn
    290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
                340                 345                 350

Ser Leu Thr Cys Leu Val Lys Gly Phe Tyr Pro Ser Asp Ile Ala Val
            355                 360                 365

Glu Trp Glu Ser Asn Gly Gln Pro Glu Asn Asn Tyr Lys Thr Thr Pro
        370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn Ala Tyr Thr Gln Lys Ser Leu Ser Leu
                420                 425                 430

Ser Pro Gly Lys Gly Gly Gly Ser Gly Gly Gly Ser Gly Gly
            435                 440                 445

Gly Gly Ser Glu Pro Lys Ser Ser Asp Lys Thr His Thr Ser Pro Pro
        450                 455                 460

Ser Pro Ala Pro Glu Leu Leu Gly Gly Pro Ser Val Phe Leu Phe Pro
465                 470                 475                 480

Pro Lys Pro Lys Asp Thr Leu Met Ala Ser Arg Thr Pro Glu Val Thr
                485                 490                 495

Cys Val Val Val Asp Val Ser His Glu Asp Pro Glu Val Lys Phe Asn
                500                 505                 510

Trp Tyr Val Asp Gly Val Glu Val His Asn Ala Lys Thr Lys Pro Arg
            515                 520                 525

Glu Glu Gln Tyr Asn Ser Thr Tyr Arg Val Val Ser Val Leu Thr Val
        530                 535                 540

Leu Ala Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Ser Arg Glu
                580                 585                 590

Glu Met Thr Lys Asn Gln Val Ser Leu Thr Cys Leu Val Lys Gly Phe
            595                 600                 605

Tyr Pro Ser Asp Ile Ala Val Glu Trp Glu Ser Asn Gly Gln Pro Glu
        610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                645                 650                 655

Asn Val Phe Ser Cys Ser Val Met His Glu Ala Leu His Asn Ala Tyr
                660                 665                 670

Thr Gln Lys Ser Leu Ser Leu Ser Pro Gly Lys
            675                 680
```

```
<210> SEQ ID NO 4
<211> LENGTH: 683
<212> TYPE: PRT
<213> ORGANISM: Artificial Sequence
<220> FEATURE:
<223> OTHER INFORMATION: Synthetic Construct

<400> SEQUENCE: 4

His Thr Asp Leu Ser Gly Lys Val Phe Val Phe Pro Arg Glu Ser Val
  1               5                  10                  15

Thr Asp His Val Asn Leu Ile Thr Pro Leu Glu Lys Pro Leu Gln Ser
             20                  25                  30

Phe Thr Leu Cys Phe Arg Ala Tyr Ser Asp Leu Ser Arg Ala Tyr Ser
         35                  40                  45

Leu Phe Ser Tyr Asn Thr Gln Gly Arg Asp Asn Glu Leu Leu Val Tyr
     50                  55                  60

Lys Glu Arg Val Gly Glu Tyr Ser Leu Tyr Ile Gly Arg His Lys Val
 65                  70                  75                  80

Thr Ser Lys Val Ile Glu Lys Phe Pro Ala Pro Val His Ile Cys Val
                 85                  90                  95

Ser Trp Glu Ser Ser Gly Ile Ala Glu Phe Trp Ile Ser Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val Glu Pro Lys Ser
        195                 200                 205

Ser Asp Lys Thr His Thr Ser Pro Pro Ser Pro Ala Pro Glu Leu Leu
    210                 215                 220

Gly Gly Pro Ser Val Phe Leu Phe Pro Pro Lys Pro Lys Asp Thr Leu
225                 230                 235                 240

Met Ala Ser Arg Thr Pro Glu Val Thr Cys Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu Ala Gln Asp Trp Leu Asn
    290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
            340                 345                 350

Ser Leu Thr Cys Leu Val Lys Gly Phe Tyr Pro Ser Asp Ile Ala Val
        355                 360                 365
```

```
Glu Trp Glu Ser Asn Gly Gln Pro Glu Asn Asn Tyr Lys Thr Thr Pro
    370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn Ala Tyr Thr Gln Lys Ser Leu Ser Leu
            420                 425                 430

Ser Pro Gly Lys Gly Gly Gly Ser Gly Gly Gly Ser Gly Gly
        435                 440                 445

Gly Gly Ser Glu Pro Lys Ser Ser Asp Lys Thr His Thr Ser Pro Pro
450                 455                 460

Ser Pro Ala Pro Glu Leu Leu Gly Gly Pro Ser Val Phe Leu Phe Pro
465                 470                 475                 480

Pro Lys Pro Lys Asp Thr Leu Met Ala Ser Arg Thr Pro Glu Val Thr
                485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Asn Ser Thr Tyr Arg Val Val Ser Val Leu Thr Val
530                 535                 540

Leu Ala Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Ser Arg Glu
            580                 585                 590

Glu Met Thr Lys Asn Gln Val Ser Leu Thr Cys Leu Val Lys Gly Phe
        595                 600                 605

Tyr Pro Ser Asp Ile Ala Val Glu Trp Glu Ser Asn Gly Gln Pro Glu
610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                645                 650                 655

Asn Val Phe Ser Cys Ser Val Met His Glu Ala Leu His Asn Ala Tyr
            660                 665                 670

Thr Gln Lys Ser Leu Ser Leu Ser Pro Gly Lys
        675                 680

<210> SEQ ID NO 5
<211> LENGTH: 436
<212> TYPE: PRT
<213> ORGANISM: Artificial Sequence
<220> FEATURE:
<223> OTHER INFORMATION: Synthetic Construct

<400> SEQUENCE: 5

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45
```

```
Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
 65                  70                  75                  80

Thr Ser Lys Val Ile Glu Lys Phe Pro Ala Pro Val His Ile Cys Val
                    85                  90                  95

Ser Trp Glu Ser Ser Ser Gly Ile Ala Glu Phe Trp Ile Asn Gly Thr
                100                 105                 110

Pro Leu Val Lys Lys Gly Leu Arg Gln Gly Tyr Phe Val Glu Ala Gln
                115                 120                 125

Pro Lys Ile Val Leu Gly Gln Glu Gln Asp Ser Tyr Gly Gly Lys Phe
            130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
                180                 185                 190

Arg Gly Tyr Val Ile Ile Lys Pro Leu Val Trp Val Glu Pro Lys Ser
            195                 200                 205

Ser Asp Lys Thr His Thr Cys Pro Pro Cys Pro Ala Pro Glu Leu Leu
210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
                260                 265                 270

Val His Asn Ala Lys Thr Lys Pro Arg Glu Glu Gln Tyr Asn Ser Thr
            275                 280                 285

Tyr Arg Val Val Ser Val Leu Thr Val Leu His Gln Asp Trp Leu Asn
290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
                340                 345                 350

Ser Leu Trp Cys Leu Val Lys Gly Phe Tyr Pro Ser Asp Ile Ala Val
            355                 360                 365

Glu Trp Glu Ser Asn Gly Gln Pro Glu Asn Asn Tyr Lys Thr Thr Pro
370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn His Tyr Thr Gln Lys Ser Leu Ser Leu
                420                 425                 430

Ser Pro Gly Lys
            435

<210> SEQ ID NO 6
<211> LENGTH: 232
<212> TYPE: PRT
```

<213> ORGANISM: Artificial Sequence
<220> FEATURE:
<223> OTHER INFORMATION: Synthetic Construct

<400> SEQUENCE: 6

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 7
<211> LENGTH: 436
<212> TYPE: PRT
<213> ORGANISM: Artificial Sequence
<220> FEATURE:
<223> OTHER INFORMATION: Synthetic Construct

<400> SEQUENCE: 7

```
His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Ser
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95
```

Ser Trp Glu Ser Ser Gly Ile Ala Glu Phe Trp Ile Ser Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val Glu Pro Lys Ser
        195                 200                 205

Ser Asp Lys Thr His Thr Cys Pro Pro Cys Pro Ala Pro Glu Leu Leu
    210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu His Gln Asp Trp Leu Asn
    290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
            340                 345                 350

Ser Leu Trp Cys Leu Val Lys Gly Phe Tyr Pro Ser Asp Ile Ala Val
        355                 360                 365

Glu Trp Glu Ser Asn Gly Gln Pro Glu Asn Asn Tyr Lys Thr Thr Pro
    370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn His Tyr Thr Gln Lys Ser Leu Ser Leu
            420                 425                 430

Ser Pro Gly Lys
        435

<210> SEQ ID NO 8
<211> LENGTH: 436
<212> TYPE: PRT
<213> ORGANISM: Artificial Sequence
<220> FEATURE:
<223> OTHER INFORMATION: Synthetic Construct

<400> SEQUENCE: 8

His Thr Asp Leu Ser Gly Lys Val Phe Val Phe Pro Arg Glu Ser Val
1               5                   10                  15

```
Thr Asp His Val Asn Leu Ile Thr Pro Leu Glu Lys Pro Leu Gln Asn
             20                  25                  30
Phe Thr Leu Cys Phe Arg Ala Tyr Ser Asp Leu Ser Arg Ala Tyr Ser
         35                  40                  45
Leu Phe Ser Tyr Asn Thr Gln Gly Arg Asp Asn Glu Leu Leu Val Tyr
     50                  55                  60
Lys Glu Arg Val Gly Glu Tyr Ser Leu Tyr Ile Gly Arg His Lys Val
 65                  70                  75                  80
Thr Ser Lys Val Ile Glu Lys Phe Pro Ala Pro Val His Ile Cys Val
                 85                  90                  95
Ser Trp Glu Ser Ser Gly Ile Ala Glu Phe Trp Ile Asn Gly Thr
             100                 105                 110
Pro Leu Val Lys Lys Gly Leu Arg Gln Gly Tyr Phe Val Glu Ala Gln
             115                 120                 125
Pro Lys Ile Val Leu Gly Gln Glu Gln Asp Ser Tyr Gly Gly Lys Phe
         130                 135                 140
Asp Arg Ser Gln Ser Phe Val Gly Glu Ile Gly Asp Leu Tyr Met Trp
145                 150                 155                 160
Asp Ser Val Leu Pro Pro Glu Asn Ile Leu Ser Ala Tyr Gln Gly Thr
                 165                 170                 175
Pro Leu Pro Ala Asn Ile Leu Asp Trp Gln Ala Leu Asn Tyr Glu Ile
             180                 185                 190
Arg Gly Tyr Val Ile Ile Lys Pro Leu Val Trp Val Glu Pro Lys Ser
             195                 200                 205
Ser Asp Lys Thr His Thr Cys Pro Pro Cys Pro Ala Pro Glu Leu Leu
210                 215                 220
Gly Gly Pro Ser Val Phe Leu Phe Pro Pro Lys Pro Lys Asp Thr Leu
225                 230                 235                 240
Met Ala Ser Arg Thr Pro Glu Val Thr Cys Val Val Asp Val Ser
                 245                 250                 255
His Glu Asp Pro Glu Val Lys Phe Asn Trp Tyr Val Asp Gly Val Glu
             260                 265                 270
Val His Asn Ala Lys Thr Lys Pro Arg Glu Glu Gln Tyr Asn Ser Thr
             275                 280                 285
Tyr Arg Val Val Ser Val Leu Thr Val Leu Ala Gln Asp Trp Leu Asn
         290                 295                 300
Gly Lys Glu Tyr Lys Cys Lys Val Ser Asn Lys Ala Leu Pro Ala Pro
305                 310                 315                 320
Ile Glu Lys Thr Ile Ser Lys Ala Lys Gly Gln Pro Arg Glu Pro Gln
                 325                 330                 335
Val Tyr Thr Leu Pro Pro Ser Arg Glu Glu Met Thr Lys Asn Gln Val
             340                 345                 350
Ser Leu Trp Cys Leu Val Lys Gly Phe Tyr Pro Ser Asp Ile Ala Val
         355                 360                 365
Glu Trp Glu Ser Asn Gly Gln Pro Glu Asn Asn Tyr Lys Thr Thr Pro
     370                 375                 380
Pro Val Leu Asp Ser Asp Gly Ser Phe Phe Leu Tyr Ser Lys Leu Thr
385                 390                 395                 400
Val Asp Lys Ser Arg Trp Gln Gln Gly Asn Val Phe Ser Cys Ser Val
                 405                 410                 415
Met His Glu Ala Leu His Asn Ala Tyr Thr Gln Lys Ser Leu Ser Leu
             420                 425                 430
Ser Pro Gly Lys
```

435

<210> SEQ ID NO 9
<211> LENGTH: 232
<212> TYPE: PRT
<213> ORGANISM: Artificial Sequence
<220> FEATURE:
<223> OTHER INFORMATION: Synthetic Construct

<400> SEQUENCE: 9

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ala Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu Ala Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Ala Tyr Thr Gln Lys
210                 215                 220

Ser Leu Ser Leu Ser Pro Gly Lys
225                 230

<210> SEQ ID NO 10
<211> LENGTH: 436
<212> TYPE: PRT
<213> ORGANISM: Artificial Sequence
<220> FEATURE:
<223> OTHER INFORMATION: Synthetic Construct

<400> SEQUENCE: 10

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Ser
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

-continued

Lys Glu Arg Val Gly Glu Tyr Ser Leu Tyr Ile Gly Arg His Lys Val
 65                  70                  75                  80

Thr Ser Lys Val Ile Glu Lys Phe Pro Ala Pro Val His Ile Cys Val
                 85                  90                  95

Ser Trp Glu Ser Ser Ser Gly Ile Ala Glu Phe Trp Ile Ser Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val Glu Pro Lys Ser
        195                 200                 205

Ser Asp Lys Thr His Thr Cys Pro Pro Cys Pro Ala Pro Glu Leu Leu
210                 215                 220

Gly Gly Pro Ser Val Phe Leu Phe Pro Pro Lys Pro Lys Asp Thr Leu
225                 230                 235                 240

Met Ala Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu Ala Gln Asp Trp Leu Asn
290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
            340                 345                 350

Ser Leu Trp Cys Leu Val Lys Gly Phe Tyr Pro Ser Asp Ile Ala Val
        355                 360                 365

Glu Trp Glu Ser Asn Gly Gln Pro Glu Asn Asn Tyr Lys Thr Thr Pro
370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn Ala Tyr Thr Gln Lys Ser Leu Ser Leu
            420                 425                 430

Ser Pro Gly Lys
        435

<210> SEQ ID NO 11
<211> LENGTH: 436
<212> TYPE: PRT
<213> ORGANISM: Artificial Sequence
<220> FEATURE:
<223> OTHER INFORMATION: Synthetic Construct

<400> SEQUENCE: 11

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
            35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
            115                 120                 125

Pro Lys Ile Val Leu Gly Gln Glu Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val Glu Pro Lys Ser
            195                 200                 205

Ser Asp Lys Thr His Thr Cys Pro Pro Cys Pro Ala Pro Glu Leu Leu
    210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
            275                 280                 285

Tyr Arg Val Val Ser Val Leu Thr Val Leu His Gln Asp Trp Leu Asn
    290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
            340                 345                 350

Ser Leu Ser Cys Ala Val Lys Gly Phe Tyr Pro Ser Asp Ile Ala Val
            355                 360                 365

Glu Trp Glu Ser Asn Gly Gln Pro Glu Asn Asn Tyr Lys Thr Thr Pro
    370                 375                 380

Pro Val Leu Asp Ser Asp Gly Ser Phe Phe Leu Val Ser Lys Leu Thr
385                 390                 395                 400

Val Asp Lys Ser Arg Trp Gln Gln Gly Asn Val Phe Ser Cys Ser Val

```
                        405                 410                 415
Met His Glu Ala Leu His Asn His Tyr Thr Gln Lys Ser Leu Ser Leu
                420                 425                 430

Ser Pro Gly Lys
        435

<210> SEQ ID NO 12
<211> LENGTH: 232
<212> TYPE: PRT
<213> ORGANISM: Artificial Sequence
<220> FEATURE:
<223> OTHER INFORMATION: Synthetic Construct

<400> SEQUENCE: 12

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 13
<211> LENGTH: 436
<212> TYPE: PRT
<213> ORGANISM: Artificial Sequence
<220> FEATURE:
<223> OTHER INFORMATION: Synthetic Construct

<400> SEQUENCE: 13

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Ser
            20                  25                  30
```

```
Phe Thr Leu Cys Phe Arg Ala Tyr Ser Asp Leu Ser Arg Ala Tyr Ser
            35                  40                  45
Leu Phe Ser Tyr Asn Thr Gln Gly Arg Asp Asn Glu Leu Leu Val Tyr
 50                  55                  60
Lys Glu Arg Val Gly Glu Tyr Ser Leu Tyr Ile Gly Arg His Lys Val
 65                  70                  75                  80
Thr Ser Lys Val Ile Glu Lys Phe Pro Ala Pro Val His Ile Cys Val
                 85                  90                  95
Ser Trp Glu Ser Ser Gly Ile Ala Glu Phe Trp Ile Ser Gly Thr
                100                 105                 110
Pro Leu Val Lys Lys Gly Leu Arg Gln Gly Tyr Phe Val Glu Ala Gln
            115                 120                 125
Pro Lys Ile Val Leu Gly Gln Glu Gln Asp Ser Tyr Gly Gly Lys Phe
130                 135                 140
Asp Arg Ser Gln Ser Phe Val Gly Glu Ile Gly Asp Leu Tyr Met Trp
145                 150                 155                 160
Asp Ser Val Leu Pro Pro Glu Asn Ile Leu Ser Ala Tyr Gln Gly Thr
                165                 170                 175
Pro Leu Pro Ala Asn Ile Leu Asp Trp Gln Ala Leu Asn Tyr Glu Ile
            180                 185                 190
Arg Gly Tyr Val Ile Ile Lys Pro Leu Val Trp Val Glu Pro Lys Ser
            195                 200                 205
Ser Asp Lys Thr His Thr Cys Pro Pro Cys Pro Ala Pro Glu Leu Leu
210                 215                 220
Gly Gly Pro Ser Val Phe Leu Phe Pro Pro Lys Pro Lys Asp Thr Leu
225                 230                 235                 240
Met Ile Ser Arg Thr Pro Glu Val Thr Cys Val Val Val Asp Val Ser
                245                 250                 255
His Glu Asp Pro Glu Val Lys Phe Asn Trp Tyr Val Asp Gly Val Glu
                260                 265                 270
Val His Asn Ala Lys Thr Lys Pro Arg Glu Glu Gln Tyr Asn Ser Thr
            275                 280                 285
Tyr Arg Val Val Ser Val Leu Thr Val Leu His Gln Asp Trp Leu Asn
290                 295                 300
Gly Lys Glu Tyr Lys Cys Lys Val Ser Asn Lys Ala Leu Pro Ala Pro
305                 310                 315                 320
Ile Glu Lys Thr Ile Ser Lys Ala Lys Gly Gln Pro Arg Glu Pro Gln
                325                 330                 335
Val Tyr Thr Leu Pro Pro Ser Arg Glu Glu Met Thr Lys Asn Gln Val
            340                 345                 350
Ser Leu Ser Cys Ala Val Lys Gly Phe Tyr Pro Ser Asp Ile Ala Val
            355                 360                 365
Glu Trp Glu Ser Asn Gly Gln Pro Glu Asn Asn Tyr Lys Thr Thr Pro
370                 375                 380
Pro Val Leu Asp Ser Asp Gly Ser Phe Phe Leu Val Ser Lys Leu Thr
385                 390                 395                 400
Val Asp Lys Ser Arg Trp Gln Gln Gly Asn Val Phe Ser Cys Ser Val
                405                 410                 415
Met His Glu Ala Leu His Asn His Tyr Thr Gln Lys Ser Leu Ser Leu
            420                 425                 430
Ser Pro Gly Lys
            435
```

```
<210> SEQ ID NO 14
<211> LENGTH: 436
<212> TYPE: PRT
<213> ORGANISM: Artificial Sequence
<220> FEATURE:
<223> OTHER INFORMATION: Synthetic Construct

<400> SEQUENCE: 14

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val Glu Pro Lys Ser
        195                 200                 205

Ser Asp Lys Thr His Thr Cys Pro Pro Cys Pro Ala Pro Glu Leu Leu
    210                 215                 220

Gly Gly Pro Ser Val Phe Leu Phe Pro Pro Lys Pro Lys Asp Thr Leu
225                 230                 235                 240

Met Ala Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu Ala Gln Asp Trp Leu Asn
    290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
            340                 345                 350

Ser Leu Ser Cys Ala Val Lys Gly Phe Tyr Pro Ser Asp Ile Ala Val
        355                 360                 365

Glu Trp Glu Ser Asn Gly Gln Pro Glu Asn Asn Tyr Lys Thr Thr Pro
```

```
                    370                 375                 380
Pro Val Leu Asp Ser Asp Gly Ser Phe Phe Leu Val Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn Ala Tyr Thr Gln Lys Ser Leu Ser Leu
                420                 425                 430

Ser Pro Gly Lys
            435

<210> SEQ ID NO 15
<211> LENGTH: 232
<212> TYPE: PRT
<213> ORGANISM: Artificial Sequence
<220> FEATURE:
<223> OTHER INFORMATION: Synthetic Construct

<400> SEQUENCE: 15

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ala Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu Ala Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Ala Tyr Thr Gln Lys
    210                 215                 220

Ser Leu Ser Leu Ser Pro Gly Lys
225                 230

<210> SEQ ID NO 16
<211> LENGTH: 436
<212> TYPE: PRT
<213> ORGANISM: Artificial Sequence
<220> FEATURE:
<223> OTHER INFORMATION: Synthetic Construct

<400> SEQUENCE: 16
```

-continued

```
His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Ser
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Ser Gly Ile Ala Glu Phe Trp Ile Ser Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val Glu Pro Lys Ser
        195                 200                 205

Ser Asp Lys Thr His Thr Cys Pro Pro Cys Pro Ala Pro Glu Leu Leu
    210                 215                 220

Gly Gly Pro Ser Val Phe Leu Phe Pro Pro Lys Pro Lys Asp Thr Leu
225                 230                 235                 240

Met Ala Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu Ala Gln Asp Trp Leu Asn
    290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
            340                 345                 350

Ser Leu Ser Cys Ala Val Lys Gly Phe Tyr Pro Ser Asp Ile Ala Val
        355                 360                 365

Glu Trp Glu Ser Asn Gly Gln Pro Glu Asn Asn Tyr Lys Thr Thr Pro
    370                 375                 380

Pro Val Leu Asp Ser Asp Gly Ser Phe Phe Leu Val Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn Ala Tyr Thr Gln Lys Ser Leu Ser Leu
```

Ser Pro Gly Lys
            435

<210> SEQ ID NO 17
<211> LENGTH: 204
<212> TYPE: PRT
<213> ORGANISM: Artificial Sequence
<220> FEATURE:
<223> OTHER INFORMATION: Synthetic Construct

<400> SEQUENCE: 17

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val
        195                 200

<210> SEQ ID NO 18
<211> LENGTH: 232
<212> TYPE: PRT
<213> ORGANISM: Artificial Sequence
<220> FEATURE:
<223> OTHER INFORMATION: Synthetic Construct

<400> SEQUENCE: 18

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
        100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 19
<211> LENGTH: 15
<212> TYPE: PRT
<213> ORGANISM: Artificial Sequence
<220> FEATURE:
<223> OTHER INFORMATION: Synthetic Construct

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 204
<212> TYPE: PRT
<213> ORGANISM: Artificial Sequence
<220> FEATURE:
<223> OTHER INFORMATION: Synthetic Construct

<400> SEQUENCE: 20

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Ser
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Ser Gly Ile Ala Glu Phe Trp Ile Ser Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

```
Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
            165                 170                 175

Pro Leu Pro Ala Asn Ile Leu Asp Trp Gln Ala Leu Asn Tyr Glu Ile
        180                 185                 190

Arg Gly Tyr Val Ile Ile Lys Pro Leu Val Trp Val
        195                 200
```

<210> SEQ ID NO 21
<211> LENGTH: 232
<212> TYPE: PRT
<213> ORGANISM: Artificial Sequence
<220> FEATURE:
<223> OTHER INFORMATION: Synthetic Construct

<400> SEQUENCE: 21

```
Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ala Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu Ala Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Ala Tyr Thr Gln Lys
210                 215                 220

Ser Leu Ser Leu Ser Pro Gly Lys
225                 230
```

<210> SEQ ID NO 22
<211> LENGTH: 683
<212> TYPE: PRT
<213> ORGANISM: Artificial Sequence
<220> FEATURE:
<223> OTHER INFORMATION: Synthetic Construct

<400> SEQUENCE: 22

```
His Thr Asp Leu Ser Gly Lys Val Phe Val Phe Pro Arg Glu Ser Val
```

-continued

```
1               5                   10                  15
Thr Asp His Val Asn Leu Ile Thr Pro Leu Glu Lys Pro Leu Gln Asn
                20                  25                  30
Phe Thr Leu Cys Phe Arg Ala Tyr Ser Asp Leu Ser Arg Ala Tyr Ser
                35                  40                  45
Leu Phe Ser Tyr Asn Thr Gln Gly Arg Asp Asn Glu Leu Leu Val Tyr
    50                  55                  60
Lys Glu Arg Val Gly Glu Tyr Ser Leu Tyr Ile Gly Arg His Lys Val
65                  70                  75                  80
Thr Ser Lys Val Ile Glu Lys Phe Pro Ala Pro Val His Ile Cys Val
                85                  90                  95
Ser Trp Glu Ser Ser Gly Ile Ala Glu Phe Trp Ile Asn Gly Thr
                100                 105                 110
Pro Leu Val Lys Lys Gly Leu Arg Gln Gly Tyr Phe Val Glu Ala Gln
                115                 120                 125
Pro Lys Ile Val Leu Gly Gln Glu Gln Asp Ser Tyr Gly Gly Lys Phe
            130                 135                 140
Asp Arg Ser Gln Ser Phe Val Gly Glu Ile Gly Asp Leu Tyr Met Trp
145                 150                 155                 160
Asp Ser Val Leu Pro Pro Glu Asn Ile Leu Ser Ala Tyr Gln Gly Thr
                165                 170                 175
Pro Leu Pro Ala Asn Ile Leu Asp Trp Gln Ala Leu Asn Tyr Glu Ile
                180                 185                 190
Arg Gly Tyr Val Ile Ile Lys Pro Leu Val Trp Val Glu Pro Lys Ser
                195                 200                 205
Ser Asp Lys Thr His Thr Cys Pro Pro Cys Pro Ala Pro Glu Leu Leu
    210                 215                 220
Gly Gly Pro Ser Val Phe Leu Phe Pro Pro Lys Pro Lys Asp Thr Leu
225                 230                 235                 240
Met Ile Ser Arg Thr Pro Glu Val Thr Cys Val Val Val Asp Val Ser
                245                 250                 255
His Glu Asp Pro Glu Val Lys Phe Asn Trp Tyr Val Asp Gly Val Glu
                260                 265                 270
Val His Asn Ala Lys Thr Lys Pro Arg Glu Glu Gln Tyr Asn Ser Thr
                275                 280                 285
Tyr Arg Val Val Ser Val Leu Thr Val Leu His Gln Asp Trp Leu Asn
        290                 295                 300
Gly Lys Glu Tyr Lys Cys Lys Val Ser Asn Lys Ala Leu Pro Ala Pro
305                 310                 315                 320
Ile Glu Lys Thr Ile Ser Lys Ala Lys Gly Gln Pro Arg Glu Pro Gln
                325                 330                 335
Val Tyr Thr Leu Pro Pro Ser Arg Glu Glu Met Thr Lys Asn Gln Val
                340                 345                 350
Ser Leu Thr Cys Leu Val Lys Gly Phe Tyr Pro Ser Asp Ile Ala Val
                355                 360                 365
Glu Trp Glu Ser Asn Gly Gln Pro Glu Asn Asn Tyr Lys Thr Thr Pro
        370                 375                 380
Pro Val Leu Asp Ser Asp Gly Ser Phe Phe Leu Tyr Ser Lys Leu Thr
385                 390                 395                 400
Val Asp Lys Ser Arg Trp Gln Gln Gly Asn Val Phe Ser Cys Ser Val
                405                 410                 415
Met His Glu Ala Leu His Asn His Tyr Thr Gln Lys Ser Leu Ser Leu
                420                 425                 430
```

Ser Pro Gly Lys Gly Gly Gly Ser Gly Gly Gly Ser Gly Gly
            435                 440                 445

Gly Gly Ser Glu Pro Lys Ser Ser Asp Lys Thr His Thr Cys Pro Pro
        450                 455                 460

Cys Pro Ala Pro Glu Leu Leu Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Asn Ser Thr Tyr Arg Val Val Ser Val Leu Thr Val
    530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Ser Arg Glu
            580                 585                 590

Glu Met Thr Lys Asn Gln Val Ser Leu Thr Cys Leu Val Lys Gly Phe
        595                 600                 605

Tyr Pro Ser Asp Ile Ala Val Glu Trp Glu Ser Asn Gly Gln Pro Glu
    610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                645                 650                 655

Asn Val Phe Ser Cys Ser Val Met His Glu Ala Leu His Asn His Tyr
            660                 665                 670

Thr Gln Lys Ser Leu Ser Leu Ser Pro Gly Lys
        675                 680

<210> SEQ ID NO 23
<211> LENGTH: 683
<212> TYPE: PRT
<213> ORGANISM: Artificial Sequence
<220> FEATURE:
<223> OTHER INFORMATION: Synthetic Construct

<400> SEQUENCE: 23

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Ser Gly Ile Ala Glu Phe Trp Ile Asn Gly Thr
            100                 105                 110

-continued

```
Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
                180                 185                 190

Arg Gly Tyr Val Ile Ile Lys Pro Leu Val Trp Val Glu Pro Lys Ser
            195                 200                 205

Ser Asp Lys Thr His Thr Ser Pro Pro Ser Pro Ala Pro Glu Leu Leu
        210                 215                 220

Gly Gly Pro Ser Val Phe Leu Phe Pro Pro Lys Pro Lys Asp Thr Leu
225                 230                 235                 240

Met Ala Ser Arg Thr Pro Glu Val Thr Cys Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu Ala Gln Asp Trp Leu Asn
    290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
                340                 345                 350

Ser Leu Thr Cys Leu Val Lys Gly Phe Tyr Pro Ser Asp Ile Ala Val
            355                 360                 365

Glu Trp Glu Ser Asn Gly Gln Pro Glu Asn Asn Tyr Lys Thr Thr Pro
    370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn Ala Tyr Thr Gln Lys Ser Leu Ser Leu
                420                 425                 430

Ser Pro Gly Lys Gly Gly Gly Ser Gly Gly Gly Ser Gly Gly
            435                 440                 445

Gly Gly Ser Glu Pro Lys Ser Ser Asp Lys Thr His Thr Ser Pro Pro
    450                 455                 460

Ser Pro Ala Pro Glu Leu Leu Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525
```

-continued

```
Glu Glu Gln Tyr Asn Ser Thr Tyr Arg Val Val Ser Val Leu Thr Val
530                 535                 540
Leu His Gln Asp Trp Leu Asn Gly Lys Glu Tyr Lys Cys Lys Val Ser
545                 550                 555                 560
Asn Lys Ala Leu Pro Ala Pro Ile Glu Lys Thr Ile Ser Lys Ala Lys
                565                 570                 575
Gly Gln Pro Arg Glu Pro Gln Val Tyr Thr Leu Pro Pro Ser Arg Glu
                580                 585                 590
Glu Met Thr Lys Asn Gln Val Ser Leu Thr Cys Leu Val Lys Gly Phe
                595                 600                 605
Tyr Pro Ser Asp Ile Ala Val Glu Trp Glu Ser Asn Gly Gln Pro Glu
610                 615                 620
Asn Asn Tyr Lys Thr Thr Pro Pro Val Leu Asp Ser Asp Gly Ser Phe
625                 630                 635                 640
Phe Leu Tyr Ser Lys Leu Thr Val Asp Lys Ser Arg Trp Gln Gln Gly
                645                 650                 655
Asn Val Phe Ser Cys Ser Val Met His Glu Ala Leu His Asn His Tyr
                660                 665                 670
Thr Gln Lys Ser Leu Ser Leu Ser Pro Gly Lys
                675                 680

<210> SEQ ID NO 24
<211> LENGTH: 683
<212> TYPE: PRT
<213> ORGANISM: homo sapiens

<400> SEQUENCE: 24

His Thr Asp Leu Ser Gly Lys Val Phe Val Phe Pro Arg Glu Ser Val
1               5                   10                  15
Thr Asp His Val Asn Leu Ile Thr Pro Leu Glu Lys Pro Leu Gln Asn
                20                  25                  30
Phe Thr Leu Cys Phe Arg Ala Tyr Ser Asp Leu Ser Arg Ala Tyr Ser
                35                  40                  45
Leu Phe Ser Tyr Asn Thr Gln Gly Arg Asp Asn Glu Leu Leu Val Tyr
50                  55                  60
Lys Glu Arg Val Gly Glu Tyr Ser Leu Tyr Ile Gly Arg His Lys Val
65                  70                  75                  80
Thr Ser Lys Val Ile Glu Lys Phe Pro Ala Pro Val His Ile Cys Val
                85                  90                  95
Ser Trp Glu Ser Ser Ser Gly Ile Ala Glu Phe Trp Ile Asn Gly Thr
                100                 105                 110
Pro Leu Val Lys Lys Gly Leu Arg Gln Gly Tyr Phe Val Glu Ala Gln
                115                 120                 125
Pro Lys Ile Val Leu Gly Gln Glu Gln Asp Ser Tyr Gly Gly Lys Phe
                130                 135                 140
Asp Arg Ser Gln Ser Phe Val Gly Glu Ile Gly Asp Leu Tyr Met Trp
145                 150                 155                 160
Asp Ser Val Leu Pro Pro Glu Asn Ile Leu Ser Ala Tyr Gln Gly Thr
                165                 170                 175
Pro Leu Pro Ala Asn Ile Leu Asp Trp Gln Ala Leu Asn Tyr Glu Ile
                180                 185                 190
Arg Gly Tyr Val Ile Ile Lys Pro Leu Val Trp Val Glu Pro Lys Ser
                195                 200                 205
Ser Asp Lys Thr His Thr Ser Pro Pro Ser Pro Ala Pro Glu Leu Leu
210                 215                 220
```

```
Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu His Gln Asp Trp Leu Asn
290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Glu Glu Met Thr Lys Asn Gln Val
            340                 345                 350

Ser Leu Thr Cys Leu Val Lys Gly Phe Tyr Pro Ser Asp Ile Ala Val
        355                 360                 365

Glu Trp Glu Ser Asn Gly Gln Pro Glu Asn Asn Tyr Lys Thr Thr Pro
370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn His Tyr Thr Gln Lys Ser Leu Ser Leu
            420                 425                 430

Ser Pro Gly Lys Gly Gly Gly Ser Gly Gly Gly Ser Gly Gly
        435                 440                 445

Gly Gly Ser Glu Pro Lys Ser Ser Asp Lys Thr His Thr Ser Pro Pro
450                 455                 460

Ser Pro Ala Pro Glu Leu Leu Gly Gly Pro Ser Val Phe Leu Phe Pro
465                 470                 475                 480

Pro Lys Pro Lys Asp Thr Leu Met Ala Ser Arg Thr Pro Glu Val Thr
                485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Asn Ser Thr Tyr Arg Val Val Ser Val Leu Thr Val
        530                 535                 540

Leu Ala Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Ser Arg Glu
            580                 585                 590

Glu Met Thr Lys Asn Gln Val Ser Leu Thr Cys Leu Val Lys Gly Phe
        595                 600                 605

Tyr Pro Ser Asp Ile Ala Val Glu Trp Glu Ser Asn Gly Gln Pro Glu
        610                 615                 620

Asn Asn Tyr Lys Thr Thr Pro Pro Val Leu Asp Ser Asp Gly Ser Phe
625                 630                 635                 640
```

Phe Leu Tyr Ser Lys Leu Thr Val Asp Lys Ser Arg Trp Gln Gln Gly
            645                 650                 655

Asn Val Phe Ser Cys Ser Val Met His Glu Ala Leu His Asn Ala Tyr
            660                 665                 670

Thr Gln Lys Ser Leu Ser Leu Ser Pro Gly Lys
        675                 680

<210> SEQ ID NO 25
<211> LENGTH: 699
<212> TYPE: PRT
<213> ORGANISM: Artificial Sequence
<220> FEATURE:
<223> OTHER INFORMATION: Synthetic Construct

<400> SEQUENCE: 25

Met Pro Leu Leu Leu Leu Pro Leu Trp Ala Gly Ala Leu Ala
1               5                   10                  15

His Thr Asp Leu Ser Gly Lys Val Phe Val Phe Pro Arg Glu Ser Val
            20                  25                  30

Thr Asp His Val Asn Leu Ile Thr Pro Leu Glu Lys Pro Leu Gln Asn
        35                  40                  45

Phe Thr Leu Cys Phe Arg Ala Tyr Ser Asp Leu Ser Arg Ala Tyr Ser
    50                  55                  60

Leu Phe Ser Tyr Asn Thr Gln Gly Arg Asp Asn Glu Leu Leu Val Tyr
65                  70                  75                  80

Lys Glu Arg Val Gly Glu Tyr Ser Leu Tyr Ile Gly Arg His Lys Val
                85                  90                  95

Thr Ser Lys Val Ile Glu Lys Phe Pro Ala Pro Val His Ile Cys Val
            100                 105                 110

Ser Trp Glu Ser Ser Ser Gly Ile Ala Glu Phe Trp Ile Asn Gly Thr
        115                 120                 125

Pro Leu Val Lys Lys Gly Leu Arg Gln Gly Tyr Phe Val Glu Ala Gln
    130                 135                 140

Pro Lys Ile Val Leu Gly Gln Glu Gln Asp Ser Tyr Gly Gly Lys Phe
145                 150                 155                 160

Asp Arg Ser Gln Ser Phe Val Gly Glu Ile Gly Asp Leu Tyr Met Trp
                165                 170                 175

Asp Ser Val Leu Pro Pro Glu Asn Ile Leu Ser Ala Tyr Gln Gly Thr
            180                 185                 190

Pro Leu Pro Ala Asn Ile Leu Asp Trp Gln Ala Leu Asn Tyr Glu Ile
        195                 200                 205

Arg Gly Tyr Val Ile Ile Lys Pro Leu Val Trp Val Glu Pro Lys Ser
    210                 215                 220

Ser Asp Lys Thr His Thr Ser Pro Pro Ser Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

```
Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys Gly Gly Gly Ser Gly Gly Gly Ser Gly Gly
    450                 455                 460

Gly Gly Ser Glu Pro Lys Ser Ser Asp Lys Thr His Thr Ser Pro Pro
465                 470                 475                 480

Ser Pro Ala Pro Glu Leu Leu Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Thr Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly Lys
    690                 695
```